United States Patent [19]
Harrington et al.

[11] Patent Number: 5,919,656
[45] Date of Patent: Jul. 6, 1999

[54] GENES ENCODING TELOMERASE PROTEIN 1

[75] Inventors: Lea Anne Harrington, Toronto, Canada; Murray O. Robinson, Malibu, Calif.

[73] Assignees: Amgen Canada Inc., Mississauga, Canada; Amgen Inc., Thousand Oaks, Calif.

[21] Appl. No.: 08/751,189

[22] Filed: Nov. 15, 1996

[51] Int. Cl.$^6$ .................... C07H 21/04; C07H 14/435; C12N 15/00; C12N 15/63
[52] U.S. Cl. .................. 435/69.1; 435/252.3; 435/320.1; 435/183; 536/23.5; 536/24.31; 536/24.33; 530/350
[58] Field of Search ............................. 536/23.5, 24.31, 536/24.33; 435/320.1, 240.2, 252.3, 254.11, 254.2, 172.3, 69.1, 93.2, 93.21, 183; 530/300, 350

[56] References Cited

U.S. PATENT DOCUMENTS

| | | |
|---|---|---|
| 3,773,919 | 11/1973 | Boswell et al. |
| 4,452,747 | 6/1984 | Gersonde et al. |
| 4,619,794 | 10/1986 | Hauser. |
| 5,489,743 | 2/1996 | Robinson et al. |
| 5,557,032 | 9/1996 | Mak ............................................ 800/2 |

FOREIGN PATENT DOCUMENTS

| | | |
|---|---|---|
| 0 036 676 | 3/1979 | European Pat. Off. |
| 0 052 322 | 11/1981 | European Pat. Off. |
| 0 058 481 | 1/1982 | European Pat. Off. |
| 0 088 046 | 2/1983 | European Pat. Off. |
| 0 143 949 | 10/1984 | European Pat. Off. |
| 0 154 316 | 3/1985 | European Pat. Off. |
| 0 401 384 | 12/1989 | European Pat. Off. |
| WO 94/28122 | 12/1994 | WIPO. |
| WO 96/01835 | 1/1995 | WIPO. |
| WO 96/19580 | 6/1995 | WIPO. |
| WO 96/01835 | 1/1996 | WIPO. |
| WO 98/07838 | 2/1998 | WIPO. |
| WO 98/08938 | 3/1998 | WIPO. |

OTHER PUBLICATIONS

Bodnar, et al., *Science*, 279: 349–352 (1988).
Harrington, et al., *Genes & Development*, 11: 3109–3115 (1997).
Nakayama, et al., *Nature Genetics*, 18: 65–68 (1998).
Weinrich, et al., *Nature Genetics*, 17: 498–502 (1997).
Beattie, et al., *Current Biology*, 8,: 177–180 (1998).
Genbank Database, Accession No. H33937.
Sherman et al., *Meth. Yeast Genet.*, Cold Spring Harbor Laboratory Press, Cold Spring Harbor, NY (1983).
Brems et al. In Protein Folding: In Vitro and In Vivo, ACS Symposium Series, ch 19, 1993.
Borman In Protein Folding and Design, CEN pp. 29–35, 1996.
Collins et al. Cell 81: 677–686, 1995.
Harley et al., *Nature*, 345, No. 6274: 458–460 (1990).
Greider, *Annu. Rev. Biochem.*, 65: 337–365 (1996).
Greider et al., *Cellular Aging and Cell Death*, Wiley–Liss Inc., New York, NY, pp. 123–138 (1996).
Levy et al., *J. Mol. Biol.*, 225: 951–960 (1992).
Harley et al., *Cold Spring Harbor Symposia on Quantitative Biology*, 59: 307–315 (1994).
Effros et al., *AIDS*, 10: 17–22 (1996).
Kim et al., *Science*, 266: 2011–2015 (1994).
Counter et al., *EMBO J.*, 11: 1921–1929 (1992).
Blasco et al., *Science*, 269: 1267–1270 (1995).
Feng et al., *Science*, 269: 1236–1241 (1995).
Blasco et al., *Nature Genetics*, 12: 200–204 (1996).
Avilion et al., *Cancer Res.*, 56: 645–650 (1996).
Harrington et al., *J. Biol. Chem.*, 270, No. 15: 8893–8901 (1995).
Collins et al., *Cell*, 81: 677–686 (1995).
Lingner et al., *Proc. Natl. Acad. Sci. USA*, 93: 10712–10717 (1996).
Sambrook et al., *Molecular Cloning: A Laboratory Manual*, 2d Edition, Cold Spring Harbor Laboratory Press, Cold Spring Harbor, NY (1989) (Table of Contents Provided).
Ausubel et al., eds., *Current Protocols in Molecular Biology,*, Green Publishing Assoc., Inc. and Wiley & Sons, Inc., NY (1994) (Table of Contents Provided).
Engels et al., *Angew. Chem. Intl. Ed. Engl.*, 28: 716–734 (1989).
Miller et al., *Genetic Engineering* 8: 277–298 (1986).
Ausubel et al., eds., *Current Protocols in Molecular Biology*, Unit 10.11B, Section entitled: *Metal–Chelate Affinity Chromatography*, pp. 10.11.8–10.11.22, John Wiley & Sons, New York (1993).
Marston et al., *Meth. Enz.*, 182: 264–275 (1990).
Merrifield et al., *J. Am. Chem. Soc.*, 85: 2149 (1964).
Houghten et al., *Proc Natl Acad. Sci. USA*, 82: 5131–5135 (1985).
Stewart and Young, *Solid Phase Peptide Synthesis*, Pierce Chem. Co., Rockford, IL (1984) (Table of Contents Provided).
Francis, *Focus on Growth Factors*, 3: 4–10 (May 1992).
Chamow et al..*Bioconjugate Chem.*, 5: 133–140 (1994).
*Remington's Pharmaceutical Sciences*, 18th Ed., A. R. Gennaro, ed., Mack Publishing Co., Easton, PA 18042 (1990) (Table of Contents Provided).
Sidman et al., *Biopolymers*, 22: 547–556 (1983).
Langer et al., *J. Biomed. Mater. Res.*, 15: 167–277 (1981).
Langer, *Chem. Tech.*, 12: 98–105 (1982).
Eppstein et al., *Proc. Natl. Acad. Sci. USA*, 82: 3688–3692 (1985).
Hwang et al., *Proc. Natl. Acad. Sci. USA*, 77, No. 7: 4030–4034 (1980).
Strahl et al., *Mol. Cell. Biol.*, 16, No. 1: 53–65 (1996).

(List continued on next page.)

*Primary Examiner*—Carla J. Myers
*Attorney, Agent, or Firm*—Nancy A. Oleski; Ron K. Levy; Steven M. Odre

[57] ABSTRACT

Disclosed are nucleic acid molecules encoding polypeptides that specifically bind telomerase RNA. Also disclosed are methods of preparing the nucleic acid molecules and polypeptides, and methods of using these molecules.

19 Claims, 24 Drawing Sheets

OTHER PUBLICATIONS

Mechler et al., Guide to Molecular Cloning Techniques, *Methods in Enzymology*, 152: 241–248 (1987).
Strathmann et al., *Proc. Natl. Acad. Sci. USA*, 88: 1247–1250, (1991).
Willson et al., *Cancer Res.*, 47: 2704–2713 (1987).
SenGupta et al., *Proc. Natl. Acad. Sci. USA*, 93: 8496–8501 (1996).
Sikorski et al., *Genetics*, 122: 19–27 (1989).
Legrain et al., *Nuc. Acids Res.*, 22, No. 15: 3241–3242 (1994).
Sherman et al., Meth. Yeast Genet., Cold Spring Harbor Laboratory Press, Cold Spring Harbor, NY (1983).
Chen et al., *Curr. Genet.*, 21: 83–84 (1992).
Ares, *Cell*, 47: 49–59 (1986).
Tollervey et al., *Cell*, 35: 753–762 (1983).
Brow et al., *Nature*, 334: 213–218 (1988).
Singer et al., *Science*, 266: 404–409 (1994).
Barinaga, *Science*, 275: 928 (1997).
Bryan, et al., *EMBO Journal*, 14, No. 17: 4240–4248 (1995).
Harley, *Journal of NIH Research*, 7: 64–68 (1995).
Harrington et al., *Science*, 275: 973–977 (1997).
Klingelhutz et al., *Nature*, 380: 79–82 (1996).
Krauskopf et al., *Nature*, 383: 354–357 (1996).
Lundblad et al., *Cell*, 87: 369–375 (1996).
Nakayama et al., *Molecular Biology of the Cell*, 7, Supp 5, (1996).
Prowse et al., *Proc. Natl. Acad. Sci. USA*, 92: 4818–4822, (1995).
van Steensel et al., *Nature*, 385: 740–743 (1997).
Vaziri et al., *Experimental Gerontology*, 31, Nos. 1/2: 295–301 (1996).
Wolthers et al., *Science*, 274: 1543–1547 (1996).
Yasui et al., *J. Cancer Res. Clin. Oncol.*, 122: 770–773 (1996).
Harrington, et al., *A Mammalian Telomerase–Associated Protein, Science*, 275: 973–977, (Feb. 14, 1997).
Nakayma, et al., *TLP1: A Gene Encoding a Protein Component of Mammalian Telomerase is a Novel Member of WD Repeats Family, Cell*, 88: 875–884, (Mar. 21, 1997).
Lingner, et al., *Reverse Transcriptase Motifs in the Catalytic Subunit of Telomerase, Science*, 276: 561–567, (Apr. 25, 1997).
Barinaga, *The Telomerase Picture Fills In, Science*, 276: 528–529, (Apr. 25, 1997).

FIGURE 1A

```
ATGGAAAAACTCCATGGGCATGTGTCTGCCCATCCAGACATCCTCTCCT
TGGAGAACCGGTGCCTGGCTATGCTCCCTGACTTACAGCCCTTGGAGAA
ACTACATCAGCATGTATCTACCCACTCAGATATCCTCTCCTTGAAGAAC
CAGTGCCTAGCCACGCTTCCTGACCTGAAGACCATGGAAAACCACATG
GATATGTGTCTGCCCACCCAGACATCCTCTCCTTGGAGAACCAGTGCCT
GGCCACACTTTCTGACCTGAAGACCATGGAGAAACCACATGGACATGTT
TCTGCCCACCCAGACATCCTCTCCTTGGAGAACCGGTGCCTGGCCACCC
TCCCTAGTCTAAAGAGCACTGTGTCTGCCAGCCCCTTGTTCCAGAGTCT
ACAGATATCTCACATGACGCAAGCTGATTTGTACCGTGTGAACAACAGC
AATTGCCTGCTCTCTGAGCCTCCAAGTTGGAGGGCTCAGCATTTCTCTA
AGGGACTAGACCTTTCAACCTGCCCTATAGCCCTGAAATCCATCTCTGC
CACAGAGACAGCTCAGGAAGCAACTTTGGGTCGTTGGTTTGATTCAGAA
GAGAAGAAGGGGCAGAGACCCAAATGCCTTCTTATAGTCTGAGCTTGG
GAGAGGAGGAGGAGGTGGAGGATCTGGCCGTGAAGCTCACCTCTGGAGA
CTCTGAATCTCATCCAGAGCCTACTGACCATGTCCTTCAGGAAAAGAAG
ATGGCTCTACTGAGCTTGCTGTGCTCTACTCTGGTCTCAGAAGTAAACA
TGAACAATACATCTGACCCCACCCTGGCTGCCATTTTTGAAATCTGTCG
TGAACTTGCCCTCCTGGAGCCTGAGTTTATCCTCAAGGCATCTTTGTAT
GCCAGGCAGCAGCTGAACGTCCGGAATGTGGCCAATAACATCTTGGCCA
```

FIGURE 1B

```
TTGCTGCTTTCTTGCCGGCGTGTCGCCCCACCTGCGACGATATTTCTG
TGCCATTGTCCAGCTGCCTTCTGACTGGATCCAGGTGGCTGAGCTTTAC
CAGAGCCTGGCTGAGGGAGATAAGAATAAGCTGGTGCCCTGCCCGCCT
GTCTCCGTACTGCCATGACGGACAAATTTGCCCAGTTTGACGAGTACCA
GCTGGCTAAGTACAACCCTCGGAAGCACGGGCCAAGAGACACCCCGC
CGGCCACCCCGCTCTCCAGGGATGGAGCCTCCATTTTCTCACAGATGTT
TTCCAAGGTACATAGGGTTTCTCAGAGAAGAGCAGAGAAAGTTTGAGAA
GGCCGGTGATACAGTGTCAGAGAAAAAGAATCCTCCAAGGTTCACCCTG
AAGAAGCTGGTTCAGCGACTGCACATCCACAAGCCTGCCCAGCACGTTC
AAGCCCTGCTGGGTTACAGATACCCTCCAACCTACAGCTCTTTTCTCG
AAGTCGCCTTCCTGGGCCTTGGGATTCTAGCAGAGCTGGGAAGAGGATG
AAGCTGTCTAGGCCAGAGACCTGGGAGCGGGAGCTGAGCCTACGGGGA
ACAAAGCGTCGGTCTGGGAGGAACTCATTGAAAATGGGAAGCTTCCCTT
CATGGCCATGCTTCGGAACCTGTGCAACCTGCTGCGGGTTGGAATCAGT
TCCCGCCACCATGAGCTCATTCTCCAGAGACTCCAGCATGGGAAGTCGG
TGATCCACAGTCGGCAGTTTCCATTCAGATTTCTTAACGCCCATGATGC
CATTGATGCCCTCGAGGCTCAACTCAGAAATCAAGCATTGCCCTTTCCT
TCGAATATAACACTGATGAGGCGGATACTAACTAGAAATGAAAAGAACC
GTCCCAGGCGGAGGTTTCTTTGCCACCTAAGCCGTCAGCAGCTTCGTAT
```

FIGURE 1C

```
GGCAATGAGGATACCTGTGTTGTATGAGCAGCTCAAGAGGGAGAAGCTG
AGAGTACACAAGGCCAGACAGTGGAAATATGATGGTGAGATGCTGAACA
GGTACCGACAGGCCCTAGAGACAGCTGTGAACCTCTCTGTGAAGCACAG
CCTGCCCCTGCTGCCAGGCCGCACTGTCTTGGTCTATCTGACAGATGCT
AATGCAGACAGGCTCTGTCCAAAGAGCAACCCACAAGGGCCCCGCTGA
ACTATGCACTGCTGTTGATTGGGATGATGATCACGAGGGCGGAGCAGGT
GGACGTCGTGCTGTGTGGAGGTGACACTCTGAAGACTGCAGTGCTTAAG
GCAGAAGAAGGCATCCTGAAGACTGCCATCAAGCTCCAGGCTCAAGTCC
AGGAGTTTGATGAAATGATGGATGGTCCCTGAATACTTTTGGGAAATA
CCTGCTGTCTCTGGCTGGCCAAAGGGTTCCTGTGGACAGGGTCATCCTC
CTTGGCCAAAGCATGGATGATGGAATGATAAATGTGGCCAAACAGCTTT
ACTGGCAGCGTGTGAATTCCAAGTGCCTCTTTGTTGGTATCCTCCTAAG
AAGGGTACAATACCTGTCAACAGATTTGAATCCCAATGATGTGACACTC
TCAGGCTGTACTGATGCGATACTGAAGTTCATTGCAGAGCATGGGGCCT
CCCATCTTCTGGAACATGTGGGCCAAATGGACAAAATATTCAAGATTCC
ACCACCCCAGGAAAGACAGGGGTCCAGTCTCTCCGGCCACTGGAAGAG
GACACTCCAAGCCCCTTGGCTCCTGTTTCCAGCAAGGATGGCGCAGCA
TCCGGCTTTTCATTTCATCCACTTTCCGAGACATGCACGGGGAGCGGGA
CCTGCTGCTGAGGTCTGTGCTGCCAGCACTGCAGGCCCGAGCGGCCCT
```

FIGURE 1D

CACCGTATCAGCCTTCACGGAATCGACCTCCGCTGGGGCGTCACTGAGG

AGGAGACCCGTAGGAACAGACAACTGGAAGTGTGCCTTGGGGAGGTGGA

GAACGCACAGCTGTTTGTGGGATTCTGGGCTCCCGTTATGGATACATT

CCCCCCAGCTACAACCTTCCTGACCATCCACACTTCCACTGGGCCCAGC

AGTACCCTTCAGGGCGCTCTGTGACAGAGATGGAGGTGATGCAGTTCCT

GAACCGGAACCAACGTCTGCAGCCCTCTGCCCAAGCTCTCATCTACTTC

CGGGATTCCAGCTTCCTCAGCTCTGTGCCAGATGCCTGGAAATCTGACT

TTGTTTCTGAGTCTGAAGAGGCCGCATGTCGGATCTCAGAACTGAAGAG

CTACCTAAGCAGACAGAAAGGGATAACCTGCCGCAGATACCCCTGTGAG

TGGGGGGGTGTGGCAGCTGGCCGGCCTATGTTGGCGGGCTGGAGGAGT

TTGGGCAGTTGGTTCTGCAGGATGTATGGAATATGATCCAGAAGCTCTA

CCTGCAGCCTGGGGCCCTGCTGGAGCAGCCAGTGTCCATCCCAGACGAT

GACTTGGTCCAGGCCACCTTCCAGCAGCTGCAGAAGCCACCGAGTCCTG

CCCGGCCACGCCTTCTTCAGGACACAGTGCAACAGCTGATGCTGCCCCA

CGGAAGGCTGAGCCTGGTGACGGGGCAGTCAGGACAGGGCAAGACAGCC

TTCCTGGCATCTCTTGTGTCAGCCCTGCAGGCTCCTGATGGGGCCAAGG

TGGCACCATTAGTCTTCTTCCACTTTTCTGGGGCTCGTCCTGACCAGGG

TCTTGCCCTCACTCTGCTCAGACGCCTCTGTACCTATCTGCGTGGCCAA

CTAAAAGAGCCAGGTGCCCTCCCCAGCACCTACCGAAGCCTGGTGTGGG

FIGURE 1E

```
AGCTGCAGCAGAGGCTGCTGCCCAAGTCTGCTGAGTCCCTGCATCCTGG
CCAGACCCAGGTCCTGATCATCGATGGGGCTGATAGGTTAGTGGACCAG
AATGGGCAGCTGATTTCAGACTGGATCCCAAAGAAGCTTCCCCGGTGTG
TACACCTGGTGCTGAGTGTGTCTAGTGATGCAGGCCTAGGGGAGACCCT
TGAGCAGAGCCAGGGTGCCCACGTGCTGGCCTTGGGGCCTCTGGAGGCC
TCTGCTCGGCCCGGCTGGTGAGAGAGGAGCTGGCCCTGTACGGGAAGC
GGCTGGAGGAGTCACCATTTAACAACCAGATGCGACTGCTGCTGGTGAA
GCGGGAATCAGGCCGGCCGCTCTACCTGCGCTTGGTCACCGATCACCTG
AGGCTCTTCACGCTGTATGAGCAGGTGTCTGAGAGACTCCGGACCCTGC
CTGCCACTGTCCCCCTGCTGCTGCAGCACATCCTGAGCACACTGGAGAA
GGAGCACGGGCCTGATGTCCTTCCCCAGGCCTTGACTGCCCTAGAAGTC
ACACGGAGTGGTTTGACTGTGGACCAGCTGCACGGAGTGCTGAGTGTGT
GGCGGACACTACCGAAGGGGACTAAGAGCTGGGAAGAAGCAGTGGCTGC
TGGTAACAGTGGAGACCCCTACCCCATGGGCCCGTTTGCCTGCCTCGTC
CAGAGTCTGCGCAGTTTGCTAGGGGAGGGCCCTCTGGAGCGCCCTGGTG
CCCGGCTGTGCCTCCCTGATGGGCCCCTGAGAACAGCAGCTAAACGTTG
CTATGGGAAGAGGCCAGGGCTAGAGGACACGGCACACATCCTCATTGCA
GCTCAGCTCTGGAAGACATGTGACGCTGATGCCTCAGGCACCTTCCGAA
GTTGCCCTCCTGAGGCTCTGGGAGACCTGCCTTACCACCTGCTCCAGAG
```

FIGURE 1F

```
CGGGAACCGTGGACTTCTTTCGAAGTTCCTTACCAACCTCCATGTGGTG

GCTGCACACTTGGAATTGGGTCTGGTCTCTCGGCTCTTGGAGGCCCATG

CCCTCTATGCTTCTTCAGTCCCCAAAGAGGAACAAAGCTCCCCGAGGC

TGACGTTGCAGTGTTTCGCACCTTCTGAGGCAGCAGGCTTCAATCCTC

AGCCAGTACCCCGGCTCCTGCCCAGCAGGCAGCCAACCAGCCCCTGG

ACTCACCTCTTTGCCACCAAGCCTCGCTGCTCTCCGGAGATGGCACCT

CCAACACACTACGATGGCTTAATAAACCCCGGACCATGAAAAATCAG

CAAAGCTCCAGCCTGTCTCTGGCAGTTTCCTCATCCCCTACTGCTGTGG

CCTTCTCCACCAATGGGCAAAGAGCAGCTGTGGGCACTGCCAATGGGAC

AGTTTACCTGTTGGACCTGAGAACTTGGCAGGAGGAGAAGTCTGTGGTG

AGTGGCTGTGATGGAATCTCTGCTTGTTTGTTCCTCTCCGATGATACAC

TCTTTCTTACTGCCTTCGACGGGCTCCTGGAGCTCTGGGACCTGCAGCA

TGGTTGTCGGGTGCTGCAGACTAAGGCTCACCAGTACCAAATCACTGGC

TGCTGCCTGAGCCCAGACTGCCGGCTGCTAGCCACCGTGTGCTTGGGAG

GATGCCTAAAGCTGTGGGACACAGTCCGTGGGCAGCTGGCCTTCCAGCA

CACCTACCCCAAGTCCCTGAACTGTGTTGCCTTCCACCCAGAGGGGCAG

GTAATAGCCACAGGCAGCTGGGCTGGCAGCATCAGCTTCTTCCAGGTGG

ATGGGCTCAAAGTCACCAAGGACCTGGGGGCACCCGGAGCCTCTATCCG

TACCTTGGCCTTCAATGTGCCTGGGGGGTTGTGGCTGTGGGCCGGCTG
```

FIGURE 1G

```
GACAGTATGGTGGAGCTGTGGGCCTGGCGAGAAGGGGCACGGCTGGCTG
CCTTCCCTGCCCACCATGGCTTTGTTGCTGCTGCGCTTTTCCTGCATGC
GGGTTGCCAGTTACTGACGGCTGGAGAGGATGGCAAGGTTCAGGTGTGG
TCAGGGTCTCTGGGTCGGCCCCGTGGGCACCTGGGTTCCCTTTCTCTCT
CTCCTGCCCTCTCTGTGGCACTCAGCCCAGATGGTGATCGGGTGGCTGT
TGGATATCGAGCGGATGGCATTAGGATCTACAAAATCTCTTCAGGTTCC
CAGGGGGCTCAGGGTCAGGCACTGGATGTGGCAGTGTCCGCCCTGGCCT
GGCTAAGCCCCAAGGTATTGGTGAGTGGTGCAGAAGATGGGTCCTTGCA
GGGCTGGGCACTCAAGGAATGCTCCCTTCAGTCCCTCTGGCTCCTGTCC
AGATTCCAGAAGCCTGTGCTAGGACTGGCCACTTCCCAGGAGCTCTTGG
CTTCTGCCTCAGAGGATTTCACAGTGCAGCTGTGGCCAAGGCAGCTGCT
GACGCGGCCACACAAGGCAGAAGACTTTCCCTGTGGCACTGAGCTGCGG
GGACATGAGGGCCCTGTGAGCTGCTGTAGTTTCAGCACTGATGGAGGCA
GCCTGGCCACCGGGGGCCGGGATCGGAGTCTCCTCTGCTGGGACGTGAG
GACACCCAAAACCCCTGTTTTGATCCACTCCTTCCCTGCCTGTCACCGT
GACTGGGTCACTGGCTGTGCCTGGACCAAAGATAACCTACTGATATCCT
GCTCCAGTGATGGCTCTGTGGGCTCTGGACCCAGAGTCAGGACAGCG
GCTTGGTCAGTTCCTGGGTCATCAGAGTGCTGTGAGCGCTGTGGCAGCT
GTGGAGGAGCACGTGGTGTCTGTGAGCCGGGATGGGACCTTGAAAGTGT
```

FIGURE 1H

```
GGGACCATCAAGGCGTGGAGCTGACCAGCATCCCTGCTCACTCAGGACC
CATTAGCCACTGTGCAGCTGCCATGGAGCCCCGTGCAGCTGGACAGCCT
GGGTCAGAGCTTCTGGTGGTAACCGTCGGGCTAGATGGGGCCACACGGT
TATGGCATCCACTCTTGGTGTGCCAAACCCACACCCTCCTGGGACACAG
CGGCCCAGTCCGTGCTGCTGCTGTTTCAGAACCTCAGGCCTCATGCTG
ACCGCCTCTGAGGATGGTTCTGTACGGCTCTGGCAGGTTCCTAAGGAAG
CAGATGACACATGTATACCAAGGAGTTCTGCAGCCGTCACTGCTGTGGC
TTGGGCACCAGATGGTTCCATGGCAGTATCTGGAAATCAAGCTGGGGAA
CTAATCTTGTGGCAGGAAGCTAAGGCTGTGGCCACAGCACAGGCTCCAG
GCCACATTGGTGCTCTGATCTGGTCCTCGGCACACACCTTTTTTGTCCT
CAGTGCTGATGAGAAAATCAGCGAGTGGCAAGTGAAACTGCGGAAGGGT
TCGGCACCCGGAAATTTGAGTCTTCACCTGAACCGAATTCTACAGGAGG
ACTTAGGGGTGCTGACAAGTCTGGATTGGGCTCCTGATGGTCACTTTCT
CATCTTGGCCAAAGCAGATTTGAAGTTACTTTGCATGAAGCCAGGGGAT
GCTCCATCTGAAATCTGGAGCAGCTATACAGAAATCCTATGATATTGT
CCACCCACAAGGAGTATGGCATATTTGTCCTGCAGCCCAAGGATCCTGG
AGTTCTTTCTTTCTTGAGGCAAAAGGAATCAGGAGAGTTTGAAGAGAGG
CTGAACTTTGATATAAACTTAGAGAATCCTAGTAGGACCCTAATATCGA
TAACTCAAGCCAAACCTGAATCTGAGTCCTCATTTTTGTGTGCCAGCTC
```

FIGURE 1I

TGATGGGATCCTATGGAACCTGGCCAAATGCAGCCCAGAAGGAGAATGG

ACCACAGGTAACATGTGGCAGAAAAAGCAAACACTCCAGAAACCCAAA

CTCCAGGGACAGACCCATCTACCTGCAGGGAATCTGATGCCAGCATGGA

TAGTGATGCCAGCATGGATAGTGAGCCAACACCACATCTAAAGACACGG

CAGCGTAGAAAGATTCACTCGGGCTCTGTCACAGCCCTCCATGTGCTAC

CTGAGTTGCTGGTGACAGCTTCGAAGGACAGAGATGTTAAGCTATGGGA

GAGACCCAGTATGCAGCTGCTGGGCCTGTTCCGATGCGAAGGGTCAGTG

AGCTGCCTGGAACCTTGGCTGGGCGCTAACTCCACCCTGCAGCTTGCCG

TGGGAGACGTGCAGGGCAATGTGTACTTTCTGAATTGGGAA

FIGURE 2A

ATGGAGAAGCTCTGTGGGCATGTGCCTGGCCATTCAGACATCCTCTCCT

TGAAGAACCGGTGCCTGACCATGCTCCCTGACCTCCAGCCCCTGGAGAA

AATACATGGACATAGATCTGTCCACTCAGACATCCTTTCCTTGGAGAAC

CAGTGTCTGACCATGCTCTCTGACCTCCAGCCCACGGAGAGAATAGATG

GGCATATATCTGTCCACCCAGACATCCTCTCCTTGGAGAATCGGTGCCT

GACCATGCTCCCTGACCTCCAGCCTCTGGAGAAGCTATGTGGACATATG

TCTAGTCATCCAGACGTCCTTTCTTTGGAAAACCAATGTCTAGCTACTC

TCCCCACTGTAAAGAGCACTGCATTGACCAGCCCCTTGCTCCAGGGTCT

TCACATATCTCATACGGCACAAGCTGATCTGCATAGCCTGAAAACTAGC

AACTGCCTGCTCCCTGAGCTTCCTACCAAGAAGACTCCATGTTTCTCTG

AGGAACTAGACCTTCCACCTGGACCCAGGGCCCTGAAATCCATGTCTGC

TACAGCTCAAGTCCAGGAAGTAGCCTTGGGTCAATGGTGTGTCTCCAAA

GAAAAGGAATTTCAAGAAGAAGAAAGCACAGAAGTCCCRATGCCTTTGT

ACAGTCTAAGCTTGGAAGAAGAAGAAGTGGAGGCACCGGTCTTAAAACT

CACATCTGGAGACTCTGGCTTTCATCCTGAAACCACTGACCAGGTCCTT

CAGGAGAAGAAGATGGCTCTCTTGACCTTACTCTGCTCTGCTCTGGCCT

CAAATGTGAATGTGAAAGATGCATCTGACCTTACCCGGGCATCCATCCT

TGAAGTCTGTAGTGCCCTGGCCTCCTTGGAACCGGAGTTCATCCTTAAG

GCATCTTTGTATGCTCGGCAGCAACTTAACCTCCGGGACATCGCCAATA

FIGURE 2B

```
CAGTTCTGGCTGTGGCTGCCCTCTTGCCAGCCTGCCGCCCCATGTACG

ACGGTATTACTCCGCCATTGTTCACCTGCCTTCAGACTGGATCCAGGTA

GCCGAGTTCTACCAGAGCCTGGCAGAAGGGGATGAGAAGAAGTTGGTGT

CCCTGCCTGCCTGTCTCCGAGCTGCCATGACCGACAAATTTGCCGAGTT

TGATGAGTACCAGCTAGCTAAGTACAACCCACGGAAACATCGGTCCAAG

AGGCGGTCCCGCCAGCCACCCCGCCCTCAAAAGACAGAACGTCCATTTT

CAGAGAGGGAAATGTTTTCCAAAGAGCCTTTGGCCCCTTAAAAATGA

ACAGATTACGTTTGAAGCAGCTTATAATGCAATGCCAGAGAAAAACAGG

CTACCACGGTTCACTCTGAAGAAGTTGGTAGAGTATCTACATATCCACA

AGCCTGCTCAGCACGTCCAGGCCCTGCTGGGCTACAGGTACCCAGCCAC

CCTAGAGCTCTTTTCTCGGAGTCACCTCCCTGGGCCGTGGGAGTCTAGC

AGAGCTGGTCAGCGGATGAAGCTCCGAAGGCCAGAGACCTGGGAGCGGG

AGCTGAGTTTACGGGGAAACAAAGCTTCTGTGTGGGAGGAGCTCATAGA

CAATGGGAAACTGCCCTTCATGGCCATGCTCCGGAACCTGTGTAACCTG

CTGCGGACTGGGATCAGTGCCCGCCACCATGAACTCGTTCTCCAGAGAC

TCCAGCATGAGAAATCTGTGGTTCACAGTCGGCAGTTTCCATTCAGATT

CCTTAATGCTCATGACTCTATCGATAAACTTGAGGCTCAGCTCAGAAGC

AAAGCATCACCCTTCCCTTCCAATACAACATTGATGAAACGGATAATGA

TTAGAAACTCAAAAAAAAATAGGAGGCCTGCCAGTCGGAAGCACCTGTG
```

FIGURE 2C

CACCCTGACGCGCCGGCAGCTTCGGGCAGCAATGACTATACCTGTGATG

TATGAGCAGCTCAAGCGGGAGAAACTGAGGCTGCACAAGGCCAGACAAT

GGAACTGTGATGTTGAGTTGCTGGAGCGCTATCGCCAGGCCCTGGAAAC

AGCTGTGAACCTCTCAGTAAAGCACAACCTATCCCCGATGCCTGGCCGA

ACCCTCTTGGTCTATCTCACAGATGCAAATGCCGACAGGCTCTGTCCCA

AGAGTCACTCACAAGGGCCTCCCCTGAACTATGTGCTGCTGCTGATCGG

AATGATGGTGGCTCGAGCCGAGCAAGTGACTGTTTGCTTGTGTGGGGGA

GGATTTGTGAAGACACCGGTACTTACAGCCGATGAAGGCATCCTGAAGA

CTGCCATCAAACTTCAGGCTCAAGTCCAGGAGTTAGAAGGCAATGATGA

GTGGCCCCTGGACACTTTTGGGAAGTATCTGCTGTCTCTGGCTGTCCAA

AGGACCCCCATTGACAGGGTCATCCTGTTTGGTCAAAGGATGGATACCG

AGCTCCTGAAAGTAGCCAAACAGATTATCTGGCAGCATGTGAATTCCAA

GTGCCTCTTTGTTGGTGTCCTCCTACAGAAAACACAGTACATATCACCA

AATTTGAATCCCAACGATGTGACGCTCTCAGGCTGCACTGACGGGATCC

TGAAATTCATTGCCGAACATGGAGCCTCTCGTCTCCTGGAACATGTGGG

ACAACTAGATAAACTATTCAAGATCCCCCCACCCCCAGGAAAGACACAG

GCACCGTCTCTCCGGCCGCTGGAGGAGAACATCCCTGGTCCCTTGGGTC

CTATTTCCCAGCATGGATGGCGCAATATCCGGCTTTTCATTTCATCCAC

TTTCCGTGACATGCATGGGGAGCGAGATTTGCTGATGAGATCTGTTCTG

FIGURE 2D

```
CCCGCACTGCAGGCCAGAGTGTTCCCCACCGCATCAGTCTTCACGCCA

TTGACCTGCGCTGGGGTATCACAGAGGAAGAGACCCGCAGGAACAGACA

ACTGGAAGTGTGCCTTGGGGAGGTGGAGAACTCACAGCTGTTCGTGGGG

ATTCTGGGCTCCCGCTATGGCTACATTCCCCCAGCTATGATCTTCCTG

ATCATCCCCACTTTCACTGGACCCATGAGTACCTTCAGGGCGATCCGT

GACAGAGATGGAGGTGATGCAATTCCTGAACCGTGGCCAACGCTCGCAG

CCTTCGGCCCAAGCTCTCATCTACTTCCGAGATCCTGATTTCCTTAGCT

CTGTGCCAGATGCCTGGAAACCTGACTTTATATCTGAGTCAGAAGAAGC

TGCACATCGGGTCTCAGAGCTGAAGAGATATCTACACGAACAGAAAGAG

GTTACCTGTCGCAGCTACTCCTGTGAATGGGGAGGTGTAGCGGCTGGCC

GGCCCTATACTGGGGGCCTGGAGGAGTTTGGACAGTTGGTTCTCCAGGA

TGTGTGGAGCATGATCCAGAAGCAGCACCTGCAGCCTGGGGCCCAGTTG

GAGCAGCCAACATCCATCTCAGAAGACGATTTGATCCAGACCAGCTTTC

AGCAGCTGAAGACCCCAACGAGTCCGGCACGGCCACGCCTTCTTCAGGA

TACAGTGCAGCAGCTGTTGCTGCCCATGGGAGGCTGAGCCTAGTGACT

GGGCAGGCAGGACAGGGAAGACTGCCTTTCTGGCATCCCTTGTGTCTG

CCCTGAAGGTCCCTGACCAGCCCAATGAGCCCCGTTCGTTTTCTTCCA

CTTTGCAGCAGCCCGCCCTGACCAGTGTCTTGCTCTCAACCTCCTCAGA

CGCCTCTGTACCCATCTGCGTCAAAAACTGGGAGAGCTGAGTGCCCTCC
```

FIGURE 2E

```
CCAGCACTTACAGAGGCCTGGTGTGGGAACTGCAGCAGAAGTTGCTCCT
CAAATTCGCTCAGTCGCTGCAGCCTGCTCAGACTTTGGTCCTTATCATC
GATGGGGCAGATAAGTTGGTGGATCGTAATGGGCAGCTGATTTCAGACT
GGATCCCCAAGTCTCTTCCGCGGCGAGTACACCTGGTGCTGAGTGTGTC
CAGTGACTCAGGCCTGGGTGAGACCCTTCAGCAAAGTCAGGGTGCTTAT
GTGGTGGCCTTGGGCTCTTTGGTCCCATCTTCAAGGGCTCAGCTTGTGA
GAGAAGAGCTAGCACTGTATGGGAAACGACTGGAGGAGTCACCTTTTAA
CAACCAGATGCGGCTGCTGCTGGCAAAGCAGGGTTCAAGCCTGCCATTG
TACCTGCACCTTGTCACTGACTACCTGAGGCTCTTCACACTGTATGAAC
AGGTGTCTGAGAGACTTCGAACCCTGCCCGCCACTCTCCCACTGCTCTT
GCAGCACATCCTGAGCACCTTGGAGCAAGAACATGGCCATGATGTCCTT
CCTCAGGCTTTGACTGCCCTTGAGGTCACACGAAGTGGTCTGACTGTGG
ACCAGCTACATGCAATCCTGAGCACATGGCTGATCTTGCCCAAGGAGAC
TAAGAGCTGGGAAGAAGTGCTGGCTGCCAGTCACAGTGGAAACCCTTTC
CCCTTGTGTCCATTTGCCTACCTTGTCCAGAGTCTACGCAGTTTACTAG
GGGAGGGCCCAGTGGAGCGCCCTGGTGCCCGTCTCTGCCTCTCTGATGG
GCCCCTGAGGACAACAATTAAACGTCGCTATGGGAAAGGCTGGGCTA
GAGAAGACTGCGCATGTCCTCATTGCAGCTCACCTCTGGAAGACGTGTG
ATCCTGATGCCTCGGGCACCTTCCGAAGTTGCCCTCCTGAGGCTCTGAA
```

FIGURE 2F

AGATTTACCTTACCACCTGCTCCAGAGCGGGAACCATGGTCTCCTTGCC

GAGTTTCTTACCAATCTCCATGTGGTTGCTGCATATCTGGAAGTGGGTC

TAGTCCCCGACCTCTTGGAGGCTCATGTGCTCTATGCTTCTTCAAAGCC

TGAAGCCAACCAGAAGCTCCCAGCGGCAGATGTTGCTGTTTTCCATACC

TTCCTGAGACAACAGGCTTCACTCCTTACCCAGTATCCTTTGCTCCTGC

TCCAGCAGGCAGCTAGCCAGCCTGAAGAGTCACCTGTTTGCTGCCAGGC

CCCCCTGCTCACCCAGCGATGGCACGACCAGTTCACACTGAAATGGATT

AATAAACCCCAGACCCTGAAGGGTCAGCAAAGCTTGTCTCTGACAATGT

CCTCATCCCCAACTGCTGTGGCCTTCTCCCCGAATGGGCAAAGAGCAGC

TGTGGGGACCGCCAGTGGGACAATTTACCTGTTGAACTTGAAAACCTGG

CAGGAGGAGAAGGCTGTGGTGAGTGGCTGTGACGGGATTTCCTCTTTTG

CATTCCTTTCGGACACTGCCCTTTTCCTTACTACCTTCGACGGGCACCT

AGAGCTTTGGGACCTGCAACATGGTTGTTGGGTGTTTCAGACCAAGGCC

CACCAGTACCAAATCACTGGCTGCTGCCTGAGCCCAGACCGCCGCCTGC

TGGCCACTGTGTGTTTGGGAGGATACCTAAAGCTGTGGGACACAGTCCG

AGGACAGCTGGCTTTTCAGTACACCCATCCAAAGTCTCTCAACTGCGTT

GCCTTCCACCCAGAGGGGCAGGTGGTAGCCACAGGCAGCTGGGCTGGCA

GCATTACCTTCTTCCAGGCAGATGGACTCAAAGTCACCAAGGAACTAGG

GGCCCCCGGACCCTCTGTCTGTAGTTTGGCATTCAACAAACCTGGGAAG

FIGURE 2G

ATTGTGGCTGTGGGCCGGATAGATGGGACAGTGGAGCTGTGGGCCTGGC

AAGAGGGTGCCCGGCTGGCGGCCTTCCCTGCACAGTGTGGCTGTGTCTC

TGCTGTTCTTTTCTTGCATGCTGGAGACCGGTTCCTGACTGCTGGAGAA

GATGGCAAGGCTCAGTTATGGTCAGGATTTCTTGGCCGGCCCAGGGGTT

GCCTGGGCTCTCTTCCTCTTTCTCCTGCACTCTCGGTGGCTCTCAACCC

AGACGGTGACCAGGTGGCTGTTGGGTACCGAGAAGATGGCATTAACATC

TACAAGATTTCTTCAGGTTCCCAGGGGCCTCAGCATCAAGAGCTAAATG

TGGCGGTGTCTGCACTGGTGTGGCTGAGCCCTAGTGTTTTGGTGAGTGG

TGCAGAAGATGGATCCCTGCATGGTTGGATGTTCAAGGGAGACTCCCTT

CATTCCCTGTGGCTGTTGTCGAGATACCAGAAGCCTGTGCTGGGACTGG

CTGCCTCCCGGGAACTCATGGCTGCTGCCTCAGAGGACTTCACTGTGAG

ACTGTGGCCCAGACAGCTGCTGACACAGCCACATGTGCATGCGGTAGAG

TTGCCCTGTTGTGCTGAACTCCGGGGACACGAGGGGCCAGTGTGCTGCT

GTAGCTTCAGCCCTGATGGAGGCATCTTGGCCACAGCTGGCAGGGATCG

GAATCTCCTTTGCTGGGACATGAAGATAGCCCAAGCCCCTCTCCTGATT

CACACTTTCTCGTCCTGTCATCGTGACTGGATCACTGGCTGTGCGTGGA

CCAAAGACAACATCCTGGTCTCCTGCTCGAGTGATGGCTCTGTGGGACT

CTGGAACCCAGAGGCAGGGCAGCAACTTGGCCAGTTCTCAGGCCACCAG

AGTGCCGTGAGCGCCGTGGTTGCTGTGGAGGAACACATTGTATCTGTGA

FIGURE 2H

```
GCCGAGATGGGACCTTGAAAGTGTGGACCATCAGGGTGTGGAGCTGAC

CAGCATCCCTGCCCATTCCGGACCCATCAGCCAGTGTGCAGCTGCTCTG

GAGCCCCGCCCAGGGGGACAGCCTGGATCAGAGCTTCTGGTGGTGACTG

TTGGACTAGATGGGGCCACAAAGTTGTGGCATCCCTGTTGGTGTGCCA

AATACGTACTCTCCAGGGACACAGTGGCCCAGTCACAGCAGCTGCTGCT

TCAGAGGCCTCAGGCCTCCTGCTGACCTCAGATGATAGCTCTGTACAGC

TCTGGCAGATACCAAAGGAAGCAGATGATTCATACAAACCTAGGAGTTC

TGTGGCCATCACTGCTGTGGCATGGGCACCGGATGGTTCTATGGTGGTG

TCCGGAAATGAAGCCGGGGAACTGACACTGTGGCAGCAAGCCAAGGCTG

TGGCTACCGCACAGGCTCCAGGCCGCGTCAGTCACCTGATCTGGTACTC

GGCAAATTCATTCTTCGTTCTCAGTGCTAATGAAAACGTCAGCGAGTGG

CAAGTGGGACTGAGGAAAGGTTCAACGTCCACCAGTTCCAGTCTTCATC

TGAAGAGAGTTCTGCAGGAGGACTGGGGAGTCTTGACAGGTCTGGGTCT

GGCCCCTGATGGCCAGTCTCTCATCTTGATGAAGAGGATGTGGAATTA

CTAGAGATGAAGCCTGGGTCTATTCCATCTTCTATCTGCAGGAGGTATG

GAGTACATTCTTCAATACTGTGCACCAGCAAGGAGTACGGCTTGTTCTA

CCTGCAGCAGGGGGACTCCGGATTACTTTCTATATTGGAGCAAAAGGAG

TCAGGGGAGTTTGAAGAGATCCTGGACTTCAATCTGAACTTAAATAATC

CTAATGGGTCCCCAGTATCAATCACTCAGGCCAAACCTGAGTCTGAATC
```

FIGURE 2I

ATCCCTTTTGTGCGCCACCTCTGATGGGATGCTGTGGAACTTATCTGAA

TGTACCTCAGAGGGAGAATGGATCGTAGATAACATTTGGCAGAAAAAG

CAAAAAAACCTAAAACTCAGACTCTGGAGACAGAGTTGTCCCCGCACTC

AGAGTTGGATTTTTCCATTGATTGCTGGATTGATCCCACAAATTTAAAG

GCACAGCAGTGTAAAAGATCCACTTGGGCTCTGTCACAGCCCTCCATG

TGCTTCCGGGATTGCTGGTGACAGCTTCGAAGGACAGAGATGTTAAGCT

GTGGGAGAGACCCAGTATGCAGCTGCTGGGCTTGTTCCGATGTGAAGGG

CCAGTGAGCTGTCTGGAACCTTGGATGGAGCCCAGCTCTCCCCTGCAGC

TTGCTGTGGGAGACACACAAGGAAACTTGTATTTTCTATCTTGGGAA

FIGURE 3A

MEKLHGHVSAHPDILSLENRCLAMLPDLQPLEKLHQHVSTHSDILSLKN

QCLATLPDLKTMEKPHGYVSAHPDILSLENQCLATLSDLKTMEKPHGHV

SAHPDILSLENRCLATLPSLKSTVSASPLFQSLQISHMTQADLYRVNNS

NCLLSEPPSWRAQHFSKGLDLSTCPIALKSISATETAQEATLGRWFDSE

EKKGAETQMPSYSLSLGEEEEVEDLAVKLTSGDSESHPEPTDHVLQEKK

MALLSLLCSTLVSEVNMNNTSDPTLAAIFEICRELALLEPEFILKASLY

ARQQLNVRNVANNILAIAAFLPACRPHLRRYFCAIVQLPSDWIQVAELY

QSLAEGDKNKLVPLPACLRTAMTDKFAQFDEYQLAKYNPRKHRAKRHPR

RPPRSPGMEPPFSHRCFPRYIGFLREEQRKFEKAGDTVSEKKNPPRFTL

KKLVQRLHIHKPAQHVQALLGYRYPSNLQLFSRSRLPGPWDSSRAGKRM

KLSRPETWERELSLRGNKASVWEELIENGKLPFMAMLRNLCNLLRVGIS

SRHHELILQRLQHGKSVIHSRQFPFRFLNAHDAIDALEAQLRNQALPFP

SNITLMRRILTRNEKNRPRRRFLCHLSRQQLRMAMRIPVLYEQLKREKL

RVHKARQWKYDGEMLNRYRQALETAVNLSVKHSLPLLGRTVLVYLTDA

NADRLCPKSNPQGPPLNYALLLIGMMITRAEQVDVVLCGGDTLKTAVLK

AEEGILKTAIKLQAQVQEFDENDGWSLNTFGKYLLSLAGQRVPVDRVIL

LGQSMDDGMINVAKQLYWQRVNSKCLFVGILLRRVQYLSTDLNPNDVTL

SGCTDAILKFIAEHGASHLLEHVGQMDKIFKIPPPPGKTGVQSLRPLEE

DTPSPLAPVSQQGWRSIRLFISSTFRDMHGERDLLLRSVLPALQARAAP

FIGURE 3B

```
HRISLHGIDLRWGVTEEETRRNRQLEVCLGEVENAQLFVGILGSRYGYI

PPSYNLPDHPHFHWAQQYPSGRSVTEMEVMQFLNRNQRLQPSAQALIYF

RDSSFLSSVPDAWKSDFVSESEEAAXRISELKSYLSRQKGITCRRYPCE

WGGVAAGRPYVGGLEEFGQLVLQDVWNMIQKLYLQPGALLEQPVSIPDD

DLVQATFQQLQKPPSPARPRLLQDTVQXLMLPHGRLSLVTGQSGQGKTA

FLASLVSALQAPDGAKVAXLVFFHFSGARPDQGLALTLLRRLCTYLRGQ

LKEPGALPSTYRSLVWELQQRLLPKSAESLHPGQTQVLIIDGADRLVDQ

NGQLISDWIPKKLPRCVHLVLSVSSDAGLGETLEQSQGAHVLALGPLEA

SARARLVREELALYGKRLEESPFNNQMRLLLVKRESGRPLYLRLVTDHL

RLFTLYEQVSERLRTLPATVPLLLQHILSTLEKEHGPDVLPQALTALEV

TRSGLTVDQLHGVLSVWRTLPKGTKSWEEAVAAGNSGDPYPMGPFACLV

QSLRSLLGEGPLERPGARLCLPDGPLRTAAKRCYGKRPGLEDTAHILIA

AQLWKTCDADASGTFRSCPPEALGDLPYHLLQSGNRGLLSKFLTNLHVV

AAHLELGLVSRLLEAHALYASSVPKEEQKLPEADVAVFRTFLRQQASIL

SQYPRLLPQQAANQPLDSPLCHQASLLSRRWHLQHTLRWLNKPRTMKNQ

QSSSLSLAVSSSPTAVAFSTNGQRAAVGTANGTVYLLDLRTWQEEKSVV

SGCDGISACLFLSDDTLFLTAFDGLLELWDLQHGCRVLQTKAHQYQITG

CCLSPDCRLLATVCLGGCLKLWDTVRGQLAFQHTYPKSLNCVAFHPEGQ

VIATGSWAGSISFFQVDGLKVTKDLGAPGASIRTLAFNVPGGVVAVGRL
```

FIGURE 3C

DSMVELWAWREGARLAAFPAHHGFVAAALFLHAGCQLLTAGEDGKVQVW

SGSLGRPRGHLGSLSLSPALSVALSPDGDRVAVGYRADGIRIYKISSGS

QGAQGQALDVAVSALAWLSPKVLVSGAEDGSLQGWALKECSLQSLWLLS

RFQKPVLGLATSQELLASASEDFTVQLWPRQLLTRPHKAEDFPCGTELR

GHEGPVSCCSFSTDGGSLATGGRDRSLLCWDVRTPKTPVLIHSFPACHR

DWVTGCAWTKDNLLISCSSDGSVGLWDPESGQRLGQFLGHQSAVSAVAA

VEEHVVSVSRDGTLKVWDHQGVELTSIPAHSGPISHCAAAMEPRAAGQP

GSELLVVTVGLDGATRLWHPLLVCQTHTLLGHSGPVRAAAVSETSGLML

TASEDGSVRLWQVPKEADDTCIPRSSAAVTAVAWAPDGSMAVSGNQAGE

LILWQEAKAVATAQAPGHIGALIWSSAHTFFVLSADEKISEWQVKLRKG

SAPGNLSLHLNRILQEDLGVLTSLDWAPDGHFLILAKADLKLLCMKPGD

APSEIWSSYTENPMILSTHKEYGIFVLQPKDPGVLSFLRQKESGEFEER

LNFDINLENPSRTLISITQAKPESESSFLCASSDGILWNLAKCSPEGEW

TTGNMWQKKANTPETQTPGTDPSTCRESDASMDSDASMDSEPTPHLKTR

QRRKIHSGSVTALHVLPELLVTASKDRDVKLWERPSMQLLGLFRCEGSV

SCLEPWLGANSTLQLAVGDVQGNVYFLNWE

FIGURE 4A

MEKLCGHVPGHSDILSLKNRCLTMLPDLQPLEKIHGHRSVHSDILSLEN

QCLTMLSDLQPTERIDGHISVHPDILSLENRCLTMLPDLQPLEKLCGHM

SSHPDVLSLENQCLATLPTVKSTALTSPLLQGLHISHTAQADLHSLKTS

NCLLPELPTKKTPCFSEELDLPPGPRALKSMSATAQVQEVALGQWCVSK

EKEFQEEESTEVPMPLYSLSLEEEEVEAPVLKLTSGDSGFHPETTDQVL

QEKKMALLTLLCSALASNVNVKDASDLTRASILEVCSALASLEPEFILK

ASLYARQQLNLRDIANTVLAVAALLPACRPHVRRYYSAIVHLPSDWIQV

AEFYQSLAEGDEKKLVSLPACLRAAMTDKFAEFDEYQLAKYNPRKHRSK

RRSRQPPRPQKTERPFSERGKCFPKSLWPLKNEQITFEAAYNAMPEKNR

LPRFTLKKLVEYLHIHKPAQHVQALLGYRYPATLELFSRSHLPGPWESS

RAGQRMKLRRPETWERELSLRGNKASVWEELIDNGKLPFMAMLRNLCNL

LRTGISARHHELVLQRLQHEKSVVHSRQFPFRFLNAHDSIDKLEAQLRS

KASPFPSNTTLMKRIMIRNSKKNRRPASRKHLCTLTRRQLRAAMTIPVM

YEQLKREKLRLHKARQWNCDVELLERYRQALETAVNLSVKHNLSPMPGR

TLLVYLTDANADRLCPKSHSQGPPLNYVLLIGMMVARAEQVTVCLCGG

GFVKTPVLTADEGILKTAIKLQAQVQELEGNDEWPLDTFGKYLLSLAVQ

RTPIDRVILFGQRMDTELLKVAKQIIWQHVNSKCLFVGVLLQKTQYISP

NLNPNDVTLSGCTDGILKFIAEHGASRLLEHVGQLDKLFKIPPPPGKTQ

APSLRPLEENIPGPLGPISQHGWRNIRLFISSTFRDMHGERDLLMRSVL

FIGURE 4B

PALQARVFPHRISLHAIDLRWGITEEETRRNRQLEVCLGEVENSQLFVG

ILGSRYGYIPPSYDLPDHPHFHWTHEYPSGRSVTEMEVMQFLNRGQRSQ

PSAQALIYFRDPDFLSSVPDAWKPDFISESEEAAHRVSELKRYLHEQKE

VTCRSYSCEWGGVAAGRPYTGGLEEFGQLVLQDVWSMIQKQHLQPGAQL

EQPTSISEDDLIQTSFQQLKTPTSPARPRLLQDTVQQLLLPHGRLSLVT

GQAGQGKTAFLASLVSALKVPDQPNEPPFVFFHFAAARPDQCLALNLLR

RLCTHLRQKLGELSALPSTYRGLVWELQQKLLLKFAQSLQPAQTLVLII

DGADKLVDRNGQLISDWIPKSLPRRVHLVLSVSSDSGLGETLQQSQGAY

VVALGSLVPSSRAQLVREELALYGKRLEESPFNNQMRLLLAKQGSSLPL

YLHLVTDYLRLFTLYEQVSERLRTLPATLPLLLQHILSTLEQEHGHDVL

PQALTALEVTRSGLTVDQLHAILSTWLILPKETKSWEEVLAASHSGNPF

PLCPFAYLVQSLRSLLGEGPVERPGARLCLSDGPLRTTIKRRYGKRLGL

EKTAHVLIAAHLWKTCDPDASGTFRSCPPEALKDLPYHLLQSGNHGLLA

EFLTNLHVVAAYLEVGLVPDLLEAHVLYASSKPEANQKLPAADVAVFHT

FLRQQASLLTQYPLLLLQQAASQPEESPVCCQAPLLTQRWHDQFTLKWI

NKPQTLKGQQSLSLTMSSSPTAVAFSPNGQRAAVGTASGTIYLLNLKTW

QEEKAVVSGCDGISSFAFLSDTALFLTTFDGHLELWDLQHGCWVFQTKA

HQYQITGCCLSPDRRLLATVCLGGYLKLWDTVRGQLAFQYTHPKSLNCV

AFHPEGQVVATGSWAGSITFFQADGLKVTKELGAPGPSVCSLAFNKPGK

FIGURE 4C

IVAVGRIDGTVELWAWQEGARLAAFPAQCGCVSAVLFLHAGDRFLTAGE

DGKAQLWSGFLGRPRGCLGSLPLSPALSVALNPDGDQVAVGYREDGINI

YKISSGSQGPQHQELNVAVSALVWLSPSVLVSGAEDGSLHGWMFKGDSL

HSLWLLSRYQKPVLGLAASRELMAAASEDFTVRLWPRQLLTQPHVHAVE

LPCCAELRGHEGPVCCCSFSPDGGILATAGRDRNLLCWDMKIAQAPLLI

HTFSSCHRDWITGCAWTKDNILVSCSSDGSVGLWNPEAGQQLGQFSGHQ

SAVSAVVAVEEHIVSVSRDGTLKVWDHQGVELTSIPAHSGPISQCAAAL

EPRPGGQPGSELLVVTVGLDGATKLWHPLLVCQIRTLQGHSGPVTAAAA

SEASGLLLTSDDSSVQLWQIPKEADDSYKPRSSVAITAVAWAPDGSMVV

SGNEAGELTLWQQAKAVATAQAPGRVSHLIWYSANSFFVLSANENVSEW

QVGLRKGSTSTSSSLHLKRVLQEDWGVLTGLGLAPDGQSLILMKEDVEL

LEMKPGSIPSSICRRYGVHSSILCTSKEYGLFYLQQGDSGLLSILEQKE

SGEFEEILDFNLNLNNPNGSPVSITQAKPESESSLLCATSDGMLWNLSE

CTSEGEWIVDNIWQKKAKKPKTQTLETELSPHSELDFSIDCWIDPTNLK

AQQCKKIHLGSVTALHVLPGLLVTASKDRDVKLWERPSMQLLGLFRCEG

PVSCLEPWMEPSSPLQLAVGDTQGNLYFLSWE

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 7881 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGGAAAAAC TCCATGGGCA TGTGTCTGCC CATCCAGACA TCCTCTCCTT GGAGAACCGG      60

TGCCTGGCTA TGCTCCCTGA CTTACAGCCC TTGGAGAAAC TACATCAGCA TGTATCTACC     120

CACTCAGATA TCCTCTCCTT GAAGAACCAG TGCCTAGCCA CGCTTCCTGA CCTGAAGACC     180

ATGGAAAAAC CACATGGATA TGTGTCTGCC CACCCAGACA TCCTCTCCTT GGAGAACCAG     240

TGCCTGGCCA CACTTTCTGA CCTGAAGACC ATGGAGAAAC CACATGGACA TGTTTCTGCC     300
```

```
CACCCAGACA TCCTCTCCTT GGAGAACCGG TGCCTGGCCA CCCTCCCTAG TCTAAAGAGC    360

ACTGTGTCTG CCAGCCCCTT GTTCCAGAGT CTACAGATAT CTCACATGAC GCAAGCTGAT    420

TTGTACCGTG TGAACAACAG CAATTGCCTG CTCTCTGAGC CTCCAAGTTG GAGGGCTCAG    480

CATTTCTCTA AGGGACTAGA CCTTTCAACC TGCCCTATAG CCCTGAAATC CATCTCTGCC    540

ACAGAGACAG CTCAGGAAGC AACTTTGGGT CGTTGGTTTG ATTCAGAAGA GAAGAAAGGG    600

GCAGAGACCC AAATGCCTTC TTATAGTCTG AGCTTGGGAG AGGAGGAGGA GGTGGAGGAT    660

CTGGCCGTGA AGCTCACCTC TGGAGACTCT GAATCTCATC CAGAGCCTAC TGACCATGTC    720

CTTCAGGAAA AGAAGATGGC TCTACTGAGC TTGCTGTGCT CTACTCTGGT CTCAGAAGTA    780

AACATGAACA ATACATCTGA CCCCACCCTG GCTGCCATTT TGAAATCTG TCGTGAACTT     840

GCCCTCCTGG AGCCTGAGTT TATCCTCAAG GCATCTTTGT ATGCCAGGCA GCAGCTGAAC    900

GTCCGGAATG TGGCCAATAA CATCTTGGCC ATTGCTGCTT TCTTGCCGGC GTGTCGCCCC    960

CACCTGCGAC GATATTTCTG TGCCATTGTC CAGCTGCCTT CTGACTGGAT CCAGGTGGCT    1020

GAGCTTTACC AGAGCCTGGC TGAGGGAGAT AAGAATAAGC TGGTGCCCCT GCCCGCCTGT    1080

CTCCGTACTG CCATGACGGA CAAATTTGCC CAGTTTGACG AGTACCAGCT GGCTAAGTAC    1140

AACCCTCGGA AGCACCGGGC CAAGAGACAC CCCCGCCGGC CACCCCGCTC TCCAGGGATG    1200

GAGCCTCCAT TTTCTCACAG ATGTTTTCCA AGGTACATAG GGTTTCTCAG AGAAGAGCAG    1260

AGAAAGTTTG AGAAGGCCGG TGATACAGTG TCAGAGAAAA AGAATCCTCC AAGGTTCACC    1320

CTGAAGAAGC TGGTTCAGCG ACTGCACATC CACAAGCCTG CCCAGCACGT TCAAGCCCTG    1380

CTGGGTTACA GATACCCCTC CAACCTACAG CTCTTTTCTC GAAGTCGCCT TCCTGGGCCT    1440

TGGGATTCTA GCAGAGCTGG GAAGAGGATG AAGCTGTCTA GGCCAGAGAC CTGGGAGCGG    1500

GAGCTGAGCC TACGGGGAA CAAAGCGTCG GTCTGGGAGG AACTCATTGA AAATGGGAAG     1560

CTTCCCTTCA TGGCCATGCT TCGGAACCTG TGCAACCTGC TGCGGGTTGG AATCAGTTCC    1620

CGCCACCATG AGCTCATTCT CCAGAGACTC CAGCATGGGA AGTCGGTGAT CCACAGTCGG    1680

CAGTTTCCAT TCAGATTTCT TAACGCCCAT GATGCCATTG ATGCCCTCGA GGCTCAACTC    1740

AGAAATCAAG CATTGCCCTT TCCTTCGAAT ATAACACTGA TGAGGCGGAT ACTAACTAGA    1800

AATGAAAAGA ACCGTCCCAG GCGGAGGTTT CTTTGCCACC TAAGCCGTCA GCAGCTTCGT    1860

ATGGCAATGA GGATACCTGT GTTGTATGAG CAGCTCAAGA GGGAGAAGCT GAGAGTACAC    1920

AAGGCCAGAC AGTGGAAATA TGATGGTGAG ATGCTGAACA GGTACCGACA GGCCCTAGAG    1980

ACAGCTGTGA ACCTCTCTGT GAAGCACAGC CTGCCCCTGC TGCCAGGCCG CACTGTCTTG    2040

GTCTATCTGA CAGATGCTAA TGCAGACAGG CTCTGTCCAA AGAGCAACCC ACAAGGGCCC    2100

CCGCTGAACT ATGCACTGCT GTTGATTGGG ATGATGATCA CGAGGGCGGA GCAGGTGGAC    2160

GTCGTGCTGT GTGGAGGTGA CACTCTGAAG ACTGCAGTGC TTAAGGCAGA AGAAGGCATC    2220

CTGAAGACTG CCATCAAGCT CCAGGCTCAA GTCCAGGAGT TTGATGAAAA TGATGGATGG    2280

TCCCTGAATA CTTTTGGGAA ATACCTGCTG TCTCTGGCTG GCCAAAGGGT TCCTGTGGAC    2340

AGGGTCATCC TCCTTGGCCA AAGCATGGAT GATGGAATGA TAAATGTGGC CAAACAGCTT    2400

TACTGGCAGC GTGTGAATTC CAAGTGCCTC TTTGTTGGTA TCCTCCTAAG AAGGGTACAA    2460

TACCTGTCAA CAGATTTGAA TCCCAATGAT GTGACACTCT CAGGCTGTAC TGATGCGATA    2520

CTGAAGTTCA TTGCAGAGCA TGGGGCCTCC ATCTTCTGG AACATGTGGG CCAAATGGAC     2580

AAAATATTCA AGATTCCACC ACCCCCAGGA AAGACAGGGG TCCAGTCTCT CCGGCCACTG    2640

GAAGAGGACA CTCCAAGCCC CTTGGCTCCT GTTTCCCAGC AAGGATGGCG CAGCATCCGG    2700
```

```
CTTTTCATTT CATCCACTTT CCGAGACATG CACGGGGAGC GGGACCTGCT GCTGAGGTCT    2760

GTGCTGCCAG CACTGCAGGC CCGAGCGGCC CCTCACCGTA TCAGCCTTCA CGGAATCGAC    2820

CTCCGCTGGG GCGTCACTGA GGAGGAGACC CGTAGGAACA GACAACTGGA AGTGTGCCTT    2880

GGGGAGGTGG AGAACGCACA GCTGTTTGTG GGGATTCTGG GCTCCCGTTA TGGATACATT    2940

CCCCCCAGCT ACAACCTTCC TGACCATCCA CACTTCCACT GGGCCCAGCA GTACCCTTCA    3000

GGGCGCTCTG TGACAGAGAT GGAGGTGATG CAGTTCCTGA ACCGGAACCA ACGTCTGCAG    3060

CCCTCTGCCC AAGCTCTCAT CTACTTCCGG GATTCCAGCT TCCTCAGCTC TGTGCCAGAT    3120

GCCTGGAAAT CTGACTTTGT TTCTGAGTCT GAAGAGGCCG CATGTCGGAT CTCAGAACTG    3180

AAGAGCTACC TAAGCAGACA GAAAGGGATA ACCTGCCGCA GATACCCCTG TGAGTGGGGG    3240

GGTGTGGCAG CTGGCCGGCC CTATGTTGGC GGGCTGGAGG AGTTTGGGCA GTTGGTTCTG    3300

CAGGATGTAT GGAATATGAT CCAGAAGCTC TACCTGCAGC CTGGGGCCCT GCTGGAGCAG    3360

CCAGTGTCCA TCCCAGACGA TGACTTGGTC CAGGCCACCT TCCAGCAGCT GCAGAAGCCA    3420

CCGAGTCCTG CCCGGCCACG CCTTCTTCAG GACACAGTGC AACAGCTGAT GCTGCCCCAC    3480

GGAAGGCTGA GCCTGGTGAC GGGGCAGTCA GGACAGGGCA AGACAGCCTT CCTGGCATCT    3540

CTTGTGTCAG CCCTGCAGGC TCCTGATGGG CCAAGGTGG CACCATTAGT CTTCTTCCAC    3600

TTTTCTGGGG CTCGTCCTGA CCAGGGTCTT GCCCTCACTC TGCTCAGACG CCTCTGTACC    3660

TATCTGCGTG GCCAACTAAA AGAGCCAGGT GCCCTCCCCA GCACCTACCG AAGCCTGGTG    3720

TGGGAGCTGC AGCAGAGGCT GCTGCCCAAG TCTGCTGAGT CCCTGCATCC TGGCCAGACC    3780

CAGGTCCTGA TCATCGATGG GGCTGATAGG TTAGTGGACC AGAATGGGCA GCTGATTTCA    3840

GACTGGATCC CAAAGAAGCT TCCCCGGTGT GTACACCTGG TGCTGAGTGT GTCTAGTGAT    3900

GCAGGCCTAG GGGAGACCCT TGAGCAGAGC CAGGGTGCCC ACGTGCTGGC CTTGGGGCCT    3960

CTGGAGGCCT CTGCTCGGGC CCGGCTGGTG AGAGAGGAGC TGGCCCTGTA CGGGAAGCGG    4020

CTGGAGGAGT CACCATTTAA CAACCAGATG CGACTGCTGC TGGTGAAGCG GGAATCAGGC    4080

CGGCCGCTCT ACCTGCGCTT GGTCACCGAT CACCTGAGGC TCTTCACGCT GTATGAGCAG    4140

GTGTCTGAGA GACTCCGGAC CCTGCCTGCC ACTGTCCCCC TGCTGCTGCA GCACATCCTG    4200

AGCACACTGG AGAAGGAGCA CGGGCCTGAT GTCCTTCCCC AGGCCTTGAC TGCCCTAGAA    4260

GTCACACGGA GTGGTTTGAC TGTGGACCAG CTGCACGGAG TGCTGAGTGT GTGGCGGACA    4320

CTACCGAAGG GGACTAAGAG CTGGGAAGAA GCAGTGGCTG CTGGTAACAG TGGAGACCCC    4380

TACCCCATGG GCCCGTTTGC CTGCCTCGTC CAGAGTCTGC GCAGTTTGCT AGGGGAGGGC    4440

CCTCTGGAGC GCCCTGGTGC CCGGCTGTGC CTCCCTGATG GGCCCCTGAG AACAGCAGCT    4500

AAACGTTGCT ATGGGAAGAG GCCAGGGCTA GAGGACACGG CACACATCCT CATTGCAGCT    4560

CAGCTCTGGA AGACATGTGA CGCTGATGCC TCAGGCACCT TCCGAAGTTG CCCTCCTGAG    4620

GCTCTGGGAG ACCTGCCTTA CCACCTGCTC CAGAGCGGGA ACCGTGGACT TCTTTCGAAG    4680

TTCCTTACCA ACCTCCATGT GGTGGCTGCA CACTTGGAAT TGGGTCTGGT CTCTCGGCTC    4740

TTGGAGGCCC ATGCCCTCTA TGCTTCTTCA GTCCCCAAAG AGGAACAAAA GCTCCCCGAG    4800

GCTGACGTTG CAGTGTTTCG CACCTTCCTG AGGCAGCAGG CTTCAATCCT CAGCCAGTAC    4860

CCCCGGCTCC TGCCCCAGCA GGCAGCCAAC CAGCCCCTGG ACTCACCTCT TGCCACCAA    4920

GCCTCGCTGC TCTCCCGGAG ATGGCACCTC CAACACACAC TACGATGGCT TAATAAACCC    4980

CGGACCATGA AAAATCAGCA AAGCTCCAGC CTGTCTCTGG CAGTTTCCTC ATCCCCTACT    5040

GCTGTGGCCT TCTCCACCAA TGGGCAAAGA GCAGCTGTGG GCACTGCCAA TGGGACAGTT    5100
```

```
TACCTGTTGG ACCTGAGAAC TTGGCAGGAG GAGAAGTCTG TGGTGAGTGG CTGTGATGGA   5160

ATCTCTGCTT GTTTGTTCCT CTCCGATGAT ACACTCTTTC TTACTGCCTT CGACGGGCTC   5220

CTGGAGCTCT GGGACCTGCA GCATGGTTGT CGGGTGCTGC AGACTAAGGC TCACCAGTAC   5280

CAAATCACTG GCTGCTGCCT GAGCCCAGAC TGCCGGCTGC TAGCCACCGT GTGCTTGGGA   5340

GGATGCCTAA AGCTGTGGGA CACAGTCCGT GGGCAGCTGG CCTTCCAGCA CACCTACCCC   5400

AAGTCCCTGA ACTGTGTTGC CTTCCACCCA GAGGGGCAGG TAATAGCCAC AGGCAGCTGG   5460

GCTGGCAGCA TCAGCTTCTT CCAGGTGGAT GGGCTCAAAG TCACCAAGGA CCTGGGGGCA   5520

CCCGGAGCCT CTATCCGTAC CTTGGCCTTC AATGTGCCTG GGGGGTTGT GGCTGTGGGC    5580

CGGCTGGACA GTATGGTGGA GCTGTGGGCC TGGCGAGAAG GGGCACGGCT GGCTGCCTTC   5640

CCTGCCCACC ATGGCTTTGT TGCTGCTGCG CTTTTCCTGC ATGCGGGTTG CCAGTTACTG   5700

ACGGCTGGAG AGGATGGCAA GGTTCAGGTG TGGTCAGGGT CTCTGGGTCG GCCCCGTGGG   5760

CACCTGGGTT CCCTTTCTCT CTCTCCTGCC CTCTCTGTGG CACTCAGCCC AGATGGTGAT   5820

CGGGTGGCTG TTGGATATCG AGCGGATGGC ATTAGGATCT ACAAAATCTC TTCAGGTTCC   5880

CAGGGGGCTC AGGGTCAGGC ACTGGATGTG GCAGTGTCCG CCCTGGCCTG GCTAAGCCCC   5940

AAGGTATTGG TGAGTGGTGC AGAAGATGGG TCCTTGCAGG GCTGGGCACT CAAGGAATGC   6000

TCCCTTCAGT CCCTCTGGCT CCTGTCCAGA TTCCAGAAGC CTGTGCTAGG ACTGGCCACT   6060

TCCCAGGAGC TCTTGGCTTC TGCCTCAGAG GATTTCACAG TGCAGCTGTG GCCAAGGCAG   6120

CTGCTGACGC GGCCACACAA GGCAGAAGAC TTTCCCTGTG GCACTGAGCT GCGGGGACAT   6180

GAGGGCCCTG TGAGCTGCTG TAGTTTCAGC ACTGATGGAG GCAGCCTGGC CACCGGGGGC   6240

CGGGATCGGA GTCTCCTCTG CTGGGACGTG AGGACACCCA AAACCCCTGT TTTGATCCAC   6300

TCCTTCCCTG CCTGTCACCG TGACTGGGTC ACTGGCTGTG CCTGGACCAA AGATAACCTA   6360

CTGATATCCT GCTCCAGTGA TGGCTCTGTG GGGCTCTGGG ACCCAGAGTC AGGACAGCGG   6420

CTTGGTCAGT TCCTGGGTCA TCAGAGTGCT GTGAGCGCTG TGGCAGCTGT GGAGGAGCAC   6480

GTGGTGTCTG TGAGCCGGGA TGGGACCTTG AAAGTGTGGG ACCATCAAGG CGTGGAGCTG   6540

ACCAGCATCC CTGCTCACTC AGGACCCATT AGCCACTGTG CAGCTGCCAT GGAGCCCCGT   6600

GCAGCTGGAC AGCCTGGGTC AGAGCTTCTG GTGGTAACCG TCGGGCTAGA TGGGGCCACA   6660

CGGTTATGGC ATCCACTCTT GGTGTGCCAA ACCCACACCC TCCTGGGACA CAGCGGCCCA   6720

GTCCGTGCTG CTGCTGTTTC AGAAACCTCA GGCCTCATGC TGACCGCCTC TGAGGATGGT   6780

TCTGTACGGC TCTGGCAGGT TCCTAAGGAA GCAGATGACA CATGTATACC AAGGAGTTCT   6840

GCAGCCGTCA CTGCTGTGGC TTGGGCACCA GATGGTTCCA TGGCAGTATC TGGAAATCAA   6900

GCTGGGGAAC TAATCTTGTG GCAGGAAGCT AAGGCTGTGG CCACAGCACA GGCTCCAGGC   6960

CACATTGGTG CTCTGATCTG GTCCTCGGCA CACACCTTTT TTGTCCTCAG TGCTGATGAG   7020

AAAATCAGCG AGTGGCAAGT GAAACTGCGG AAGGGTTCGG CACCCGGAAA TTTGAGTCTT   7080

CACCTGAACC GAATTCTACA GGAGGACTTA GGGGTGCTGA CAAGTCTGGA TTGGGCTCCT   7140

GATGGTCACT TTCTCATCTT GGCCAAAGCA GATTTGAAGT TACTTTGCAT GAAGCCAGGG   7200

GATGCTCCAT CTGAAATCTG GAGCAGCTAT ACAGAAAATC CTATGATATT GTCCACCCAC   7260

AAGGAGTATG GCATATTTGT CCTGCAGCCC AAGGATCCTG GAGTTCTTTC TTTCTTGAGG   7320

CAAAAGGAAT CAGGAGAGTT TGAAGAGAGG CTGAACTTTG ATATAAACTT AGAGAATCCT   7380

AGTAGGACCC TAATATCGAT AACTCAAGCC AAACCTGAAT CTGAGTCCTC ATTTTTGTGT   7440

GCCAGCTCTG ATGGGATCCT ATGGAACCTG GCCAAATGCA GCCCAGAAGG AGAATGGACC   7500
```

```
ACAGGTAACA TGTGGCAGAA AAAAGCAAAC ACTCCAGAAA CCCAAACTCC AGGGACAGAC      7560

CCATCTACCT GCAGGGAATC TGATGCCAGC ATGGATAGTG ATGCCAGCAT GGATAGTGAG      7620

CCAACACCAC ATCTAAAGAC ACGGCAGCGT AGAAAGATTC ACTCGGGCTC TGTCACAGCC      7680

CTCCATGTGC TACCTGAGTT GCTGGTGACA GCTTCGAAGG ACAGAGATGT TAAGCTATGG      7740

GAGAGACCCA GTATGCAGCT GCTGGGCCTG TTCCGATGCG AAGGGTCAGT GAGCTGCCTG      7800

GAACCTTGGC TGGGCGCTAA CTCCACCCTG CAGCTTGCCG TGGGAGACGT GCAGGGCAAT      7860

GTGTACTTTC TGAATTGGGA A                                                7881

(2) INFORMATION FOR SEQ ID NO:2:

(i) SEQUENCE CHARACTERISTICS:
        (A) LENGTH: 7886 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ATGGAGAAGC TCTGTGGGCA TGTGCCTGGC CATTCAGACA TCCTCTCCTT GAAGAACCGG        60

TGCCTGACCA TGCTCCCTGA CCTCCAGCCC CTGGAGAAAA TACATGGACA TAGATCTGTC       120

CACTCAGACA TCCTTTCCTT GGAGAACCAG TGTCTGACCA TGCTCTCTGA CCTCCAGCCC       180

ACGGAGAGAA TAGATGGGCA TATATCTGTC CACCCAGACA TCCTCTCCTT GGAGAATCGG       240

TGCCTGACCA TGCTCCCTGA CCTCCAGCCT CTGGAGAAGC TATGTGGACA TATGTCTAGT       300

CATCCAGACG TCCTTTCTTT GGAAAACCAA TGTCTAGCTA CTCTCCCCAC TGTAAAGAGC       360

ACTGCATTGA CCAGCCCCTT GCTCCAGGGT CTTCACATAT CTCATACGGC ACAAGCTGAT       420

CTGCATAGCC TGAAAACTAG CAACTGCCTG CTCCCTGAGC TTCCTACCAA GAAGACTCCA       480

TGTTTCTCTG AGGAACTAGA CCTTCCACCT GGACCCAGGG CCCTGAAATC CATGTCTGCT       540

ACAGCTCAAG TCCAGGAAGT AGCCTTGGGT CAATGGTGTG TCTCCAAAGA AAAGGAATTT       600

CAAGAAGAAG AAAGCACAGA AGTCCCATGC CTTTGTACAG TCTAAGCTTG AAGAAGAAG       660

AAGTGGAGGC ACCGGTCTTA AAACTCACAT CTGGAGACTC TGGCTTTCAT CCTGAAACCA       720

CTGACCAGGT CCTTCAGGAG AAGAAGATGG CTCTCTTGAC CTTACTCTGC TCTGCTCTGG       780

CCTCAAATGT GAATGTGAAA GATGCATCTG ACCTTACCCG GGCATCCATC CTTGAAGTCT       840

GTAGTGCCCT GGCCTCCTTG AACCGGAGT TCATCCTTAA GGCATCTTTG TATGCTCGGC       900

AGCAACTTAA CCTCCGGGAC ATCGCCAATA CAGTTCTGGC TGTGGCTGCC CTCTTGCCAG       960

CCTGCCGCCC CCATGTACGA CGGTATTACT CCGCCATTGT TCACCTGCCT TCAGACTGGA      1020

TCCAGGTAGC CGAGTTCTAC CAGAGCCTGG CAGAAGGGGA TGAGAAGAAG TTGGTGTCCC      1080

TGCCTGCCTG TCTCCGAGCT GCCATGACCG ACAAATTTGC CGAGTTTGAT GAGTACCAGC      1140

TAGCTAAGTA CAACCCACGG AAACATCGGT CCAAGAGGCG GTCCCGCCAG CCACCCCGCC      1200

CTCAAAAGAC AGAACGTCCA TTTTCAGAGA GAGGGAAATG TTTTCCAAAG AGCCTTTGGC      1260

CCCTTAAAAA TGAACAGATT ACGTTTGAAG CAGCTTATAA TGCAATGCCA GAGAAAAACA      1320

GGCTACCACG GTTCACTCTG AAGAAGTTGG TAGAGTATCT ACATATCCAC AAGCCTGCTC      1380

AGCACGTCCA GGCCCTGCTG GGCTACAGGT ACCCAGCCAC CCTAGAGCTC TTTTCTCGGA      1440

GTCACCTCCC TGGGCCGTGG GAGTCTAGCA GAGCTGGTCA GCGGATGAAG CTCCGAAGGC      1500

CAGAGACCTG GGAGCGGGAG CTGAGTTTAC GGGGAAACAA AGCTTCTGTG TGGGAGGAGC      1560
```

```
TCATAGACAA TGGGAAACTG CCCTTCATGG CCATGCTCCG GAACCTGTGT AACCTGCTGC    1620

GGACTGGGAT CAGTGCCCGC CACCATGAAC TCGTTCTCCA GAGACTCCAG CATGAGAAAT    1680

CTGTGGTTCA CAGTCGGCAG TTTCCATTCA GATTCCTTAA TGCTCATGAC TCTATCGATA    1740

AACTTGAGGC TCAGCTCAGA AGCAAAGCAT CACCCTTCCC TTCCAATACA ACATTGATGA    1800

AACGGATAAT GATTAGAAAC TCAAAAAAAA ATAGGAGGCC TGCCAGTCGG AAGCACCTGT    1860

GCACCCTGAC GCGCCGGCAG CTTCGGGCAG CAATGACTAT ACCTGTGATG TATGAGCAGC    1920

TCAAGCGGGA GAAACTGAGG CTGCACAAGG CCAGACAATG GAACTGTGAT GTTGAGTTGC    1980

TGGAGCGCTA TCGCCAGGCC CTGGAAACAG CTGTGAACCT CTCAGTAAAG CACAACCTAT    2040

CCCCGATGCC TGGCCGAACC CTCTTGGTCT ATCTCACAGA TGCAAATGCC GACAGGCTCT    2100

GTCCCAAGAG TCACTCACAA GGGCCTCCCC TGAACTATGT GCTGCTGCTG ATCGGAATGA    2160

TGGTGGCTCG AGCCGAGCAA GTGACTGTTT GCTTGTGTGG GGGAGGATTT GTGAAGACAC    2220

CGGTACTTAC AGCCGATGAA GGCATCCTGA AGACTGCCAT CAAACTTCAG GCTCAAGTCC    2280

AGGAGTTAGA AGGCAATGAT GAGTGGCCCC TGGACACTTT TGGGAAGTAT CTGCTGTCTC    2340

TGGCTGTCCA AAGGACCCCC ATTGACAGGG TCATCCTGTT TGGTCAAAGG ATGGATACCG    2400

AGCTCCTGAA AGTAGCCAAA CAGATTATCT GGCAGCATGT GAATTCCAAG TGCCTCTTTG    2460

TTGGTGTCCT CCTACAGAAA ACACAGTACA TATCACCAAA TTTGAATCCC AACGATGTGA    2520

CGCTCTCAGG CTGCACTGAC GGGATCCTGA AATTCATTGC CGAACATGGA GCCTCTCGTC    2580

TCCTGGAACA TGTGGGACAA CTAGATAAAC TATTCAAGAT CCCCCCACCC CCAGGAAAGA    2640

CACAGGCACC GTCTCTCCGG CCGCTGGAGG AGAACATCCC TGGTCCCTTG GGTCCTATTT    2700

CCCAGCATGG ATGGCGCAAT ATCCGGCTTT TCATTTCATC CACTTTCCGT GACATGCATG    2760

GGGAGCGAGA TTTGCTGATG AGATCTGTTC TGCCCGCACT GCAGGCCAGA GTGTTCCCCC    2820

ACCGCATCAG TCTTCACGCC ATTGACCTGC GCTGGGGTAT CACAGAGGAA GAGACCCGCA    2880

GGAACAGACA ACTGGAAGTG TGCCTTGGGG AGGTGGAGAA CTCACAGCTG TTCGTGGGGA    2940

TTCTGGGCTC CCGCTATGGC TACATTCCCC CCAGCTATGA TCTTCCTGAT CATCCCCACT    3000

TTCACTGGAC CCATGAGTAC CCTTCAGGGC GATCCGTGAC AGAGATGGAG GTGATGCAAT    3060

TCCTGAACCG TGGCCAACGC TCGCAGCCTT CGGCCCAAGC TCTCATCTAC TTCCGAGATC    3120

CTGATTTCCT TAGCTCTGTG CCAGATGCCT GGAAACCTGA CTTTATATCT GAGTCAGAAG    3180

AAGCTGCACA TCGGGTCTCA GAGCTGAAGA GATATCTACA CGAACAGAAA GAGGTTACCT    3240

GTCGCAGCTA CTCCTGTGAA TGGGGAGGTG TAGCGGCTGG CCGGCCCTAT ACTGGGGGCC    3300

TGGAGGAGTT TGGACAGTTG GTTCTCCAGG ATGTGTGGAG CATGATCCAG AAGCAGCACC    3360

TGCAGCCTGG GGCCCAGTTG GAGCAGCCAA CATCCATCTC AGAAGACGAT TTGATCCAGA    3420

CCAGCTTTCA GCAGCTGAAG ACCCCAACGA GTCCGGCACG GCCACGCCTT CTTCAGGATA    3480

CAGTGCAGCA GCTGTTGCTG CCCCATGGGA GGCTGAGCCT AGTGACTGGG CAGGCAGGAC    3540

AGGGAAAGAC TGCCTTTCTG GCATCCCTTG TGTCTGCCCT GAAGGTCCCT GACCAGCCCA    3600

ATGAGCCCCC GTTCGTTTTC TTCCACTTTG CAGCAGCCCG CCCTGACCAG TGTCTTGCTC    3660

TCAACCTCCT CAGACGCCTC TGTACCCATC TGCGTCAAAA ACTGGGAGAG CTGAGTGCCC    3720

TCCCCAGCAC TTACAGAGGC CTGGTGTGGG AACTGCAGCA GAAGTTGCTC CTCAAATTCG    3780

CTCAGTCGCT GCAGCCTGCT CAGACTTTGG TCCTTATCAT CGATGGGGCA GATAAGTTGG    3840

TGGATCGTAA TGGGCAGCTG ATTTCAGACT GGATCCCCAA GTCTCTTCCG CGGCGAGTAC    3900

ACCTGGTGCT GAGTGTGTCC AGTGACTCAG GCCTGGGTGA GACCCTTCAG CAAAGTCAGG    3960
```

```
GTGCTTATGT GGTGGCCTTG GGCTCTTTGG TCCCATCTTC AAGGGCTCAG CTTGTGAGAG    4020

AAGAGCTAGC ACTGTATGGG AAACGACTGG AGGAGTCACC TTTTAACAAC CAGATGCGGC    4080

TGCTGCTGGC AAAGCAGGGT TCAAGCCTGC CATTGTACCT GCACCTTGTC ACTGACTACC    4140

TGAGGCTCTT CACACTGTAT GAACAGGTGT CTGAGAGACT TCGAACCCTG CCCGCCACTC    4200

TCCCACTGCT CTTGCAGCAC ATCCTGAGCA CCTTGGAGCA AGAACATGGC CATGATGTCC    4260

TTCCTCAGGC TTTGACTGCC CTTGAGGTCA CACGAAGTGG TCTGACTGTG GACCAGCTAC    4320

ATGCAATCCT GAGCACATGG CTGATCTTGC CCAAGGAGAC TAAGAGCTGG GAAGAAGTGC    4380

TGGCTGCCAG TCACAGTGGA AACCCTTTCC CCTTGTGTCC ATTTGCCTAC CTTGTCCAGA    4440

GTCTACGCAG TTTACTAGGG GAGGGCCCAG TGGAGCGCCC TGGTGCCCGT CTCTGCCTCT    4500

CTGATGGGCC CCTGAGGACA ACAATTAAAC GTCGCTATGG GAAAAGGCTG GGGCTAGAGA    4560

AGACTGCGCA TGTCCTCATT GCAGCTCACC TCTGGAAGAC GTGTGATCCT GATGCCTCGG    4620

GCACCTTCCG AAGTTGCCCT CCTGAGGCTC TGAAAGATTT ACCTTACCAC CTGCTCCAGA    4680

GCGGGAACCA TGGTCTCCTT GCCGAGTTTC TTACCAATCT CCATGTGGTT GCTGCATATC    4740

TGGAAGTGGG TCTAGTCCCC GACCTCTTGG AGGCTCATGT GCTCTATGCT TCTTCAAAGC    4800

CTGAAGCCAA CCAGAAGCTC CCAGCGGCAG ATGTTGCTGT TTTCCATACC TTCCTGAGAC    4860

AACAGGCTTC ACTCCTTACC CAGTATCCTT TGCTCCTGCT CCAGCAGGCA GCTAGCCAGC    4920

CTGAAGAGTC ACCTGTTTGC TGCCAGGCCC CCCTGCTCAC CCAGCGATGG CACGACCAGT    4980

TCACACTGAA ATGGATTAAT AAACCCCAGA CCCTGAAGGG TCAGCAAAGC TTGTCTCTGA    5040

CAATGTCCTC ATCCCCAACT GCTGTGGCCT TCTCCCCGAA TGGGCAAAGA GCAGCTGTGG    5100

GGACCGCCAG TGGGACAATT TACCTGTTGA ACTTGAAAAC CTGGCAGGAG GAGAAGGCTG    5160

TGGTGAGTGG CTGTGACGGG ATTTCCTCTT TTGCATTCCT TTCGGACACT GCCCTTTTCC    5220

TTACTACCTT CGACGGGCAC CTAGAGCTTT GGGACCTGCA ACATGGTTGT TGGGTGTTTC    5280

AGACCAAGGC CCACCAGTAC CAAATCACTG GCTGCTGCCT GAGCCCAGAC CGCCGCCTGC    5340

TGGCCACTGT GTGTTTGGGA GGATACCTAA AGCTGTGGGA CACAGTCCGA GGACAGCTGG    5400

CTTTTCAGTA CACCCATCCA AAGTCTCTCA ACTGCGTTGC CTTCCACCCA GAGGGGCAGG    5460

TGGTAGCCAC AGGCAGCTGG GCTGGCAGCA TTACCTTCTT CCAGGCAGAT GGACTCAAAG    5520

TCACCAAGGA ACTAGGGGCC CCCGGACCCT CTGTCTGTAG TTTGGCATTC AACAAACCTG    5580

GGAAGATTGT GGCTGTGGGC CGGATAGATG GGACAGTGGA GCTGTGGGCC TGGCAAGAGG    5640

GTGCCCGGCT GGCGGCCTTC CCTGCACAGT GTGGCTGTGT CTCTGCTGTT CTTTTCTTGC    5700

ATGCTGGAGA CCGGTTCCTG ACTGCTGGAG AAGATGGCAA GGCTCAGTTA TGGTCAGGAT    5760

TTCTTGGCCG GCCCAGGGGT TGCCTGGGCT CTCTTCCTCT TTCTCCTGCA CTCTCGGTGG    5820

CTCTCAACCC AGACGGTGAC CAGGTGGCTG TTGGGTACCG AGAAGATGGC ATTAACATCT    5880

ACAAGATTTC TTCAGGTTCC CAGGGGCCTC AGCATCAAGA GCTAAATGTG GCGGTGTCTG    5940

CACTGGTGTG GCTGAGCCCT AGTGTTTTGG TGAGTGGTGC AGAAGATGGA TCCCTGCATG    6000

GTTGGATGTT CAAGGGAGAC TCCCTTCATT CCCTGTGGCT GTTGTCGAGA TACCAGAAGC    6060

CTGTGCTGGG ACTGGCTGCC TCCCGGGAAC TCATGGCTGC TGCCTCAGAG GACTTCACTG    6120

TGAGACTGTG GCCCAGACAG CTGCTGACAC AGCCACATGT GCATGCGGTA GAGTTGCCCT    6180

GTTGTGCTGA ACTCCGGGGA CACGAGGGGC CAGTGTGCTG CTGTAGCTTC AGCCCTGATG    6240

GAGGCATCTT GGCCACAGCT GGCAGGGATC GGAATCTCCT TTGCTGGGAC ATGAAGATAG    6300

CCCAAGCCCC TCTCCTGATT CACACTTTCT CGTCCTGTCA TCGTGACTGG ATCACTGGCT    6360
```

```
GTGCGTGGAC CAAAGACAAC ATCCTGGTCT CCTGCTCGAG TGATGGCTCT GTGGGACTCT     6420

GGAACCCAGA GGCAGGGCAG CAACTTGGCC AGTTCTCAGG CCACCAGAGT GCCGTGAGCG     6480

CCGTGGTTGC TGTGGAGGAA CACATTGTAT CTGTGAGCCG AGATGGGACC TTGAAAGTGT     6540

GGGACCATCA GGGTGTGGAG CTGACCAGCA TCCCTGCCCA TTCCGGACCC ATCAGCCAGT     6600

GTGCAGCTGC TCTGGAGCCC CGCCCAGGGG ACAGCCTGG ATCAGAGCTT CTGGTGGTGA      6660

CTGTTGGACT AGATGGGGCC ACAAAGTTGT GGCATCCCCT GTTGGTGTGC CAAATACGTA     6720

CTCTCCAGGG ACACAGTGGC CCAGTCACAG CAGCTGCTGC TTCAGAGGCC TCAGGCCTCC     6780

TGCTGACCTC AGATGATAGC TCTGTACAGC TCTGGCAGAT ACCAAAGGAA GCAGATGATT     6840

CATACAAACC TAGGAGTTCT GTGGCCATCA CTGCTGTGGC ATGGGCACCG GATGGTTCTA     6900

TGGTGGTGTC CGGAAATGAA GCCGGGGAAC TGACACTGTG GCAGCAAGCC AAGGCTGTGG     6960

CTACCGCACA GGCTCCAGGC CGCGTCAGTC ACCTGATCTG GTACTCGGCA AATTCATTCT     7020

TCGTTCTCAG TGCTAATGAA AACGTCAGCG AGTGGCAAGT GGGACTGAGG AAAGGTTCAA     7080

CGTCCACCAG TTCCAGTCTT CATCTGAAGA GAGTTCTGCA GGAGGACTGG GGAGTCTTGA     7140

CAGGTCTGGG TCTGGCCCCT GATGGCCAGT CTCTCATCTT GATGAAAGAG GATGTGGAAT     7200

TACTAGAGAT GAAGCCTGGG TCTATTCCAT CTTCTATCTG CAGGAGGTAT GGAGTACATT     7260

CTTCAATACT GTGCACCAGC AAGGAGTACG GCTTGTTCTA CCTGCAGCAG GGGGACTCCG     7320

GATTACTTTC TATATTGGAG CAAAAGGAGT CAGGGGAGTT TGAAGAGATC CTGGACTTCA     7380

ATCTGAACTT AAATAATCCT AATGGGTCCC CAGTATCAAT CACTCAGGCC AAACCTGAGT     7440

CTGAATCATC CCTTTTGTGC GCCACCTCTG ATGGGATGCT GTGGAACTTA TCTGAATGTA     7500

CCTCAGAGGG AGAATGGATC GTAGATAACA TTTGGCAGAA AAAAGCAAAA AAACCTAAAA     7560

CTCAGACTCT GGAGACAGAG TTGTCCCCGC ACTCAGAGTT GGATTTTTCC ATTGATTGCT     7620

GGATTGATCC CACAAATTTA AAGGCACAGC AGTGTAAAAA GATCCACTTG GGCTCTGTCA     7680

CAGCCCTCCA TGTGCTTCCG GGATTGCTGG TGACAGCTTC GAAGGACAGA GATGTTAAGC     7740

TGTGGGAGAG ACCCAGTATG CAGCTGCTGG GCTTGTTCCG ATGTGAAGGG CCAGTGAGCT     7800

GTCTGGAACC TTGGATGGAG CCCAGCTCTC CCCTGCAGCT TGCTGTGGGA GACACACAAG     7860

GAAACTTGTA TTTTCTATCT TGGGAA                                          7886

(2) INFORMATION FOR SEQ ID NO:3:

(i) SEQUENCE CHARACTERISTICS:
        (A) LENGTH: 2627 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

Met Glu Lys Leu His Gly His Val Ser Ala His Pro Asp Ile Leu Ser
    1               5                   10                  15

Leu Glu Asn Arg Cys Leu Ala Met Leu Pro Asp Leu Gln Pro Leu Glu
                20                  25                  30

Lys Leu His Gln His Val Ser Thr His Ser Asp Ile Leu Ser Leu Lys
            35                  40                  45

Asn Gln Cys Leu Ala Thr Leu Pro Asp Leu Lys Thr Met Glu Lys Pro
        50                  55                  60

His Gly Tyr Val Ser Ala His Pro Asp Ile Leu Ser Leu Glu Asn Gln
    65                  70                  75                  80
```

```
Cys Leu Ala Thr Leu Ser Asp Leu Lys Thr Met Glu Lys Pro His Gly
                 85                  90                  95

His Val Ser Ala His Pro Asp Ile Leu Ser Leu Glu Asn Arg Cys Leu
                100                 105                 110

Ala Thr Leu Pro Ser Leu Lys Ser Thr Val Ser Ala Ser Pro Leu Phe
            115                 120                 125

Gln Ser Leu Gln Ile Ser His Met Thr Gln Ala Asp Leu Tyr Arg Val
        130                 135                 140

Asn Asn Ser Asn Cys Leu Leu Ser Glu Pro Pro Ser Trp Arg Ala Gln
145                 150                 155                 160

His Phe Ser Lys Gly Leu Asp Leu Ser Thr Cys Pro Ile Ala Leu Lys
                165                 170                 175

Ser Ile Ser Ala Thr Glu Thr Ala Gln Glu Ala Thr Leu Gly Arg Trp
            180                 185                 190

Phe Asp Ser Glu Glu Lys Lys Gly Ala Glu Thr Gln Met Pro Ser Tyr
        195                 200                 205

Ser Leu Ser Leu Gly Glu Glu Glu Val Glu Asp Leu Ala Val Lys
    210                 215                 220

Leu Thr Ser Gly Asp Ser Glu Ser His Pro Glu Pro Thr Asp His Val
225                 230                 235                 240

Leu Gln Glu Lys Lys Met Ala Leu Leu Ser Leu Leu Cys Ser Thr Leu
                245                 250                 255

Val Ser Glu Val Asn Met Asn Asn Thr Ser Asp Pro Thr Leu Ala Ala
            260                 265                 270

Ile Phe Glu Ile Cys Arg Glu Leu Ala Leu Leu Glu Pro Glu Phe Ile
        275                 280                 285

Leu Lys Ala Ser Leu Tyr Ala Arg Gln Gln Leu Asn Val Arg Asn Val
    290                 295                 300

Ala Asn Asn Ile Leu Ala Ile Ala Ala Phe Leu Pro Ala Cys Arg Pro
305                 310                 315                 320

His Leu Arg Arg Tyr Phe Cys Ala Ile Val Gln Leu Pro Ser Asp Trp
                325                 330                 335

Ile Gln Val Ala Glu Leu Tyr Gln Ser Leu Ala Glu Gly Asp Lys Asn
            340                 345                 350

Lys Leu Val Pro Leu Pro Ala Cys Leu Arg Thr Ala Met Thr Asp Lys
        355                 360                 365

Phe Ala Gln Phe Asp Glu Tyr Gln Leu Ala Lys Tyr Asn Pro Arg Lys
    370                 375                 380

His Arg Ala Lys Arg His Pro Arg Arg Pro Pro Arg Ser Pro Gly Met
385                 390                 395                 400

Glu Pro Pro Phe Ser His Arg Cys Phe Pro Arg Tyr Ile Gly Phe Leu
                405                 410                 415

Arg Glu Glu Gln Arg Lys Phe Glu Lys Ala Gly Asp Thr Val Ser Glu
            420                 425                 430

Lys Lys Asn Pro Pro Arg Phe Thr Leu Lys Lys Leu Val Gln Arg Leu
        435                 440                 445

His Ile His Lys Pro Ala Gln His Val Gln Ala Leu Leu Gly Tyr Arg
    450                 455                 460

Tyr Pro Ser Asn Leu Gln Leu Phe Ser Arg Ser Arg Leu Pro Gly Pro
465                 470                 475                 480

Trp Asp Ser Ser Arg Ala Gly Lys Arg Met Lys Leu Ser Arg Pro Glu
                485                 490                 495

Thr Trp Glu Arg Glu Leu Ser Leu Arg Gly Asn Lys Ala Ser Val Trp
            500                 505                 510
```

```
Glu Glu Leu Ile Glu Asn Gly Lys Leu Pro Phe Met Ala Met Leu Arg
            515                 520                 525

Asn Leu Cys Asn Leu Leu Arg Val Gly Ile Ser Ser Arg His His Glu
        530                 535                 540

Leu Ile Leu Gln Arg Leu Gln His Gly Lys Ser Val Ile His Ser Arg
545                 550                 555                 560

Gln Phe Pro Phe Arg Phe Leu Asn Ala His Asp Ala Ile Asp Ala Leu
                565                 570                 575

Glu Ala Gln Leu Arg Asn Gln Ala Leu Pro Phe Pro Ser Asn Ile Thr
            580                 585                 590

Leu Met Arg Arg Ile Leu Thr Arg Asn Glu Lys Asn Arg Pro Arg Arg
            595                 600                 605

Arg Phe Leu Cys His Leu Ser Arg Gln Gln Leu Arg Met Ala Met Arg
            610                 615                 620

Ile Pro Val Leu Tyr Glu Gln Leu Lys Arg Glu Lys Leu Arg Val His
625                 630                 635                 640

Lys Ala Arg Gln Trp Lys Tyr Asp Gly Glu Met Leu Asn Arg Tyr Arg
                645                 650                 655

Gln Ala Leu Glu Thr Ala Val Asn Leu Ser Val Lys His Ser Leu Pro
            660                 665                 670

Leu Leu Pro Gly Arg Thr Val Leu Val Tyr Leu Thr Asp Ala Asn Ala
            675                 680                 685

Asp Arg Leu Cys Pro Lys Ser Asn Pro Gln Gly Pro Pro Leu Asn Tyr
            690                 695                 700

Ala Leu Leu Leu Ile Gly Met Met Ile Thr Arg Ala Glu Gln Val Asp
705                 710                 715                 720

Val Val Leu Cys Gly Gly Asp Thr Leu Lys Thr Ala Val Leu Lys Ala
                725                 730                 735

Glu Glu Gly Ile Leu Lys Thr Ala Ile Lys Leu Gln Ala Gln Val Gln
            740                 745                 750

Glu Phe Asp Glu Asn Asp Gly Trp Ser Leu Asn Thr Phe Gly Lys Tyr
            755                 760                 765

Leu Leu Ser Leu Ala Gly Gln Arg Val Pro Val Asp Arg Val Ile Leu
770                 775                 780

Leu Gly Gln Ser Met Asp Asp Gly Met Ile Asn Val Ala Lys Gln Leu
785                 790                 795                 800

Tyr Trp Gln Arg Val Asn Ser Lys Cys Leu Phe Val Gly Ile Leu Leu
                805                 810                 815

Arg Arg Val Gln Tyr Leu Ser Thr Asp Leu Asn Pro Asn Asp Val Thr
            820                 825                 830

Leu Ser Gly Cys Thr Asp Ala Ile Leu Lys Phe Ile Ala Glu His Gly
            835                 840                 845

Ala Ser His Leu Leu Glu His Val Gly Gln Met Asp Lys Ile Phe Lys
            850                 855                 860

Ile Pro Pro Pro Gly Lys Thr Gly Val Gln Ser Leu Arg Pro Leu
865                 870                 875                 880

Glu Glu Asp Thr Pro Ser Pro Leu Ala Pro Val Ser Gln Gln Gly Trp
            885                 890                 895

Arg Ser Ile Arg Leu Phe Ile Ser Ser Thr Phe Arg Asp Met His Gly
                900                 905                 910

Glu Arg Asp Leu Leu Leu Arg Ser Val Leu Pro Ala Leu Gln Ala Arg
            915                 920                 925

Ala Ala Pro His Arg Ile Ser Leu His Gly Ile Asp Leu Arg Trp Gly
```

-continued

```
                930                 935                 940
Val Thr Glu Glu Glu Thr Arg Arg Asn Arg Gln Leu Glu Val Cys Leu
945                 950                 955                 960

Gly Glu Val Glu Asn Ala Gln Leu Phe Val Gly Ile Leu Gly Ser Arg
                965                 970                 975

Tyr Gly Tyr Ile Pro Pro Ser Tyr Asn Leu Pro Asp His Pro His Phe
                980                 985                 990

His Trp Ala Gln Gln Tyr Pro Ser Gly Arg Ser Val Thr Glu Met Glu
                995                 1000                1005

Val Met Gln Phe Leu Asn Arg Asn Gln Arg Leu Gln Pro Ser Ala Gln
                1010                1015                1020

Ala Leu Ile Tyr Phe Arg Asp Ser Ser Phe Leu Ser Val Pro Asp
1025                1030                1035                1040

Ala Trp Lys Ser Asp Phe Val Ser Glu Ser Glu Ala Ala Xaa Arg
                1045                1050                1055

Ile Ser Glu Leu Lys Ser Tyr Leu Ser Arg Gln Lys Gly Ile Thr Cys
                1060                1065                1070

Arg Arg Tyr Pro Cys Glu Trp Gly Gly Val Ala Ala Gly Arg Pro Tyr
                1075                1080                1085

Val Gly Gly Leu Glu Glu Phe Gly Gln Leu Val Leu Gln Asp Val Trp
1090                1095                1100

Asn Met Ile Gln Lys Leu Tyr Leu Gln Pro Gly Ala Leu Leu Glu Gln
1105                1110                1115                1120

Pro Val Ser Ile Pro Asp Asp Leu Val Gln Ala Thr Phe Gln Gln
                1125                1130                1135

Leu Gln Lys Pro Pro Ser Pro Ala Arg Pro Arg Leu Leu Gln Asp Thr
                1140                1145                1150

Val Gln Xaa Leu Met Leu Pro His Gly Arg Leu Ser Leu Val Thr Gly
                1155                1160                1165

Gln Ser Gly Gln Gly Lys Thr Ala Phe Leu Ala Ser Leu Val Ser Ala
                1170                1175                1180

Leu Gln Ala Pro Asp Gly Ala Lys Val Ala Xaa Leu Val Phe Phe His
1185                1190                1195                1200

Phe Ser Gly Ala Arg Pro Asp Gln Gly Leu Ala Leu Thr Leu Leu Arg
                1205                1210                1215

Arg Leu Cys Thr Tyr Leu Arg Gly Gln Leu Lys Glu Pro Gly Ala Leu
                1220                1225                1230

Pro Ser Thr Tyr Arg Ser Leu Val Trp Glu Leu Gln Gln Arg Leu Leu
                1235                1240                1245

Pro Lys Ser Ala Glu Ser Leu His Pro Gly Gln Thr Gln Val Leu Ile
                1250                1255                1260

Ile Asp Gly Ala Asp Arg Leu Val Asp Gln Asn Gly Gln Leu Ile Ser
1265                1270                1275                1280

Asp Trp Ile Pro Lys Lys Leu Pro Arg Cys Val His Leu Val Leu Ser
                1285                1290                1295

Val Ser Ser Asp Ala Gly Leu Gly Glu Thr Leu Glu Gln Ser Gln Gly
                1300                1305                1310

Ala His Val Leu Ala Leu Gly Pro Leu Glu Ala Ser Ala Arg Ala Arg
                1315                1320                1325

Leu Val Arg Glu Glu Leu Ala Leu Tyr Gly Lys Arg Leu Glu Glu Ser
                1330                1335                1340

Pro Phe Asn Asn Gln Met Arg Leu Leu Val Lys Arg Glu Ser Gly
1345                1350                1355                1360
```

```
Arg Pro Leu Tyr Leu Arg Leu Val Thr Asp His Leu Arg Leu Phe Thr
            1365                1370                1375

Leu Tyr Glu Gln Val Ser Glu Arg Leu Arg Thr Leu Pro Ala Thr Val
        1380                1385                1390

Pro Leu Leu Gln His Ile Leu Ser Thr Leu Glu Lys Glu His Gly
    1395                1400                1405

Pro Asp Val Leu Pro Gln Ala Leu Thr Ala Leu Glu Val Thr Arg Ser
    1410                1415                1420

Gly Leu Thr Val Asp Gln Leu His Gly Val Leu Ser Val Trp Arg Thr
1425                1430                1435                1440

Leu Pro Lys Gly Thr Lys Ser Trp Glu Glu Ala Val Ala Ala Gly Asn
        1445                1450                1455

Ser Gly Asp Pro Tyr Pro Met Gly Pro Phe Ala Cys Leu Val Gln Ser
            1460                1465                1470

Leu Arg Ser Leu Leu Gly Glu Gly Pro Leu Glu Arg Pro Gly Ala Arg
    1475                1480                1485

Leu Cys Leu Pro Asp Gly Pro Leu Arg Thr Ala Ala Lys Arg Cys Tyr
    1490                1495                1500

Gly Lys Arg Pro Gly Leu Glu Asp Thr Ala His Ile Leu Ile Ala Ala
1505                1510                1515                1520

Gln Leu Trp Lys Thr Cys Asp Ala Asp Ala Ser Gly Thr Phe Arg Ser
        1525                1530                1535

Cys Pro Pro Glu Ala Leu Gly Asp Leu Pro Tyr His Leu Leu Gln Ser
        1540                1545                1550

Gly Asn Arg Gly Leu Leu Ser Lys Phe Leu Thr Asn Leu His Val Val
        1555                1560                1565

Ala Ala His Leu Glu Leu Gly Leu Val Ser Arg Leu Leu Glu Ala His
    1570                1575                1580

Ala Leu Tyr Ala Ser Ser Val Pro Lys Glu Glu Gln Lys Leu Pro Glu
1585                1590                1595                1600

Ala Asp Val Ala Val Phe Arg Thr Phe Leu Arg Gln Gln Ala Ser Ile
        1605                1610                1615

Leu Ser Gln Tyr Pro Arg Leu Leu Pro Gln Gln Ala Ala Asn Gln Pro
        1620                1625                1630

Leu Asp Ser Pro Leu Cys His Gln Ala Ser Leu Leu Ser Arg Arg Trp
        1635                1640                1645

His Leu Gln His Thr Leu Arg Trp Leu Asn Lys Pro Arg Thr Met Lys
        1650                1655                1660

Asn Gln Gln Ser Ser Ser Leu Ser Leu Ala Val Ser Ser Ser Pro Thr
1665                1670                1675                1680

Ala Val Ala Phe Ser Thr Asn Gly Gln Arg Ala Ala Val Gly Thr Ala
            1685                1690                1695

Asn Gly Thr Val Tyr Leu Leu Asp Leu Arg Thr Trp Gln Glu Glu Lys
            1700                1705                1710

Ser Val Val Ser Gly Cys Asp Gly Ile Ser Ala Cys Leu Phe Leu Ser
            1715                1720                1725

Asp Asp Thr Leu Phe Leu Thr Ala Phe Asp Gly Leu Leu Glu Leu Trp
        1730                1735                1740

Asp Leu Gln His Gly Cys Arg Val Leu Gln Thr Lys Ala His Gln Tyr
1745                1750                1755                1760

Gln Ile Thr Gly Cys Cys Leu Ser Pro Asp Cys Arg Leu Leu Ala Thr
            1765                1770                1775

Val Cys Leu Gly Gly Cys Leu Lys Leu Trp Asp Thr Val Arg Gly Gln
        1780                1785                1790
```

-continued

Leu Ala Phe Gln His Thr Tyr Pro Lys Ser Leu Asn Cys Val Ala Phe
    1795                1800                1805

His Pro Glu Gly Gln Val Ile Ala Thr Gly Ser Trp Ala Gly Ser Ile
    1810                1815                1820

Ser Phe Phe Gln Val Asp Gly Leu Lys Val Thr Lys Asp Leu Gly Ala
1825                1830                1835                1840

Pro Gly Ala Ser Ile Arg Thr Leu Ala Phe Asn Val Pro Gly Gly Val
                1845                1850                1855

Val Ala Val Gly Arg Leu Asp Ser Met Val Glu Leu Trp Ala Trp Arg
            1860                1865                1870

Glu Gly Ala Arg Leu Ala Ala Phe Pro Ala His His Gly Phe Val Ala
        1875                1880                1885

Ala Ala Leu Phe Leu His Ala Gly Cys Gln Leu Leu Thr Ala Gly Glu
    1890                1895                1900

Asp Gly Lys Val Gln Val Trp Ser Gly Ser Leu Gly Arg Pro Arg Gly
1905                1910                1915                1920

His Leu Gly Ser Leu Ser Leu Ser Pro Ala Leu Ser Val Ala Leu Ser
                1925                1930                1935

Pro Asp Gly Asp Arg Val Ala Val Gly Tyr Arg Ala Asp Gly Ile Arg
            1940                1945                1950

Ile Tyr Lys Ile Ser Ser Gly Ser Gln Gly Ala Gln Gly Gln Ala Leu
        1955                1960                1965

Asp Val Ala Val Ser Ala Leu Ala Trp Leu Ser Pro Lys Val Leu Val
    1970                1975                1980

Ser Gly Ala Glu Asp Gly Ser Leu Gln Gly Trp Ala Leu Lys Glu Cys
1985                1990                1995                2000

Ser Leu Gln Ser Leu Trp Leu Leu Ser Arg Phe Gln Lys Pro Val Leu
                2005                2010                2015

Gly Leu Ala Thr Ser Gln Glu Leu Leu Ala Ser Ala Ser Glu Asp Phe
            2020                2025                2030

Thr Val Gln Leu Trp Pro Arg Gln Leu Leu Thr Arg Pro His Lys Ala
        2035                2040                2045

Glu Asp Phe Pro Cys Gly Thr Glu Leu Arg Gly His Glu Gly Pro Val
    2050                2055                2060

Ser Cys Cys Ser Phe Ser Thr Asp Gly Gly Ser Leu Ala Thr Gly Gly
2065                2070                2075                2080

Arg Asp Arg Ser Leu Leu Cys Trp Asp Val Arg Thr Pro Lys Thr Pro
                2085                2090                2095

Val Leu Ile His Ser Phe Pro Ala Cys His Arg Asp Trp Val Thr Gly
            2100                2105                2110

Cys Ala Trp Thr Lys Asp Asn Leu Leu Ile Ser Cys Ser Ser Asp Gly
        2115                2120                2125

Ser Val Gly Leu Trp Asp Pro Glu Ser Gly Gln Arg Leu Gly Gln Phe
    2130                2135                2140

Leu Gly His Gln Ser Ala Val Ser Ala Val Ala Ala Val Glu Glu His
2145                2150                2155                2160

Val Val Ser Val Ser Arg Asp Gly Thr Leu Lys Val Trp Asp His Gln
                2165                2170                2175

Gly Val Glu Leu Thr Ser Ile Pro Ala His Ser Gly Pro Ile Ser His
            2180                2185                2190

Cys Ala Ala Ala Met Glu Pro Arg Ala Ala Gly Gln Pro Gly Ser Glu
        2195                2200                2205

Leu Leu Val Val Thr Val Gly Leu Asp Gly Ala Thr Arg Leu Trp His

```
                 2210                2215                2220
Pro Leu Leu Val Cys Gln Thr His Thr Leu Leu Gly His Ser Gly Pro
2225                2230                2235                2240

Val Arg Ala Ala Ala Val Ser Glu Thr Ser Gly Leu Met Leu Thr Ala
                2245                2250                2255

Ser Glu Asp Gly Ser Val Arg Leu Trp Gln Val Pro Lys Glu Ala Asp
                2260                2265                2270

Asp Thr Cys Ile Pro Arg Ser Ser Ala Ala Val Thr Ala Val Ala Trp
                2275                2280                2285

Ala Pro Asp Gly Ser Met Ala Val Ser Gly Asn Gln Ala Gly Glu Leu
                2290                2295                2300

Ile Leu Trp Gln Glu Ala Lys Ala Val Ala Thr Ala Gln Ala Pro Gly
2305                2310                2315                2320

His Ile Gly Ala Leu Ile Trp Ser Ser Ala His Thr Phe Phe Val Leu
                2325                2330                2335

Ser Ala Asp Glu Lys Ile Ser Glu Trp Gln Val Lys Leu Arg Lys Gly
                2340                2345                2350

Ser Ala Pro Gly Asn Leu Ser Leu His Leu Asn Arg Ile Leu Gln Glu
                2355                2360                2365

Asp Leu Gly Val Leu Thr Ser Leu Asp Trp Ala Pro Asp Gly His Phe
                2370                2375                2380

Leu Ile Leu Ala Lys Ala Asp Leu Lys Leu Leu Cys Met Lys Pro Gly
2385                2390                2395                2400

Asp Ala Pro Ser Glu Ile Trp Ser Ser Tyr Thr Glu Asn Pro Met Ile
                2405                2410                2415

Leu Ser Thr His Lys Glu Tyr Gly Ile Phe Val Leu Gln Pro Lys Asp
                2420                2425                2430

Pro Gly Val Leu Ser Phe Leu Arg Gln Lys Glu Ser Gly Glu Phe Glu
                2435                2440                2445

Glu Arg Leu Asn Phe Asp Ile Asn Leu Glu Asn Pro Ser Arg Thr Leu
                2450                2455                2460

Ile Ser Ile Thr Gln Ala Lys Pro Glu Ser Glu Ser Ser Phe Leu Cys
2465                2470                2475                2480

Ala Ser Ser Asp Gly Ile Leu Trp Asn Leu Ala Lys Cys Ser Pro Glu
                2485                2490                2495

Gly Glu Trp Thr Thr Gly Asn Met Trp Gln Lys Lys Ala Asn Thr Pro
                2500                2505                2510

Glu Thr Gln Thr Pro Gly Thr Asp Pro Ser Thr Cys Arg Glu Ser Asp
                2515                2520                2525

Ala Ser Met Asp Ser Asp Ala Ser Met Asp Ser Glu Pro Thr Pro His
                2530                2535                2540

Leu Lys Thr Arg Gln Arg Arg Lys Ile His Ser Gly Ser Val Thr Ala
2545                2550                2555                2560

Leu His Val Leu Pro Glu Leu Leu Val Thr Ala Ser Lys Asp Arg Asp
                2565                2570                2575

Val Lys Leu Trp Glu Arg Pro Ser Met Gln Leu Leu Gly Leu Phe Arg
                2580                2585                2590

Cys Glu Gly Ser Val Ser Cys Leu Glu Pro Trp Leu Gly Ala Asn Ser
                2595                2600                2605

Thr Leu Gln Leu Ala Val Gly Asp Val Gln Gly Asn Val Tyr Phe Leu
                2610                2615                2620

Asn Trp Glu
2625
```

(2) INFORMATION FOR SEQ ID NO:4:

(i) SEQUENCE CHARACTERISTICS:
        (A) LENGTH: 2629 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:4:

```
Met Glu Lys Leu Cys Gly His Val Pro Gly His Ser Asp Ile Leu Ser
 1               5                  10                  15

Leu Lys Asn Arg Cys Leu Thr Met Leu Pro Asp Leu Gln Pro Leu Glu
             20                  25                  30

Lys Ile His Gly His Arg Ser Val His Ser Asp Ile Leu Ser Leu Glu
         35                  40                  45

Asn Gln Cys Leu Thr Met Leu Ser Asp Leu Gln Pro Thr Glu Arg Ile
     50                  55                  60

Asp Gly His Ile Ser Val His Pro Asp Ile Leu Ser Leu Glu Asn Arg
 65                  70                  75                  80

Cys Leu Thr Met Leu Pro Asp Leu Gln Pro Leu Glu Lys Leu Cys Gly
                 85                  90                  95

His Met Ser Ser His Pro Asp Val Leu Ser Leu Glu Asn Gln Cys Leu
            100                 105                 110

Ala Thr Leu Pro Thr Val Lys Ser Thr Ala Leu Thr Ser Pro Leu Leu
        115                 120                 125

Gln Gly Leu His Ile Ser His Thr Ala Gln Ala Asp Leu His Ser Leu
    130                 135                 140

Lys Thr Ser Asn Cys Leu Leu Pro Glu Leu Pro Thr Lys Lys Thr Pro
145                 150                 155                 160

Cys Phe Ser Glu Glu Leu Asp Leu Pro Pro Gly Pro Arg Ala Leu Lys
                165                 170                 175

Ser Met Ser Ala Thr Ala Gln Val Gln Glu Val Ala Leu Gly Gln Trp
            180                 185                 190

Cys Val Ser Lys Glu Lys Glu Phe Gln Glu Glu Ser Thr Glu Val
        195                 200                 205

Pro Met Pro Leu Tyr Ser Leu Ser Leu Glu Glu Glu Val Glu Ala
    210                 215                 220

Pro Val Leu Lys Leu Thr Ser Gly Asp Ser Gly Phe His Pro Glu Thr
225                 230                 235                 240

Thr Asp Gln Val Leu Gln Glu Lys Lys Met Ala Leu Leu Thr Leu Leu
                245                 250                 255

Cys Ser Ala Leu Ala Ser Asn Val Asn Val Lys Asp Ala Ser Asp Leu
            260                 265                 270

Thr Arg Ala Ser Ile Leu Glu Val Cys Ser Ala Leu Ala Ser Leu Glu
        275                 280                 285

Pro Glu Phe Ile Leu Lys Ala Ser Leu Tyr Ala Arg Gln Gln Leu Asn
    290                 295                 300

Leu Arg Asp Ile Ala Asn Thr Val Leu Ala Val Ala Ala Leu Leu Pro
305                 310                 315                 320

Ala Cys Arg Pro His Val Arg Arg Tyr Tyr Ser Ala Ile Val His Leu
                325                 330                 335

Pro Ser Asp Trp Ile Gln Val Ala Glu Phe Tyr Gln Ser Leu Ala Glu
            340                 345                 350

Gly Asp Glu Lys Lys Leu Val Ser Leu Pro Ala Cys Leu Arg Ala Ala
```

```
                355                 360                 365
Met Thr Asp Lys Phe Ala Glu Phe Asp Glu Tyr Gln Leu Ala Lys Tyr
            370                 375                 380
Asn Pro Arg Lys His Arg Ser Lys Arg Ser Arg Gln Pro Pro Arg
385                 390                 395                 400
Pro Gln Lys Thr Glu Arg Pro Phe Ser Glu Arg Gly Lys Cys Phe Pro
                405                 410                 415
Lys Ser Leu Trp Pro Leu Lys Asn Glu Gln Ile Thr Phe Glu Ala Ala
            420                 425                 430
Tyr Asn Ala Met Pro Glu Lys Asn Arg Leu Pro Arg Phe Thr Leu Lys
                435                 440                 445
Lys Leu Val Glu Tyr Leu His Ile His Lys Pro Ala Gln His Val Gln
450                 455                 460
Ala Leu Leu Gly Tyr Arg Tyr Pro Ala Thr Leu Glu Leu Phe Ser Arg
465                 470                 475                 480
Ser His Leu Pro Gly Pro Trp Glu Ser Ser Arg Ala Gly Gln Arg Met
                485                 490                 495
Lys Leu Arg Arg Pro Glu Thr Trp Glu Arg Glu Leu Ser Leu Arg Gly
                500                 505                 510
Asn Lys Ala Ser Val Trp Glu Glu Leu Ile Asp Asn Gly Lys Leu Pro
            515                 520                 525
Phe Met Ala Met Leu Arg Asn Leu Cys Asn Leu Leu Arg Thr Gly Ile
            530                 535                 540
Ser Ala Arg His His Glu Leu Val Leu Gln Arg Leu Gln His Glu Lys
545                 550                 555                 560
Ser Val Val His Ser Arg Gln Phe Pro Phe Arg Phe Leu Asn Ala His
                565                 570                 575
Asp Ser Ile Asp Lys Leu Glu Ala Gln Leu Arg Ser Lys Ala Ser Pro
            580                 585                 590
Phe Pro Ser Asn Thr Thr Leu Met Lys Arg Ile Met Ile Arg Asn Ser
            595                 600                 605
Lys Lys Asn Arg Arg Pro Ala Ser Arg Lys His Leu Cys Thr Leu Thr
610                 615                 620
Arg Arg Gln Leu Arg Ala Ala Met Thr Ile Pro Val Met Tyr Glu Gln
625                 630                 635                 640
Leu Lys Arg Glu Lys Leu Arg Leu His Lys Ala Arg Gln Trp Asn Cys
                645                 650                 655
Asp Val Glu Leu Leu Glu Arg Tyr Arg Gln Ala Leu Glu Thr Ala Val
                660                 665                 670
Asn Leu Ser Val Lys His Asn Leu Ser Pro Met Pro Gly Arg Thr Leu
            675                 680                 685
Leu Val Tyr Leu Thr Asp Ala Asn Ala Asp Arg Leu Cys Pro Lys Ser
            690                 695                 700
His Ser Gln Gly Pro Pro Leu Asn Tyr Val Leu Leu Ile Gly Met
705                 710                 715                 720
Met Val Ala Arg Ala Glu Gln Val Thr Val Cys Leu Cys Gly Gly Gly
                725                 730                 735
Phe Val Lys Thr Pro Val Leu Thr Ala Asp Glu Gly Ile Leu Lys Thr
                740                 745                 750
Ala Ile Lys Leu Gln Ala Gln Val Gln Glu Leu Glu Gly Asn Asp Glu
                755                 760                 765
Trp Pro Leu Asp Thr Phe Gly Lys Tyr Leu Leu Ser Leu Ala Val Gln
            770                 775                 780
```

```
Arg Thr Pro Ile Asp Arg Val Ile Leu Phe Gly Gln Arg Met Asp Thr
785                 790                 795                 800

Glu Leu Leu Lys Val Ala Lys Gln Ile Ile Trp Gln His Val Asn Ser
            805                 810                 815

Lys Cys Leu Phe Val Gly Val Leu Leu Gln Lys Thr Gln Tyr Ile Ser
                820                 825                 830

Pro Asn Leu Asn Pro Asn Asp Val Thr Leu Ser Gly Cys Thr Asp Gly
            835                 840                 845

Ile Leu Lys Phe Ile Ala Glu His Gly Ala Ser Arg Leu Leu Glu His
        850                 855                 860

Val Gly Gln Leu Asp Lys Leu Phe Lys Ile Pro Pro Pro Gly Lys
865                 870                 875                 880

Thr Gln Ala Pro Ser Leu Arg Pro Leu Glu Glu Asn Ile Pro Gly Pro
                885                 890                 895

Leu Gly Pro Ile Ser Gln His Gly Trp Arg Asn Ile Arg Leu Phe Ile
            900                 905                 910

Ser Ser Thr Phe Arg Asp Met His Gly Glu Arg Asp Leu Leu Met Arg
        915                 920                 925

Ser Val Leu Pro Ala Leu Gln Ala Arg Val Phe Pro His Arg Ile Ser
930                 935                 940

Leu His Ala Ile Asp Leu Arg Trp Gly Ile Thr Glu Glu Thr Arg
945                 950                 955                 960

Arg Asn Arg Gln Leu Glu Val Cys Leu Gly Glu Val Glu Asn Ser Gln
                965                 970                 975

Leu Phe Val Gly Ile Leu Gly Ser Arg Tyr Gly Tyr Ile Pro Pro Ser
            980                 985                 990

Tyr Asp Leu Pro Asp His Pro His Phe His Trp Thr His Glu Tyr Pro
        995                 1000                1005

Ser Gly Arg Ser Val Thr Glu Met Glu Val Met Gln Phe Leu Asn Arg
1010                1015                1020

Gly Gln Arg Ser Gln Pro Ser Ala Gln Ala Leu Ile Tyr Phe Arg Asp
1025                1030                1035                1040

Pro Asp Phe Leu Ser Ser Val Pro Asp Ala Trp Lys Pro Asp Phe Ile
                1045                1050                1055

Ser Glu Ser Glu Glu Ala Ala His Arg Val Ser Glu Leu Lys Arg Tyr
            1060                1065                1070

Leu His Glu Gln Lys Glu Val Thr Cys Arg Ser Tyr Ser Cys Glu Trp
        1075                1080                1085

Gly Gly Val Ala Ala Gly Arg Pro Tyr Thr Gly Gly Leu Glu Glu Phe
1090                1095                1100

Gly Gln Leu Val Leu Gln Asp Val Trp Ser Met Ile Gln Lys Gln His
1105                1110                1115                1120

Leu Gln Pro Gly Ala Gln Leu Glu Gln Pro Thr Ser Ile Ser Glu Asp
                1125                1130                1135

Asp Leu Ile Gln Thr Ser Phe Gln Gln Leu Lys Thr Pro Thr Ser Pro
            1140                1145                1150

Ala Arg Pro Arg Leu Leu Gln Asp Thr Val Gln Gln Leu Leu Leu Pro
        1155                1160                1165

His Gly Arg Leu Ser Leu Val Thr Gly Gln Ala Gly Gln Gly Lys Thr
        1170                1175                1180

Ala Phe Leu Ala Ser Leu Val Ser Ala Leu Lys Val Pro Asp Gln Pro
1185                1190                1195                1200

Asn Glu Pro Pro Phe Val Phe His Phe Ala Ala Ala Arg Pro Asp
                1205                1210                1215
```

```
Gln Cys Leu Ala Leu Asn Leu Leu Arg Arg Leu Cys Thr His Leu Arg
            1220                1225                1230

Gln Lys Leu Gly Glu Leu Ser Ala Leu Pro Ser Thr Tyr Arg Gly Leu
        1235                1240                1245

Val Trp Glu Leu Gln Gln Lys Leu Leu Leu Lys Phe Ala Gln Ser Leu
    1250                1255                1260

Gln Pro Ala Gln Thr Leu Val Leu Ile Ile Asp Gly Ala Asp Lys Leu
1265                1270                1275                1280

Val Asp Arg Asn Gly Gln Leu Ile Ser Asp Trp Ile Pro Lys Ser Leu
                1285                1290                1295

Pro Arg Arg Val His Leu Val Leu Ser Val Ser Ser Asp Ser Gly Leu
                    1300                1305                1310

Gly Glu Thr Leu Gln Gln Ser Gln Gly Ala Tyr Val Ala Leu Gly
        1315                1320                1325

Ser Leu Val Pro Ser Ser Arg Ala Gln Leu Val Arg Glu Glu Leu Ala
    1330                1335                1340

Leu Tyr Gly Lys Arg Leu Glu Glu Ser Pro Phe Asn Asn Gln Met Arg
1345                1350                1355                1360

Leu Leu Leu Ala Lys Gln Gly Ser Ser Leu Pro Leu Tyr Leu His Leu
                1365                1370                1375

Val Thr Asp Tyr Leu Arg Leu Phe Thr Leu Tyr Glu Gln Val Ser Glu
    1380                1385                1390

Arg Leu Arg Thr Leu Pro Ala Thr Leu Pro Leu Leu Gln His Ile
        1395                1400                1405

Leu Ser Thr Leu Glu Gln Glu His Gly His Asp Val Leu Pro Gln Ala
    1410                1415                1420

Leu Thr Ala Leu Glu Val Thr Arg Ser Gly Leu Thr Val Asp Gln Leu
1425                1430                1435                1440

His Ala Ile Leu Ser Thr Trp Leu Ile Leu Pro Lys Glu Thr Lys Ser
                1445                1450                1455

Trp Glu Glu Val Leu Ala Ala Ser His Ser Gly Asn Pro Phe Pro Leu
                1460                1465                1470

Cys Pro Phe Ala Tyr Leu Val Gln Ser Leu Arg Ser Leu Leu Gly Glu
                1475                1480                1485

Gly Pro Val Glu Arg Pro Gly Ala Arg Leu Cys Leu Ser Asp Gly Pro
        1490                1495                1500

Leu Arg Thr Thr Ile Lys Arg Arg Tyr Gly Lys Arg Leu Gly Leu Glu
1505                1510                1515                1520

Lys Thr Ala His Val Leu Ile Ala Ala His Leu Trp Lys Thr Cys Asp
                1525                1530                1535

Pro Asp Ala Ser Gly Thr Phe Arg Ser Cys Pro Pro Glu Ala Leu Lys
                1540                1545                1550

Asp Leu Pro Tyr His Leu Leu Gln Ser Gly Asn His Gly Leu Leu Ala
            1555                1560                1565

Glu Phe Leu Thr Asn Leu His Val Val Ala Ala Tyr Leu Glu Val Gly
        1570                1575                1580

Leu Val Pro Asp Leu Leu Glu Ala His Val Leu Tyr Ala Ser Ser Lys
1585                1590                1595                1600

Pro Glu Ala Asn Gln Lys Leu Pro Ala Ala Asp Val Ala Val Phe His
                1605                1610                1615

Thr Phe Leu Arg Gln Gln Ala Ser Leu Leu Thr Gln Tyr Pro Leu Leu
            1620                1625                1630

Leu Leu Gln Gln Ala Ala Ser Gln Pro Glu Glu Ser Pro Val Cys Cys
```

-continued

```
                1635                1640                1645

Gln Ala Pro Leu Leu Thr Gln Arg Trp His Asp Gln Phe Thr Leu Lys
       1650                1655                1660

Trp Ile Asn Lys Pro Gln Thr Leu Lys Gly Gln Gln Ser Leu Ser Leu
    1665                1670                1675                1680

Thr Met Ser Ser Pro Thr Ala Val Ala Phe Ser Pro Asn Gly Gln
                1685                1690                1695

Arg Ala Ala Val Gly Thr Ala Ser Gly Thr Ile Tyr Leu Leu Asn Leu
                   1700                1705                1710

Lys Thr Trp Gln Glu Lys Ala Val Val Ser Gly Cys Asp Gly Ile
           1715                1720                1725

Ser Ser Phe Ala Phe Leu Ser Asp Thr Ala Leu Phe Leu Thr Thr Phe
       1730                1735                1740

Asp Gly His Leu Glu Leu Trp Asp Leu Gln His Gly Cys Trp Val Phe
    1745                1750                1755                1760

Gln Thr Lys Ala His Gln Tyr Gln Ile Thr Gly Cys Cys Leu Ser Pro
               1765                1770                1775

Asp Arg Arg Leu Leu Ala Thr Val Cys Leu Gly Gly Tyr Leu Lys Leu
               1780                1785                1790

Trp Asp Thr Val Arg Gly Gln Leu Ala Phe Gln Tyr Thr His Pro Lys
               1795                1800                1805

Ser Leu Asn Cys Val Ala Phe His Pro Glu Gly Gln Val Val Ala Thr
       1810                1815                1820

Gly Ser Trp Ala Gly Ser Ile Thr Phe Phe Gln Ala Asp Gly Leu Lys
    1825                1830                1835                1840

Val Thr Lys Glu Leu Gly Ala Pro Gly Pro Ser Val Cys Ser Leu Ala
               1845                1850                1855

Phe Asn Lys Pro Gly Lys Ile Val Ala Val Gly Arg Ile Asp Gly Thr
               1860                1865                1870

Val Glu Leu Trp Ala Trp Gln Glu Gly Ala Arg Leu Ala Ala Phe Pro
               1875                1880                1885

Ala Gln Cys Gly Cys Val Ser Ala Val Leu Phe Leu His Ala Gly Asp
               1890                1895                1900

Arg Phe Leu Thr Ala Gly Glu Asp Gly Lys Ala Gln Leu Trp Ser Gly
    1905                1910                1915                1920

Phe Leu Gly Arg Pro Arg Gly Cys Leu Gly Ser Leu Pro Leu Ser Pro
               1925                1930                1935

Ala Leu Ser Val Ala Leu Asn Pro Asp Gly Asp Gln Val Ala Val Gly
               1940                1945                1950

Tyr Arg Glu Asp Gly Ile Asn Ile Tyr Lys Ile Ser Ser Gly Ser Gln
               1955                1960                1965

Gly Pro Gln His Gln Glu Leu Asn Val Ala Val Ser Ala Leu Val Trp
       1970                1975                1980

Leu Ser Pro Ser Val Leu Val Ser Gly Ala Glu Asp Gly Ser Leu His
    1985                1990                1995                2000

Gly Trp Met Phe Lys Gly Asp Ser Leu His Ser Leu Trp Leu Leu Ser
               2005                2010                2015

Arg Tyr Gln Lys Pro Val Leu Gly Leu Ala Ala Ser Arg Glu Leu Met
               2020                2025                2030

Ala Ala Ala Ser Glu Asp Phe Thr Val Arg Leu Trp Pro Arg Gln Leu
               2035                2040                2045

Leu Thr Gln Pro His Val His Ala Val Glu Leu Pro Cys Cys Ala Glu
               2050                2055                2060
```

```
Leu Arg Gly His Glu Gly Pro Val Cys Cys Cys Ser Phe Ser Pro Asp
2065                2070                2075                2080

Gly Gly Ile Leu Ala Thr Ala Gly Arg Asp Arg Asn Leu Leu Cys Trp
            2085                2090                2095

Asp Met Lys Ile Ala Gln Ala Pro Leu Leu Ile His Thr Phe Ser Ser
        2100                2105                2110

Cys His Arg Asp Trp Ile Thr Gly Cys Ala Trp Thr Lys Asp Asn Ile
    2115                2120                2125

Leu Val Ser Cys Ser Ser Asp Gly Ser Val Gly Leu Trp Asn Pro Glu
2130                2135                2140

Ala Gly Gln Gln Leu Gly Gln Phe Ser Gly His Gln Ser Ala Val Ser
2145                2150                2155                2160

Ala Val Val Ala Val Glu Glu His Ile Val Ser Val Ser Arg Asp Gly
                2165                2170                2175

Thr Leu Lys Val Trp Asp His Gln Gly Val Glu Leu Thr Ser Ile Pro
            2180                2185                2190

Ala His Ser Gly Pro Ile Ser Gln Cys Ala Ala Ala Leu Glu Pro Arg
        2195                2200                2205

Pro Gly Gly Gln Pro Gly Ser Glu Leu Leu Val Val Thr Val Gly Leu
    2210                2215                2220

Asp Gly Ala Thr Lys Leu Trp His Pro Leu Leu Val Cys Gln Ile Arg
2225                2230                2235                2240

Thr Leu Gln Gly His Ser Gly Pro Val Thr Ala Ala Ala Ala Ser Glu
                2245                2250                2255

Ala Ser Gly Leu Leu Leu Thr Ser Asp Asp Ser Ser Val Gln Leu Trp
            2260                2265                2270

Gln Ile Pro Lys Glu Ala Asp Asp Ser Tyr Lys Pro Arg Ser Ser Val
        2275                2280                2285

Ala Ile Thr Ala Val Ala Trp Ala Pro Asp Gly Ser Met Val Val Ser
    2290                2295                2300

Gly Asn Glu Ala Gly Glu Leu Thr Leu Trp Gln Gln Ala Lys Ala Val
2305                2310                2315                2320

Ala Thr Ala Gln Ala Pro Gly Arg Val Ser His Leu Ile Trp Tyr Ser
                2325                2330                2335

Ala Asn Ser Phe Phe Val Leu Ser Ala Asn Glu Asn Val Ser Glu Trp
            2340                2345                2350

Gln Val Gly Leu Arg Lys Gly Ser Thr Ser Thr Ser Ser Ser Leu His
        2355                2360                2365

Leu Lys Arg Val Leu Gln Glu Asp Trp Gly Val Leu Thr Gly Leu Gly
    2370                2375                2380

Leu Ala Pro Asp Gly Gln Ser Leu Ile Leu Met Lys Glu Asp Val Glu
2385                2390                2395                2400

Leu Leu Glu Met Lys Pro Gly Ser Ile Pro Ser Ser Ile Cys Arg Arg
                2405                2410                2415

Tyr Gly Val His Ser Ser Ile Leu Cys Thr Ser Lys Glu Tyr Gly Leu
            2420                2425                2430

Phe Tyr Leu Gln Gln Gly Asp Ser Gly Leu Leu Ser Ile Leu Glu Gln
        2435                2440                2445

Lys Glu Ser Gly Glu Phe Glu Glu Ile Leu Asp Phe Asn Leu Asn Leu
    2450                2455                2460

Asn Asn Pro Asn Gly Ser Pro Val Ser Ile Thr Gln Ala Lys Pro Glu
2465                2470                2475                2480

Ser Glu Ser Ser Leu Leu Cys Ala Thr Ser Asp Gly Met Leu Trp Asn
                2485                2490                2495
```

```
      Leu Ser Glu Cys Thr Ser Glu Gly Trp Ile Val Asp Asn Ile Trp
              2500                2505                2510

Gln Lys Lys Ala Lys Pro Lys Thr Gln Thr Leu Glu Thr Glu Leu
              2515                2520                2525

Ser Pro His Ser Glu Leu Asp Phe Ser Ile Asp Cys Trp Ile Asp Pro
              2530                2535                2540

Thr Asn Leu Lys Ala Gln Gln Cys Lys Lys Ile His Leu Gly Ser Val
      2545                2550                2555                2560

Thr Ala Leu His Val Leu Pro Gly Leu Leu Val Thr Ala Ser Lys Asp
                      2565                2570                2575

Arg Asp Val Lys Leu Trp Glu Arg Pro Ser Met Gln Leu Leu Gly Leu
              2580                2585                2590

Phe Arg Cys Glu Gly Pro Val Ser Cys Leu Glu Pro Trp Met Glu Pro
              2595                2600                2605

Ser Ser Pro Leu Gln Leu Ala Val Gly Asp Thr Gln Gly Asn Leu Tyr
              2610                2615                2620

Phe Leu Ser Trp Glu
      2625
```

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:5:

CCTCTGCGGC CGCTACANNN NNNNNT                                        26

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:6:

GGAGACGCCG GCGA                                                          14

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:7:

TCGACCCACG CGTCCG                                                     16

(2) INFORMATION FOR SEQ ID NO:8:

(i) SEQUENCE CHARACTERISTICS:

(A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:8:

GGGTGCGCAG GC                                                            12

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:9:

TGTAAAACGA CGGCCAGT                                                      18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:10:

CAGGAAACAG CTATGACC                                                      18

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:11:

CAATTAACCC TCACTAAAG                                                     19

(2) INFORMATION FOR SEQ ID NO:12:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo nucleotide"

(xi) SEQUENCE DESCRIPTION: SEQ ID NO:12:

GGTACCGCCA GCCGAGCCAC ATCGCTCAGA CACCATGATC GCAAATGTGA ATATTGCTCA         60

GGAACAAAAG CTTATTTCTG AAGAAGACTT GGCTCAGGAA CAAAAGCTTA TTTCTGAAGA        120

AGACTTGGCT CAGCAGAGTG GCGGAGGACT CGAG                                    154

GENES ENCODING TELOMERASE PROTEIN 1

FIELD OF THE INVENTION

This invention relates to novel genes encoding polypeptides that comprise a component of the telomerase enzyme complex, as well as to methods of making the genes and polypeptides.

BACKGROUND

RELATED ART

Many physiological changes occur as humans age. In addition to those observed at the phenotypic level such as change in hair color, appearance of skin, decreased lean body mass, etc., there are many changes at the cellular and biochemical levels. One such change that has been observed is a marked decrease in the length of telomeres in somatic cells as they age (Harley et al., Nature, 345:458–460 [1990]). Telomeres are repetitive DNA sequences that are localized to the ends of every chromosome, and are necessary for proper chromosome maintenance, replication, and localization of the chromosomes within the cell nucleus.

In most organisms, telomeres are synthesized and maintained by an enzyme known as telomerase. Telomerase is a ribonucleoprotein composed of RNA and protein components, and both types of components are necessary for activity (see for example, Greider, Annu. Rev. Biochem., 65:337–365 [1996]; Greider et al., in Cellular Aging and Cell Death, Wiley-Liss Inc., New York, N.Y., pp. 123–138 [1996]).

Most cells of adult humans do not have telomerase activity; exceptions include, for example, germline tissues (sperm cells and oocytes) and certain blood cells (Greider et al., Cellular Aging and Cell Death, supra). Decreased telomere length correlates well with decreased replicative capacity of cells in culture (referred to as cellular senescence or cell age). It has been postulated that shortened telomeres may be involved in the inability of cells to continue dividing (Harley, supra; Levy et al., J. Mol. Biol., 225:951–960 [1992]; and Harley et al., Cold Spring Harbor Symposium on Quantitative Biology, 59:307–315 [1994]), thereby contributing to senescence of the cells.

Recently, it has been shown that the telomeres of one class of white blood cells, called CD28−/CD8+ T-cells, are significantly shorter in AIDS patients as compared with the same cells obtained from healthy persons of the same or similar age (Effros et al., AIDS, 10:17–22 [1996]).

In many human cancerous cells, it has been shown that telomere length does not decrease, and telomerase activity is present, regardless of the age of these cells (Kim et al., Science, 266:2011–2015 [1994]; and Counter et al., EMBO J., 11:1921–1929 [1992]). It has been suggested that inhibition of telomerase in cancer cells might serve to decrease the proliferation of these cells (Harley et al., Cold Spring Harbor Symposium on Quantitative Biology, supra; and Greider et al., Cellular Aging and Cell Death, supra).

The RNA component of telomerase in several mammals has been cloned and sequenced (see PCT patent application WO 96/01835, published Jan. 25, 1995; Blasco et al., Science, 269:1267–1270 [1995]; Feng et al., Science, 269:1236–1241 [1995]), and it has been demonstrated that this RNA component is necessary for telomerase activity (Blasco et al., supra; Feng et al., supra; oral presentations at Cold Spring Harbor Laboratory Conference on Telomeres and Telomerase, Nov. 3–6, 1996). In mouse tumor models, an increase in telomerase RNA correlates with increased tumor progression (Blasco et al., Nature Genetics, 12:200–204 [1996]). However, Avilion et al. (Cancer Res., 56:645–650 [1996]) showed that the presence of telomerase RNA in various human tumor tissues and cell lines was not a good predictor of the presence or amount of telomerase activity in these tissues and cell lines.

In ciliates (single celled eukaryotic organisms), it has been found that the protein portion of telomerase is comprised of two distinct polypeptides, termed p80 and p95 (see PCT patent application WO 96/19580, published Jun. 27, 1995; Harrington et al., J. Biol. Chem, 270:8893–8901 [1995]; and Collins et al., Cell, 81:677–686 [1995]). Recently, two telomerase polypeptides of molecular weight 120 kDa and 43 kDa have reportedly been purified in Euplotes, a single-celled eukaryotic organism (Lingner et al., Proc. Natl. Acad. Sci. USA, 93:10712–10717 [1996]). Prior to the present invention, the protein component or components of mammalian telomerase had not been identified.

Recently, a 347 base pair nucleic acid molecule was deposited in the public database Genbank as accession number H33937. This nucleic acid molecule was apparently identified from rat PC-12 cells that had been treated with NGF (neurotrophic growth factor). No function for this nucleic acid molecule or the protein encoded by it is set forth in the Genbank database information, however, a portion of this molecule has been found to be highly homologous to a region of the mouse telomerase RNA interacting protein 1 (TRIP1) of the present invention.

In view of the devastating effects of cancer and AIDS, there is a need in the art to identify molecules in the human body which may have an important role in the etiology of these diseases, and to manipulate the expression of such molecules in patients suffering from these and related diseases.

Accordingly, it is an object of this invention to provide nucleic acid molecules and polypeptides that affect aging and/or proliferation of cells in the human body.

It is a further object to provide methods of altering the level of expression of such nucleic acid molecules and polypeptides in the human body.

Other related objects will readily be apparent from a reading of this disclosure.

SUMMARY OF THE INVENTION

In one embodiment, the present invention provides a TRIP1 nucleic acid molecule encoding a polypeptide selected from the group consisting of: the nucleic acid molecule of SEQ ID NO:1; the nucleic acid molecule of SEQ ID NO:2; a nucleic acid molecule encoding the polypeptide of SEQ ID NO:3, SEQ ID NO:4, or a biologically active fragment thereof; a nucleic acid molecule that encodes a polypeptide that is at least 70 percent identical to the polypeptide of SEQ ID NO:3 or SEQ ID NO:4; a nucleic acid molecule that hybridizes under stringent conditions to any of the above nucleic acids; and a nucleic acid molecule that is the complement of any of the above nucleic acids.

In another embodiment, the invention provides a nucleic acid molecule encoding amino acids 1–871 of the polypeptide of SEQ ID NO:3.

In one other embodiment, the invention provides vectors comprising the nucleic acids listed above, where the vectors can be amplification or expression vectors, suitable for use in prokaryotic or eukaryotic cells. Also provided are host cells comprising these vectors, wherein the host cells may be prokaryotic or eukaryotic cells.

The invention additionally provides a process for producing a TRIP1 polypeptide comprising the steps of: expressing a polypeptide encoded by the nucleic acid of claim 1 in a suitable host and isolating the polypeptide, wherein the TRIP1 polypeptide may be SEQ ID NO:3, SEQ ID NO:4, or amino acids 1–871 of SEQ ID NO:3.

In yet another embodiment, the invention comprises a TRIP1 polypeptide selected from the group consisting of: the polypeptide of SEQ ID NO:3; the polypeptide that is amino acids 1–871 of SEQ ID NO:3; a polypeptide that is at least 70 percent identical to one of these polypeptides, or a polypeptide that is a biologically active fragment of one of these polypeptides.

BRIEF DESCRIPTION OF THE DRAWINGS

FIG. 1 (A–I) depicts the full length cDNA sequence of human TRIP1 (SEQ ID NO:1).

FIG. 2 (A–I) depicts the full length cDNA sequence of mouse TRIP1 (SEQ ID NO:2).

FIG. 3 (A–C) depicts the putative full length amino acid sequence (SEQ ID NO:3) of human TRIP1 as translated from the cDNA sequence.

FIG. 4 (A–C) depicts the putative full length amino acid sequence (SEQ ID NO:4) of mouse TRIP1 as translated from the cDNA sequence.

DETAILED DESCRIPTION OF THE INVENTION

Included in the scope of this invention are TRIP1 (referred to herein as "TRIP1") polypeptides such as the polypeptides of SEQ ID NO:3 and SEQ ID NO:4, and related biologically active polypeptide fragments and derivatives thereof. Further included within the scope of the present invention are nucleic acid molecules that encode these polypeptides, and methods for preparing the polypeptides. Such molecules may be useful as therapeutic agents in those cases where increasing TRIP1 activity is desired.

In those situations in which TRIP1 activity is to be decreased, such as in cancer cells in which TRIP1 activity is elevated as compared to non-cancerous cells, TRIP1 may serve as a target to identify a molecule which inhibits TRIP1 activity. Techniques that may be useful in identifying such TRIP1 inhibiting molecules are described in detail below. Alternatively, ex vivo or in vivo gene therapy may be employed to administer either TRIP1 anti-sense molecules, or DNA constructs that may serve to disrupt or enhance TRIP1 expression in the cells.

Also included within the scope of the present invention are non-human mammals such as mice, rats, rabbits, goats, or sheep in which the gene (or genes) encoding native TRIP1 has been disrupted ("knocked out") such that the level of expression of this gene is significantly decreased or completely abolished. Such mammals may be prepared using techniques and methods such as those described in U.S. Pat. No. 5,557,032. The present invention further includes non-human mammals such as mice, rats, rabbits, goats, or sheep in which the gene (or genes) encoding the TRIP1 (either the native form of TRIP1 for the mammal or a heterologous TRIP1 gene) is over expressed by the mammal, thereby creating a "transgenic" mammal. Such transgenic mammals may be prepared using well known methods such as those described in U.S. Pat. No 5,489,743 and PCT patent application no. WO94/28122, published Dec. 8, 1994.

The term "TRIP1 protein" or "TRIP1 polypeptide" as used herein refers to any protein or polypeptide having the properties described herein for TRIP1, or TRIP1. The small letter in front of the letters "TRIP1", when used, refers to a TRIP1 polypeptide from a particular mammal, i.e., "hTRIP1" refers to human TRIP1, and "mTRIP1" refers to mouse TRIP1. The TRIP1 polypeptide may or may not have an amino terminal methionine, depending on the manner in which it is prepared. By way of illustration, TRIP1 protein or TRIP1 polypeptide refers to (1) an amino acid sequence encoded by TRIP1 nucleic acid molecules as defined in any of items (a)–(f) below, and biologically active peptide or polypeptide fragments derived therefrom, (2) naturally occurring allelic variants of the TRIP1 gene which result in one or more amino acid substitutions, deletions, and/or insertions as compared to the TRIP1 polypeptide of SEQ ID NO:3 or SEQ ID NO:4, and/or (3) chemically modified derivatives as well as nucleic acid and or amino acid sequence variants thereof as provided for herein.

As used herein, the term "TRIP1 fragment" refers to a peptide or polypeptide that is less than the full length amino acid sequence of naturally occurring TRIP1 protein but has substantially the same biological activity as TRIP1 polypeptide or TRIP1 protein described above. Such a fragment may be truncated at the amino terminus, the carboxy terminus, and/or internally, and may be chemically modified. Such TRIP1 fragments may be prepared with or without an amino terminal methionine.

As used herein, the term "TRIP1 derivative" or "TRIP1 variant" refers to a TRIP1 polypeptide, protein, or fragment that 1) has been chemically modified, as for example, by addition of one or more polyethylene glycol molecules, sugars, phosphates, or other such molecules not naturally attached to wild-type TRIP1 polypeptide, and/or 2) contains one or more nucleic acid or amino acid sequence substitutions, deletions, and/or insertions as compared to TRIP1 set forth in FIGS. 3 or 4.

As used herein, the terms "biologically active polypeptide" and "biologically active fragment" refer to a TRIP1 peptide or polypeptide in accordance with the above description for TRIP1 that has at least one of the following activities which have been identified for TRIP1: (1) specifically binding to telomerase RNA; and (2) binding to an antibody that is directed to an epitope on the polypeptide of SEQ ID NO:3 or SEQ ID NO:4.

As used herein, the term "TRIP1" when used to describe a nucleic acid molecule refers to a nucleic acid molecule or fragment thereof that (a) has the nucleotide sequence as set forth in SEQ ID NO:1 or SEQ ID NO:2; (b) has a nucleic acid sequence encoding a polypeptide that is at least 70 percent identical, but may be greater than 70 percent, i.e., 80 percent, 90 percent, or even greater than 90 percent identical, to the polypeptide encoded by any of SEQ ID NOS:1 or 2; (c) is a naturally occurring allelic variant of (a) or (b); (d) is a nucleic acid variant of (a)–(c) produced as provided for herein;(e) has a sequence that is complementary to (a)–(d); and/or (f) hybridizes to any of (a)–(e) under stringent conditions.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span", which can include the full length of one or both sequences, or a pre-determined portion of one or both sequences). Each computer program provides a "default" opening penalty and a "default" gap penalty, and a scoring matrix such as PAM 250. A standard scoring matrix (see Dayhoff et al., in: *Atlas of Protein Sequence and Structure*, vol. 5, supp.3 [1978]) can be used in conjunction with the computer program. The percent identity can then be calculated by determining the percent identity using an algorithm contained in a program such as FASTA:

$$\frac{\text{Total number of identical matches}}{[\text{length of the longer sequence within the matched span}] + [\text{number of gaps introduced into the longer sequence in order to align the two sequences}]} \times 100$$

Polypeptides that are at least 70 percent identical will typically have one or more amino acid substitutions, deletions, and/or insertions as compared with wild type TRIP1. Usually, the substitutions will be conservative so as to have little or no effect on the overall net charge, polarity, or hydrophobicity of the protein but optionally may increase the activity of TRIP1. Conservative substitutions are set forth in Table I below.

TABLE I

Conservative Amino Acid Substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The term "stringent conditions" refers to hybridization and washing under conditions that permit only binding of a nucleic acid molecule such as an oligonucleotide or cDNA molecule probe to highly homologous sequences. One stringent wash solution is 0.015M NaCl, 0.005M NaCitrate, and 0.1 percent SDS used at a temperature of 55° C.–65° C. Another stringent wash solution is 0.2×SSC and 0.1 percent SDS used at a temperature of between 50° C.–65° C. Where oligonucleotide probes are used to screen cDNA or genomic libraries, the following stringent washing conditions may be used. One protocol uses 6×SSC with 0.05 percent sodium pyrophosphate at a temperature of 35° C.–62° C., depending on the length of the oligonucleotide probe. For example, 14 base pair probes are washed at 35–40° C., 17 base pair probes are washed at 45–50° C., 20 base pair probes are washed at 52–57° C., and 23 base pair probes are washed at 57–63° C. The temperature can be increased 2–3° C. where the background non-specific binding appears high. A second protocol utilizes tetramethylammonium chloride (TMAC) for washing oligonucleotide probes. One stringent washing solution is 3M TMAC, 50 mM Tris-HCl, pH 8.0, and 0.2 percent SDS. The washing temperature using this solution is a function of the length of the probe. For example, a 17 base pair probe is washed at about 45–50° C.

As used herein, the terms "effective amount" and "therapeutically effective amount" refer to the amount of TRIP1 necessary to support one or more biological activities of TRIP1 as set forth above.

The TRIP1 polypeptides that have use in practicing the present invention may be naturally occurring full length polypeptides, or truncated polypeptides or peptides (i.e, "fragments"). The polypeptides or fragments may be chemically modified, i.e., glycosylated, phosphorylated, and/or linked to a polymer, as described below, and they may have an amino terminal methionine, depending on how they are prepared. In addition, the polypeptides or fragments may be variants of the naturally occurring TRIP1 polypeptide (i.e., may contain one or more amino acid deletions, insertions, and/or substitutions as compared with naturally occurring TRIP1).

The full length TRIP1 polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, N.Y. [1994]). A gene or cDNA encoding the TRIP1 protein or fragment thereof may be obtained for example by screening a genomic or cDNA library, or by PCR amplification. Alternatively, a gene encoding the TRIP1 polypeptide or fragment may be prepared by chemical synthesis using methods well known to the skilled artisan such as those described by Engels et al. (*Angew. Chem. Intl. Ed.,* 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the TRIP1 polypeptide will be several hundred nucleotides in length. Nucleic acids larger than about 100 nucleotides can be synthesized as several fragments using these methods. The fragments can then be ligated together to form the full length TRIP1 polypeptide. Usually, the DNA fragment encoding the amino terminus of the polypeptide will have an ATG, which encodes a methionine residue. This methionine may or may not be present on the mature form of the TRIP1 polypeptide, depending on whether the polypeptide produced in the host cell is secreted from that cell.

In some cases, it may be desirable to prepare nucleic acid and/or amino acid variants of naturally occurring TRIP1. Nucleic acid variants (wherein one or more nucleotides are designed to differ from the wild-type or naturally occurring TRIP1) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce TRIP1. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s) on TRIP1, or those designed to delete an existing glycosylation and/or phosphorylation site(s) on TRIP1.

The TRIP1 gene or cDNA can be inserted into an appropriate expression vector for expression in a host cell. The vector is typically selected to be functional in the particular host cell employed (i.e., the vector is compatible with the host cell machinery such that amplification of the TRIP1 gene and/or expression of the gene can occur). The TRIP1 polypeptide or fragment thereof may be amplified/expressed in prokaryotic, yeast, insect (baculovirus systems) and/or eukaryotic host cells. Selection of the host cell will depend at least in part on whether the TRIP1 polypeptide or fragment thereof is to be glycosylated and/or phosphorylated. If so, yeast, insect, or mammalian host cells are preferable; yeast cells can typically glycosylate and phosphorylate the polypeptide, and insect and mammalian cells can glycosylate and/or phosphorylate the polypeptide as it naturally occurs on the TRIP1 polypeptide (i.e., "native" glycosylation and/or phosphorylation).

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide sequence located at the 5' or 3' end of the TRIP1 coding sequence that encodes polyHis (such as hexaHis) or another small immunogenic sequence. This tag will be expressed along with the protein, and can serve as an affinity tag for purification of the TRIP1 polypeptide from the host cell. Optionally, the tag can subsequently be removed from the purified TRIP1 polypeptide by various means such as using a selected peptidase for example.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native TRIP1 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the TRIP1 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the TRIP1 polypeptide. If the vector of choice does not contain an origin of replication site, one may be chemically synthesized based on a known sequence, and ligated into the vector.

The transcription termination element is typically located 3' of the end of the TRIP1 polypeptide coding sequence and serves to terminate transcription of the TRIP1 polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the TRIP1 polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for TRIP1 to be secreted from the host cell, a signal sequence may be used to direct the TRIP1 polypeptide out of the host cell where it is synthesized, and the carboxy-terminal part of the protein may be deleted in order to prevent membrane anchoring. Typically, the signal sequence is positioned in the coding region of TRIP1 nucleic acid sequence, or directly at the 5' end of the TRIP1 coding region. Many signal sequences have been identified, and any of them that are functional in the selected host cell may be used in conjunction with the TRIP1 gene. Therefore, the signal sequence may be homologous or heterologous to the TRIP1 polypeptide, and may be homologous or heterologous to the TRIP1 polypeptide. Additionally, the signal sequence may be chemically synthesized using methods set forth above. In most cases, secretion of the polypeptide from the host cell via the presence of a signal peptide will result in the removal of the amino terminal methionine from the polypeptide.

In many cases, transcription of the TRIP1 polypeptide is increased by the presence of one or more introns on the vector; this is particularly true where TRIP1 is produced in eukaryotic host cells, especially mammalian host cells. The introns used may be naturally occurring within the TRIP1 nucleic acid sequence, especially where the TRIP1 sequence used is a full length genomic sequence or a fragment thereof. Where the intron is not naturally occurring within the TRIP1 DNA sequence (as for most cDNAs), the intron(s) may be obtained from another source. The position of the intron with respect to the 5' flanking sequence and the TRIP1 coding sequence is important, as the intron must be transcribed to be effective. As such, where the TRIP1 nucleic acid sequence is a cDNA sequence, the preferred position for the intron is 3' to the transcription start site, and 5' to the polyA transcription termination sequence. Preferably for TRIP1 cDNAs, the intron will be located on one side or the other (i.e., 5' or 3') of the TRIP1 coding sequence such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and mammalian host cells. Such vectors include, inter alia, pCRII (Invitrogen Company, San Diego, Calif.), pBSII (Stratagene Company, Lajolla, Calif.), and pETL (BlueBacII; Invitrogen).

After the vector has been constructed and a TRIP1 nucleic acid has been inserted into the proper site of the vector, the completed vector may be inserted into a suitable host cell for amplification and/or TRIP1 polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize TRIP1 protein which can subsequently be collected from the culture medium (if the host cell secretes it into the medium) or directly from the host cell producing it (if it is not secreted). After collection, the TRIP1 protein can be purified using methods such as molecular sieve chromatography, affinity chromatography, and the like.

Selection of the host cell will depend in part on whether the TRIP1 protein is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. However, where the host cell does not synthesize biologically active TRIP1, the TRIP1 may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis*, Pseudomonas spp., other Bacillus spp., Streptomyces spp., and the like may also be employed in this method.

Many strains of yeast cells known to those skilled in the art are also available as host cells for expression of the polypeptides of the present invention. Additionally, where desired, insect cells may be utilized as host cells in the method of the present invention (Miller et al., *Genetic Engineering* 8:277–298 [1986]).

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of TRIP1 polypeptide produced in the host cell can be evaluated using standard methods known in the art. Such methods include, without limitation, Western blot analysis, SDS-polyacrylamide gel electrophoresis, nondenaturing gel electrophoresis, HPLC separation, immunoprecipitation, and/or activity assays such as DNA binding gel shift assays.

If the TRIP1 polypeptide has been designed to be secreted from the host cells, the majority of polypeptide may be found in the cell culture medium. Polypeptides prepared in this way will typically not possess an amino terminal methionine, as it is removed during secretion from the cell. If however, the TRIP1 polypeptide is not secreted from the host cells, it will be present in the cytoplasm (for eukaryotic, gram positive bacteria, and insect host cells) or in the periplasm (for gram negative bacteria host cells) and may have an amino terminal methionine.

For intracellular TRIP1 protein, the host cells are typically first disrupted mechanically or osmotically to release the cytoplasmic contents into a buffered solution. TRIP1 polypeptide can then be isolated from this solution.

Purification of TRIP1 polypeptide from solution can be accomplished using a variety of techniques. If the polypeptide has been synthesized such that it contains a tag such as Hexahistidine (TRIP1/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing TRIP1). For example, polyhistidine binds with great affinity and specificity to nickel, thus an affinity column of nickel (such as the Qiagen nickel columns) can be used for purification of TRIP1/polyHis. (See for example, Ausubel et al., eds., *Current Protocols in Molecular Biology*, Section 10.11.8, John Wiley & Sons, New York [1993]).

Where the TRIP1 polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the TRIP1 polypeptide will be found primarily in the periplasmic space of the bacteria or the cytoplasm of eukaryotic cells, the contents of the periplasm or cytoplasm, including inclusion bodies (e.g., gramnegative bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the TRIP1 polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The TRIP1 polypeptide in its now soluble form can then be analyzed using gel electrophoresis, immunoprecipitation or the like. If it is desired to isolate the TRIP1 polypeptide, isolation may be accomplished using standard methods such as those set forth below and in Marston et al. (*Meth. Enz.,* 182:264–275 [1990]).

If TRIP1 polypeptide inclusion bodies are not formed to a significant degree in the periplasm of the host cell, the TRIP1 polypeptide will be found primarily in the supernatant after centrifugation of the cell homogenate, and the TRIP1 polypeptide can be isolated from the supernatant using methods such as those set forth below.

In those situations where it is preferable to partially or completely isolate the TRIP1 polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying TRIP1 polypeptide using recombinant DNA techniques, the TRIP1 polypeptides, fragments, and/or derivatives thereof may be prepared by chemical synthesis methods (such as solid phase peptide synthesis) using methods known in the art such as those set forth by Merrifield et al., (*J. Am. Chem. Soc.,* 85:2149 [1963]), Houghten et al. (*Proc Natl Acad. Sci. USA,* 82:5132 [1985]), and Stewart and Young (Solid Phase Peptide Synthesis, Pierce Chem Co, Rockford, Ill. [1984]). Such polypeptides may be synthesized with or without a methionine on the amino terminus. Chemically synthesized TRIP1 polypeptides or fragments may be oxidized using methods set forth in these references to form disulfide bridges. The TRIP1 polypeptides or fragments may be employed as biologically active or immunological substitutes for natural, purified TRIP1 polypeptides in therapeutic and immunological processes.

Chemically modified TRIP1 compositions (i.e., "derivatives") where the TRIP1 polypeptide is linked to a polymer ("TRIP1-polymers") are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. A preferred reactive aldehyde is polyethylene glycol propionaldehyde, which is water stable, or mono C1–C10 alkoxy or aryloxy derivatives thereof (see U.S. Pat. No. 5,252,714). The polymer may be branched or unbranched. Included within the scope of TRIP1-polymers is a mixture of polymers. Preferably, for therapeutic use of the end-product preparation, the polymer will be pharmaceutically acceptable. The water soluble polymer or mixture thereof may be selected from the group consisting of, for example, polyethylene glycol (PEG), monomethoxypolyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. For the acylation reactions, the polymer(s) selected should have a single reactive ester group. For reductive alkylation, the polymer(s) selected should have a single reactive aldehyde group. The polymer may be of any molecular weight, and may be branched or unbranched.

Pegylation of TRIP1 may be carried out by any of the pegylation reactions known in the art, as described for example in the following references: *Focus on Growth Factors* 3:4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

Pegylation by acylation generally involves reacting an active ester derivative of polyethylene glycol (PEG) with an TRIP1 protein. Any known or subsequently discovered reactive PEG molecule may be used to carry out the pegylation of TRIP1. A preferred activated PEG ester is PEG esterified to N-hydroxysuccinimide ("NHS"). As used herein, "acylation" is contemplated to include without limitation the following types of linkages between TRIP1 and a water soluble polymer such as PEG: amide, carbamate, urethane, and the like, as described in *Bioconjugate Chem.* 5:133–140 (1994). Reaction conditions may be selected from any of those known in the pegylation art or those subsequently developed, provided that conditions such as temperature, solvent, and pH that would inactivate the TRIP1 species to be modified are avoided.

Pegylation by acylation usually results in a poly-pegylated TRIP1 product, wherein the lysine ε-amino groups are pegylated via an acyl linking group. Preferably, the connecting linkage will be an amide. Also preferably, the resulting product will be at least about 95 percent mono, di- or tri-pegylated. However, some species with higher degrees of pegylation (up to the maximum number of lysine ε-amino acid groups of TRIP1 plus one α-amino group at the amino terminus of TRIP1) will normally be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with a protein such as TRIP1 in the presence of a reducing agent. Regardless of the degree of pegylation, the PEG groups are preferably attached to the protein via a —$CH_2$—NH— group. With particular reference to the —$CH_2$— group, this type of linkage is referred to herein as an "alkyl" linkage.

Derivatization via reductive alkylation to produce a monopegylated product exploits the differential reactivity of different types of primary amino groups (lysine versus the N-terminal) available for derivatization in TRIP1. Typically, the reaction is performed at a pH (see below) which allows one to take advantage of the $pK_a$ differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer occurs predominantly at the N-terminus of the protein without significant modification of other reactive groups such as the lysine side chain amino groups. The present invention provides for a substantially homogeneous preparation of TRIP1-monopolymer protein conjugate molecules (meaning TRIP1 protein to which a polymer molecule has been attached substantially only (i.e., at least about 95%) in a single location on the TRIP1 protein. More specifically, if polyethylene glycol is used, the present invention also provides for pegylated TRIP1 protein lacking possibly antigenic linking groups, and having the polyethylene glycol molecule directly coupled to the TRIP1 protein.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable conditions used to react a biologically active substance with an activated polymer molecule. Methods for preparing pegylated TRIP1 will generally comprise the steps of (a) reacting an TRIP1 polypeptide with polyethylene glycol (such as a reactive ester or aldehyde derivative of PEG) under conditions whereby TRIP1 becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Reductive alkylation to produce a substantially homogeneous population of mono-polymer/TRIP1 protein conjugate molecule will generally comprise the steps of: (a) reacting a TRIP1 protein with a reactive PEG molecule under reductive alkylation conditions, at a pH suitable to permit selective modification of the α-amino group at the amino terminus of said TRIP1 protein; and (b) obtaining the reaction product(s).

For a substantially homogeneous population of mono-polymer/TRIP1 protein conjugate molecules, the reductive alkylation reaction conditions are those which permit the selective attachment of the water soluble polymer moiety to the N-terminus of TRIP1. Such reaction conditions generally provide for $pK_a$ differences between the lysine amino groups and the α-amino group at the N-terminus (the $pK_a$ being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2kDa to about 100 kDa (the term "about" indicating ±1 kDa). The preferred average molecular weight is about 5 kDa to about 50 kDa, particularly preferably about 12 kDa to about 25 kDa. The ratio of water-soluble polymer to TRIP1 protein will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer of any TRIP1 protein having an α-amino group at the amino terminus, and provide for a substantially homogenous preparation of monopolymer/TRIP1 protein conjugate. The term "monopolymer/TRIP1 protein conjugate" is used here to mean a composition comprised of a single polymer molecule attached to an TRIP1 protein molecule. The monopolymer/TRIP1 protein conjugate preferably will have a polymer molecule located at the N-terminus, but not on lysine amino side groups. The preparation will preferably be greater than 90% monopolymer/TRIP1 protein conjugate, and more preferably greater than 95% monopolymer TRIP1 protein conjugate, with the remainder of observable molecules being unreacted (i.e., protein lacking the polymer moiety). The examples below provide for a preparation which is at least about 90% monopolymer/ protein conjugate, and about 10% unreacted protein. The monopolymer/protein conjugate has biological activity.

For the present reductive alkylation, the reducing agent should be stable in aqueous solution and preferably able to reduce only the Schiff base formed in the initial process of reductive alkylation. Preferred reducing agents may be selected from the group consisting of sodium borohydride, sodium cyanoborohydride, dimethylamine borane, trimethylamine borane and pyridine borane. A particularly preferred reducing agent is sodium cyanoborohydride.

Other reaction parameters, such as solvent, reaction times, temperatures, etc., and means of purification of products, can be determined based on the published information relating to derivatization of proteins with water soluble polymers.

A mixture of polymer-TRIP1 protein conjugate molecules may be prepared by acylation and/or alkylation methods, as described above, and one may select the proportion of monopolymer/protein conjugate to include in the mixture. Thus, where desired, a mixture of various protein with various numbers of polymer molecules attached (i.e., di-, tri-, tetra-, etc.) may be prepared and combined with the monopolymer/TRIP1 protein conjugate material prepared using the present methods.

Generally, conditions which may be alleviated or modulated by administration of the present polymer/TRIP1 include those described herein for TRIP1 molecules in general. However, the polymer/TRIP1 molecules disclosed herein may have additional activities, enhanced or reduced activities, or other characteristics, as compared to the non-derivatized molecules.

TRIP1 nucleic acid molecules, fragments, and/or derivatives that do not themselves encode polypeptides that are active in activity assays may be useful as hybridization probes in diagnostic assays to test, either qualitatively or quantitatively, for the presence of TRIP1 DNA or corresponding RNA in mammalian tissue or bodily fluid samples.

TRIP1 polypeptide fragments and/or derivatives that are not themselves active in activity assays may be useful for preparing antibodies to TRIP1 polypeptides.

The TRIP1 polypeptides and fragments thereof, whether or not chemically modified, may be employed alone, or in combination with other pharmaceutical compositions.

The TRIP1 polypeptides and/or fragments thereof may be used to prepare antibodies generated by standard methods. Thus, antibodies that react with the TRIP1 polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will either be of human origin, or will be "humanized", i.e., prepared so as to prevent or minimize an immune reaction to the antibody when administered to a patient. The antibody fragment may be any fragment that is reactive with the TRIP1 of the present invention, such as, $F_{ab}$, $F_{ab'}$, etc. Also provided by this invention are the hybridomas generated by presenting TRIP1 or a fragment thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human TRIP1 polypeptide of the present invention are also encompassed by this invention.

The antibodies may be used therapeutically, such as to inhibit binding of TRIP1 to telomeres or to telomerase RNA, or to inhibit TRIP1 activity in other ways. The antibodies may further be used for in vivo and in vitro diagnostic purposes, such as in labeled form to detect the presence of the TRIP1 in a body fluid.

Therapeutic Compositions and Administration

Therapeutic compositions of TRIP1 are within the scope of the present invention. Such compositions may comprise a therapeutically effective amount of a TRIP1 polypeptide or fragment thereof (either of which may be chemically modified) in admixture with a pharmaceutically acceptable carrier. The carrier material may be water for injection, preferably supplemented with other materials common in solutions for administration to mammals. Typically, a TRIP1 therapeutic compound will be administered in the form of a composition comprising purified TRIP1 polypeptide or fragment (which may be chemically modified) in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor.

The TRIP1 compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of TRIP1 compositions useful for practicing the present invention may be a prepared for storage by mixing the selected composition having the desired degree of purity with optional physiologically acceptable carriers, excipients, or stabilizers (*Remington's Pharmaceutical Sciences*, 18th edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics or polyethylene glycol (PEG).

The TRIP1 composition to be used for in vivo administration must be sterile. This is readily accomplished by filtration through sterile filtration membranes. Where the TRIP1 composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device. Alternatively or additionally, TRIP1 may be administered locally via implantation into the affected area of a membrane, sponge, or other appropriate material on to which TRIP1 polypeptide has been absorbed.

TRIP1 polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22:547–556 [1983]), poly (2-hydroxyethyl-methacrylate) (Langer et al., *J. Biomed. Mater. Res.,* 15:167–277 [1981] and Langer, Chem. Tech., 12:98–105 [1982]), ethylene vinyl acetate (Langer et al., supra) or poly-D(-)-3-hydroxybutyric acid (EP 133,988). Sustained-release compositions also may include liposomes, which can be prepared by any of several methods known in the art (e.g., DE 3,218,121; Epstein et al., *Proc. Natl. Acad. Sci. USA,* 82:3688–3692 [1985]; Hwang et al., *Proc. Natl. Acad. Sci. USA,* 77:4030–4034 [1980]; EP 52,322; EP 36,676; EP 88,046; EP 143,949).

In other cases, TRIP1 may be delivered through implanting into patients certain cells that have been genetically engineered to express and secrete TRIP1 polypeptide. Such cells may be animal or human cells, and may be derived from the patient's own tissue or from another source, either human or non-human. Optionally, the cells may be immortalized. The cells may be implanted into suitable body tissues or organs of the patient.

An effective amount of the TRIP1 composition(s) to be employed therapeutically will depend, for example, upon the therapeutic objectives such as the indication for which TRIP1 is being used, the route of administration, and the condition of the patient. Accordingly, it will be necessary for the therapist to titer the dosage and modify the route of administration as required to obtain the optimal therapeutic effect. A typical daily dosage may range from about 0.1 µg/kg to up to 100 mg/kg or more, depending on the factors mentioned above. Typically, a clinician will administer the TRIP1 composition until a dosage is reached that achieves the desired effect. The TRIP1 composition may therefore be administered as a single dose, or as two or more doses (which may or may not contain the same amount of TRIP1) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

In certain situations, it may be desirable to use gene therapy methods for administration of TRIP1 to patients suffering from HIV infection, AIDS, or other diseases for which TRIP1 is a viable therapeutic agent, such as, for example, premature aging and other aging disorders. In these situations, genomic DNA, cDNA, and/or synthetic DNA encoding TRIP1 or a fragment or variant thereof may be operably linked to a constitutive or inducible promoter (where the promoter may be homologous or heterologous) that is active in the tissue into which the composition will be injected. This construct can then be inserted into a suitable vector such as an adenovirus vector or a retrovirus vector to create a "gene therapy vector". The cells of the patient to be treated (such as, for example, T-cells in AIDS patients) can be removed from the patient, infected with the gene therapy vector using standard transfection procedures for eukaryotic cells, and tested for TRIP1 protein production. Those cells expressing TRIP1 can then be re-introduced into the patient.

Gene therapy methods may also be employed where is desirable to inhibit TRIP1 activity. Here, antisense DNA or RNA with a sequence that is complementary to: (1) full length telomerase RNA, (2) at least the portion of the telomerase RNA that interacts with TRIP1, (3) a portion of the TRIP1 mRNA, or (4) full length TRIP1 MRNA can be prepared, placed into a suitable vector, and transfected into selected cells (previously removed from the patient in an ex vivo manner). The vector is typically selected based on its ability to generate high levels of the anti-sense RNA in conjunction with the host cell's machinery.

Alternatively, gene therapy may be employed to create a dominant-negative inhibitor of TRIP1. In this situation, the DNA encoding a mutant full length or truncated polypeptide of TRIP1 is inserted into a retrovirus or adenovirus, or a comparable vector, and the vector in turn is transfected into the patient's cells in either an ex vivo or in vivo manner. This TRIP1 mutant is designed to (1) compete with endogenous TRIP1 in forming the telomerase complex; and (2) contains one or more insertions, deletions, and/or mutations as compared to wild type TRIP1 such that the telomerase complex is rendered functionally inactive. For example, a TRIP1 truncation mutant in which the portion of the molecule that binds RNA (i.e., approximately amino acids 1–900 of human TRIP1) remains intact, but another portion of TRIP1 such as its telomere binding domain or its protein-protein interaction domain is deleted or otherwise rendered non-functional.

Assays to Screen for Inhibitors of TRIP1

As mentioned above, it would be desirable to inhibit or significantly decrease the level of TRIP1 activity in certain cells such as cancer cells (immortalized cells). Compounds that inhibit TRIP1 activity could be administered either in an ex vivo manner, or in an in vivo manner by local or iv injection, or by oral delivery, implantation device, or the like. The assays described below provide examples of methods useful for identifying compounds that could inhibit TRIP1 activity.

For ease of reading, the following definition is used herein for describing the assays:

"Test molecule(s)" refers to the molecule(s) that is under evaluation as an inhibitor of TRIP1, either by virtue of its potential ability to block the interaction of TRIP1 with telomerase RNA, or by virtue of its potential ability to block the interaction of TRIP1 with telomere binding proteins, with the telomere itself, or with other polypeptides that comprise the telomerase complex.

A. In Vitro Assays Using Purified Protein

Several types of in vitro assays using purified protein may be conducted to identify those compounds that disrupt telomerase activity. Such disruption may be accomplished by a compound that either inhibits the interaction of TRIP1 with the telomeres, or by a compound that inhibits TRIP1 association with telomerase RNA or other protein components of the telomerase enzyme complex.

In one assay, purified TRIP1 protein or a fragment thereof (prepared for example using methods described above) can be immobilized by attachment to the bottom of the wells of a microtiter plate. Radiolabeled telomerase RNA, as well as the test molecule(s) can then be added either one at a time or simultaneously to the wells. After incubation, the wells can be washed and counted using a scintillation counter for radioactivity to determine the degree of TRIP1/telomerase RNA binding in the presence of the test molecule. Typically, the molecule will be tested over a range of concentrations, and a series of control "wells" lacking one or more elements of the test assays can be used for accuracy in evaluating the results. A variation of this assay involves attaching the telomerase RNA to the wells, and adding radiolabeled TRIP1 along with the test molecule to the wells. After incubation and washing, the wells can be counted for radioactivity.

Several means other than radiolabelling are available to "mark" the TRIP1 or telomerase RNA. For example, TRIP1 protein can be radiolabelled using 125-I. Alternatively, a fusion protein of TRIP1 wherein the DNA encoding TRIP1 is fused to the coding sequence of a peptide such as the c-myc epitope. TRIP1-myc fusion protein can readily be detected with commercially available antibodies directed against myc.

Telomerase RNA can be labeled by synthesizing it with radiolabelled nucleotides such as 32-P ATP, and the level of radioactivity can then be measured by scintillation counting. Alternatively, the RNA can be labeled using biotin, digoxigenin, or a comparable compound.

An alternative to microtiter plate type of binding assays comprises immobilizing either TRIP1 or telomerase RNA on agarose beads, acrylic beads or other types of such inert substrates. The inert substrate containing the RNA or TRIP1 can be placed in a solution containing the test molecule along with the complementary component (either RNA or TRIP1) which has been radiolabeled or fluorescently labeled; after incubation, the inert substrate can be precipitated by centrifugation, and the amount of binding between TRIP1 and RNA can be assessed using the methods described above. Alternatively, the insert substrate complex can be immobilized in a column and the test molecule and complementary component passed over the column. Formation of the TRIP1/RNA complex can then be assessed using any of the techniques set forth above, i.e., radiolabeling, antibody binding, or the like.

Another type of in vitro assay that is useful for identifying a molecule to inhibit TRIP1 activity is the Biacore assay system (Pharmacia, Piscataway, N.J.) using a surface plasmon resonance detector system and following the manufacturer's protocol. This assay essentially involves covalent binding of either TRIP1 or telomerase RNA to a dextran-coated sensor chip which is located in a detector. The test molecule and the complementary component can then be injected into the chamber containing the sensor chip either simultaneously or sequentially, and the amount of binding of TRIP1/RNA can be assessed based on the change in molecular mass which is physically associated with the dextran-coated side of the of the sensor chip; the change in molecular mass can be measured by the detector system.

One other assay useful for evaluating test molecule disruption of the TRIP1/RNA complex is the gel shift assay. Here, TRIP1, telomerase RNA, and the test molecule can be incubated together. Typically, the RNA is radiolabelled using standard radioisotopes for nucleic acids (such as 32-P ATP). After incubation, the samples can be run on a non-denaturing acrylamide gel where the acrylamide concentration is about 4–6 percent. The migration pattern of telomerase RNA on the gel can then be evaluated. Where the TRIP1/RNA complex is intact during electrophoresis (even after treatment with the test molecule) migration will be slowed due to the increased molecular weight of the complex. If, however, the test molecule has sufficiently disrupted the TRIP1/RNA complex, telomerase RNA will migrate in a manner comparable to control (un-treated) telomerase RNA. Migration can be detected by autoradiography.

In some cases, it may be desirable to evaluate two or more test molecules together for use in decreasing or inhibiting TRIP1 activity. In these cases, the assays set forth above can be readily modified by adding such additional test molecule(s) either simultaneously with, or subsequently to, the first test molecule. The remainder of steps in the assay can be as set forth above.

B. In Vitro Assays Using Cultured Cells

Cultures of immortalized cells (either normal mammalian cells that have spontaneously gained the ability to replicate indefinitely, normal mammalian cells transformed with oncogenes, or mammalian cells derived from tumors) can be used to evaluate test molecules for TRIP1 inhibition. The immortalized cells can be obtained from any mammal, but preferably will be from human or other primate, canine, or rodent sources.

In one type of cell culture assay, the immortalized cells can be cultured in standard medium such as DMEM, alpha-MEM, or RPMI. Typically, the medium would contain up to about ten percent (v:v) of fetal calf serum. Incubation is typically conducted for 1–5 days. After this incubation, the test molecule or molecules can be added, and the cells incubated for a period of 1–7 days, allowing for 3–8 cell cycles. After washing the cells to remove any residual test molecule, the cells can be harvested and telomerase activity analyzed in an in vitro assay such as the TRAP assay (Kim et al, supra) or the TRF assay (Harley et al., 1990, supra). Inhibition may be manifested by a decrease in telomere length, telomerase activity, or both. For example, two known reverse transcriptase inhibitors, dideoxy GTP and AZT, have been shown to cause a decrease in telomere length in immortalized cells and a decrease in telomerase activity in vitro (Strahl et al., *Mol. Cell. Biol.,* 16:53–65 [1996]).

In another cell assay, human immortalized cells can be transfected with a DNA construct encoding either full length TRIP1 or a truncated version of TRIP1. After transfection, the cells could be incubated for a period of time, after which telomerase activity could be assessed using the TRAP assay, and telomere length assayed by the TRF or other suitable assay.

The following examples are intended for illustration purposes only, and should not be construed as limiting the scope of the invention in any way.

EXAMPLES

1. Molecular Cloning of murine TRIP1 cDNA

Standard methods for library preparation, DNA cloning, and protein expression are set forth in Sambrook et al., (*Molecular Cloning: A Laboratory Manual*, Cold Spring Harbor Laborite Press, Cold Spring Harbor, N.Y. [1989]).

A cDNA library was constructed using RNA purified from adult murine colonic crypt cells. mRNA was isolated from a membrane bound polysomal fraction of RNA (Mechler et al., *Meth, Enz.,* 152:241–248 [1987]). The poly(A+) mRNA fraction was isolated from the total RNA preparation using the FastTrack™ mRNA Isolation Kit (Invitrogen, San Diego, Calif.) according to the manufacturer's recommended procedure. First strand cDNA was generated by reverse transcribing the RNA using random hexanucleotides (RediPrime kit, Amersham, Arlington Heights, Ill.).

A random primed cDNA library was prepared from the first strand cDNA using the Superscript™ Plasmid System (Gibco BRL, Gaithersburg, Md.). A random cDNA primer containing an internal NotI restriction site was used to initiate first strand synthesis and had the following double strand sequence:

CCTCTGCGGCCGCTACANNNNNNNNT (SEQ ID NO: 5)

GGAGACGCCGGCGA' (SEQ ID NO: 6)

The first strand cDNA synthesis reaction was assembled using 1 μg of the mRNA and 150 ng of the Not1 random primer. After second strand synthesis, the reaction products were extracted with the phenol:chloroform:isoamyl alcohol mixture and ethanol precipitated. The double strand (ds) cDNA products were ligated to the following ds oligonucleotide adapter (Gibco BRL):

TCGACCCACGCGTCCG (SEQ ID NO: 7)

GGGTGCGCAGGC (SEQ ID NO: 8)

After ligation the cDNA was digested to completion with Not1, extracted with phenol:chloroform:isoamyl alcohol (25:24:1 ratio) and ethanol precipitated. The resuspended cDNA was then size fractionated by gel filtration using the premade columns provided with the Superscript Plasmid System (Gibco BRL) as recommended by the manufacturer. The fractions containing the largest cDNA products were ethanol precipitated and then directionally ligated into Not1 and Sal1 digested PMOB vector DNA (Strathmann et. al. *Proc. Natl. Acad. Sci USA*, 88:1247–1250 [1991]). The ligated cDNA was introduced into electrocompetent XL1-Blue *E. coli* (Stratagene, Lajolla, Calif.) by electroporation. The library was termed cm1.

Approximately 20,000 colonies from the library were picked and arrayed into 96 well microtiter plates containing about 200 μl of L-broth, 7.5% glycerol, 50 μg/ml ampicillin and 12.5 μg/ml tetracycline. The cultures were grown overnight at 37° C., a duplicate set of microtiter plates were made using a sterile 96 pin replicating tool, and both sets were stored at −80° C. for further analysis.

To sequence random cDNA clones from this library, sequencing template was prepared by PCR amplification of cloned cDNA inserts using vector primers. Glycerol stocks of cDNA clones were thawed, and small aliquots were diluted 1:25 in distilled water. Approximately 3.0 μl of diluted bacterial cultures were added to PCR reaction mixture (Boehringer-Mannheim) containing the following oligonucleotides:

TGTAAAACGACGGCCAGT (SEQ ID NO: 9)

CAGGAAACAGCTATGACC (SEQ ID NO: 10)

The reactions were incubated in a thermocycler (Perkin-Elmer 9600) with the following cycle conditions: 94° C. for 2 minutes; 94° C. for 5 seconds, 50° C. for 5 seconds and 72° C. for 3 minutes for 30 cycles and then a final extension at 72° C. for 4 minutes. After incubation in the thermocycler, the reactions were diluted with about 2.0 ml of water. The amplified DNA fragments were further purified using Centricon columns (Princeton Separations) using the manufacturer's recommended procedures. In some instances, low primer and deoxynucleoside triphosphate concentrations were used in the amplification reactions, and in those instances, Centricon purification was not necessary. The PCR reaction products were sequenced on an Applied Biosystems 373A automated DNA sequencer using T3 primer:

CAATTAACCCTCACTAAAG (SEQ ID NO: 11)

Taq dye-terminator reactions (Applied Biosystems) were conducted following the manufacturer's recommended procedures.

A search of six way translated DNA sequences from these clones was performed to isolate clones that conformed to the following criteria:

1. Potential signal peptide: Translated sequences contain the following: a methionine followed by one to three positively charged residues followed by 6–15 hydrophobic residues followed by 1–2 charged residues, followed by an open reading frame of at least residues.
2. Predicted alpha helical structure. The open reading frame contains sequences that are predicted to contain at least 30% alpha helix as assayed by the Robson/Garnier algorithm contained in the software program Macvector 4.5.
3. Leucine content. The open reading frame contains at least 10% Leucine residues.
4. Cysteine content. The open reading frame contains at least one but not more than 7 cysteine residues.
5. Lack of transmembrane domain. The open reading frame does not contain a sequence of 15–25 consecutive hydrophobic or uncharged residues.

One clone meeting all of these criteria, cm1-85-g3, was selected for further characterization. To identify additional sequence of this clone, a search of clones obtained from a mouse colon tissue cDNA library (prepared essentially as described above) using cm1-85-g3 as a probe resulted in the identification of clone cm3-1-e4, which had overlapping (homologous) sequence with cm1-85-g3, and contained additional 3' sequence, including a 3' termination codon. Clone cm1-85-g3 was about 1322 base pairs (bp) in length, and clone cm3-1-e4 was about 6.9 kb. To obtain the 5' portion of the coding region, PCR amplification was performed using an antisense oligonucleotide corresponding to the 5' end of the cm1-85-g3 clone and an oligonucleotide corresponding to a portion of the pMOB vector polylinker sequence. The template for this PCR reaction was 96 DNA samples. Each sample was prepared by first plating the entire cm1 library at a density of about 10,000 clones on 96 15 cm plates. After culturing, each plate was scraped and the resultant pooled bacteria containing the clones was prepared as a glycerol stock. DNA was prepared from a portion of each pool, and 1–3 μl of each DNA sample was then added to the individual wells.

PCR conditions were: 30 cycles, 94° C. for 20 seconds; 50° C. for 10 seconds, and 72° C. for 30 seconds. Samples were analyzed by agarose gel electrophoresis.

A PCR fragment of about 1.5 kb was isolated from one of the PCR reactions, and was sequenced. A search of various databases with this PCR fragment resulted in the identification of a homologous sequence termed bmst2-15-g6. This clone was sequenced in its entirety, and was found to contain a methionine preceded by several stop codons, indicating a translation start site for the gene.

The three clones cm1-85-g3, cm3-1-e4 and bmst2-15-g6 overlapped to form a contiguous sequence of about 8159 bp in length. Within this sequence was an open reading frame of about 7887 bp comprising about 2629 amino acids.

A FASTA search of this open reading frame against all translated DNA sequences in the Genbank DNA Repository revealed a homology to the Tetrahymena telomerase P80 subunit. Several significant stretches of amino acid homology were found across this Tetrahymena amino acid sequence. One of these regions showed about 46 percent identity over a 90 amino acid length of the Tetrahymena telomerase P80 subunit. Due to its homology with Tetrahymena telomerase, this gene was called murine telomerase RNA interacting protein 1 ("TRIP1").

2. Cloning of human TRIP1 Gene

The human homolog for the murine TRIP1 gene was identified by screening a cDNA library constructed using RNA from the human colon tumor cell line LIM1863 (Willson et al., *Cancer Res.*, 47:2704–2713 [1987]). Total RNA was isolated and the poly(A+) MRNA fraction was obtained using the FastTrac MRNA Isolation Kit (Invitrogen, San Diego, Calif.) according to the manufacturer's recommended procedure. First strand cDNA was generated by reverse transcribing the RNA using random hexanucleotides (RediPrime kit, Amersham, Arlington Heights, Ill.).

A random primed cDNA library was prepared from the first strand cDNA using the Superscript Plasmid System (Gibco BRL, Gaithersburg, Md.). A random cDNA primer containing an internal NotI restriction site was used to initiate first strand synthesis. This primer had the double strand sequence as set forth above for SEQ ID NO:5 and SEQ ID NO:6.

The first strand cDNA synthesis reaction was assembled using 1 μg of the mRNA and 150 ng of the Not1 random primer. After second strand synthesis, the reaction products were extracted with the phenol:chloroform:isoamyl alcohol mixture and ethanol precipitated. The double strand (ds) cDNA products were ligated to a double strand oligonucleotide adapter with the sequence set forth above for SEQ ID NO:7 and SEQ ID NO:8.

After ligation, the cDNA was digested to completion with Not1, extracted with phenol:chloroform:isoamyl alcohol (25:24:1 ratio) and ethanol precipitated. The resuspended cDNA was then size fractionated by gel filtration using the premade columns provided with the Superscript Plasmid System (Gibco/BRL) as recommended by the manufacturer. The fractions containing the largest cDNA products were ethanol precipitated and then directionally ligated into Not1 and Sal1 digested pSPORT vector (Gibco/BRL, Grand Island, N.Y.). The ligated cDNA was introduced into electrocompetent XL1-Blue *E. coli* (Stratagene, LaJolla, Calif.) by electroporation.

The cDNA library was arrayed by plating the entire library at a density of about 10,000 clones per plate on 96 15 cm Petri plates. After incubation, each plate was scraped, and the resultant pooled bacteria was prepared as a glycerol stock. DNA was prepared from an aliquot of each pool, digested with NotI, electrophoresed on a 1% agarose gel and transferred to a charged nylon membrane for Southern blotting. Each of the 96 lanes on the gel thus contained about 10,000 cDNA clones. An approximately 500bp BamHI/HindIII fragment of clone cm1-85-g3 was random prime labeled using standard methods and hybridized to the Southern blot. Hybridization was conducted at 50° C. for at least two hours using Rapid Hyb buffer (Amersham, Arlington Heights, Ill.) and following the manufacturer's protocol. About ten percent of the samples hybridized to the probe. Lanes corresponding to DNA pools 54, 58 and 87 contained the largest inserts, and so these were selected for further analysis.

Glycerol stocks of bacteria containing the indicated pooled clones were plated directly on to nitrocellulose filters covering agar plates, grown for several hours at 30° C., lysed, and hybridized to the cm1-85-g3 500 bp random primed probe. Hybridization conditions were as above using Rapid Hyb buffer. Positive clones were picked and rescreened to isolate single clones from each stock. The three selected clones, called 54, 58, and 87, contained significant overlapping sequence with each other. To identify additional 5' sequence for the human TRIP1 gene, the largest of the three clones, clone 54, was used to generate one antisense oligonucleotide positioned near its 5' end for a PCR primer. The second PCR primer corresponded to the pSPORT vector. The templates for PCR were the same 96 well pools described above. PCR conditions were: 30 cycles, 94° C. for 20 seconds; 50° C. for 10 seconds, and 72° C. for 30 seconds. Samples were analyzed by agarose gel electrophoresis using the antisense oligonucleotide together with an oligonucleotide sequence found in the pSPORT polylinker.

An approximately 1.5 kbp band was identified in pool 96. This pool was then plated and screened as above except that the filters were hybridized at 60° C. using Rapid Hyb buffer as above for at least two hours. The probe was an antisense oligonucleotide to the 5' end of clone 54, and was radiolabeled at the 5' end using standard methods as follows. About 170 μg of the probe was incubated at about 37° C. for about one hour in a solution containing about 200 μCi of 32-P labeled ATP (Amersham, Arlington Heights, Ill.) and about 20 U of Polynucleotide Kinase (Boehringer Manheim, Indianapolis, Ind.), using a buffer provided by the manufacturer. Radiolabeled oligonucleotide was separated from unincorporated nucleotide by centrifugation through a G25 Quickspin column (Boehringer Manheim) according to the manufacturer's protocol.

To identify the 3' region of the human TRIP1 gene, a sense oligonucleotide corresponding to the 3' end of clone 54 and an oligonucleotide sequence corresponding to the pSPORT polylinker were used in a PCR reaction. The same 96 well pools were used as a template for PCR reactions.

PCR conditions were: 30 cycles, 94° C. for 20 seconds; 55° C. for 10 seconds, and 72° C. for 30 seconds. Samples were analyzed by agarose gel electrophoresis.

A 3 kb PCR product was identified from DNA pool 63. This pool was then plated and screened as above. The probe for this reaction was a sense oligonucleotide to the 3' end of clone 54 which was radiolabeled at the 5' end using standard methods. Two colonies containing DNA clones which strongly hybridized to the probe were identified then sequenced in their entirety. These clones were termed 96 and 63.

To identify the remaining 3' portion of the coding sequence, another round of PCR was conducted. Here, the primers used were (1) a sense oligonucleotide to the 3' end of clone 63 and (2) an oligonucleotide corresponding to the SP6 of the pSPORT vector. PCR conditions were: 30 cycles, 94° C. for 20 seconds; 55° C. for 10 seconds, and 72° C. for 30 seconds. The templates for PCR were the same 96 well pools. Samples were analyzed by agarose gel electrophoresis. An approximately 200 bp fragment was identified in pool 15. This pool was then plated and screened as above by hybridizing the filters with a radiolabeled probe. The probe for this reaction was a sense oligonucleotide to the 3' end of clone 63 which was radiolabeled at the 5' end using standard methods. This clone, clone 15, was sequenced in its entirety and was found to possess a termination codon.

3. Murine TRIP1 Protein Preparation

A truncated version of murine TRIP1 protein encoding amino acids 1–871 was prepared as follows. The DNA encoding this region was obtained by PCR using the following two oligonucleotides: (1) an oligonucleotide encoding a SalI restriction site followed by the first six amino acids of murine TRIP1 and (2) an oligonucleotide corresponding to amino acids 866–871 followed by a TAG stop codon and a SalI restriction site. The template for this reaction were clones cm1-85-g3, cm3-1-e4 and bmst2-15-g6. PCR reactions were 15 cycles, 94° C. for 20 seconds, 55° C. for 10 seconds, and 72° C. for 30 seconds.

This reaction resulted in a band of approximately 2.6 kb on an agarose gel. This band was purified from the gel, digested with SalI and cloned into the XhoI site of the vector pCR3MycTag. pCR3MycTag was prepared as follows. The vector pCR3 (Invitrogen, San Diego, Calif.) was digested with KpnI and XhoI. A nucleic acid molecule encoding two copies of the c-myc epitope and an initiation Methionine was inserted into pCR3. The sequence of this insert is set forth below as SEQ ID NO:12. The resulting plasmid containing the TRIP1 insert (cDNA encoding amino acids 1–871) was termed pCR3MycTag2.

GGTACCGCCAGCCGAGCCACATCGCTCA-
GACACCATGATCGCAAATGTGAATATTG
CTCAGGAACAAAAGCTTATTTCTGAA-
GAAGACTTGGCTCAGGAACAAAAGCTTATT
TCTGAAGAAGACTTGGCTCAGCAGAGTG-
GCGGAGGACTCGAG (SEQ ID NO:12)

A second plasmid, pCR3MycTag3, which contained the cDNA encoding full length murine TRIP1, was prepared as follows. The plasmid pCR3MycTag2 was digested with EcoRI and XbaI (which served to delete the cDNA encoding amino acids 816–871 from the vector), and an XbaI/SalI linker was ligated into the digested plasmid. An EcoRI/SalI fragment 5.4 of clone cm3-1-e4 (corresponding to amino acids 816 to 2627 of murine TRIP1) was ligated into the vector. The resulting plasmid, pCR3MycTag3, has the following components (from 5' to 3'): an initiation codon, two c-myc epitopes, and the full length murine TRIP1 cDNA.

Full length and truncated (amino acids 1–871) murine TRIP1 protein was prepared as follows. Plasmid DNA from pCR3MycTag2 and pCR3MycTag3 was transfected into murine neuroblastoma N2A cells (American Type Culture Collection, catalog no. CCL131) by lipofection using the Perfect Lipid Transfection kit (Invitrogen, San Diego, Calif.). These cells are commonly used for transient and stable expression of foreign proteins. About 24 hours prior to transfection, the cells were seeded at about 700,000 per 100 mm dish in DMEM plus ten percent fetal calf serum, and PSG (penicillin, streptomycin, and glutamine). For lipofection, the cells were placed in about 6 ml of Optimem I reduced serum medium (Gibco/BRL, Grand Island, N.Y.) and about 174 μg of Pfx-6 (Invitrogen) and 29 μg of DNA were added. The cells were incubated for about 4 hours after which time the medium was replaced with fresh DMEM, fetal calf serum, and PSG medium as described above. The cells were harvested after about 24 hours, and were lysed using a Qiagen shredder (Qiagen, Chatsworth, Calif.) according to the manufacturer's protocol. Protein lysates were electrophoresed by 6 percent SDS-PAGE, transferred to a nylon membrane using standard methods, and incubated with a mouse monoclonal anti-myc antibody (Oncogene Research Products, Cambridge, Mass.). Binding of the anti-myc antibody was detected with a HRP-conjugated secondary antibody, and the complex was visualized using ECL (Amersham, Arlington Heights, Ill.) following the manufacturer's protocol. Cells transfected with the vector containing the TRIP1 truncated cDNA showed a prominent band of about 97 kD (corresponding to a polypeptide of about 871 amino acids), while cells transfected with the vector containing full length TRIP1 showed a prominent band of about 280 kD (corresponding to a polypeptide of about 2625 amino acids). These results indicated that TRIP1 truncated or full length protein was expressed in the cells.

4. Murine TRIP1 RNA-Binding Assay

To determine whether mTRIP1 had a specific interaction with the RNA molecule known to be mouse telomerase RNA, the three hybrid assay as described by SenGupta et al. (*Proc. Natl. Acad. Sci USA*, 93:8496–8501 [1996]) was used. The starting plasmid described by SenGupta et al., pMS2-2, was altered by inserting, using standard ligation methods, a DNA encoding the full length mouse telomerase RNA transcript (mTR; Blasco et al., *Science*, 269:1267–1270 [1995]) into the SmaI polylinker site of pMS2-2 in the same orientation as the two MS2 DNA sequences at the 3' end of the polylinker region. (The RNA molecules α-mTR, TLC1, IRE and the mutant mTR molecules, all described in Table I below, were constructed in this same manner; U2, U4, and U6 were similarly tagged with the MS2 hairpins, but were inserted into a different URA3 selectable yeast plasmid, pRS316 [Sikorski et al., *Genetics*, 122:19–27, 1989]).

After this ligation, the resultant plasmid was digested with EcoRI, and the approximately 700 base pair (bp) fragment containing 5' to 3', mTR and the two MS2 DNA sequences, was isolated by standard agarose gel purification methods. This 700 bp fragment was then inserted into plasmid pII-IEx426 (SenGupta et al., supra) which had been previously digested with EcoRI. This plasmid was referred to as pIII-mTR.

A second plasmid was also prepared as follows. The starting plasmid was pACTII (Legrain et al., *Nuc. Acids Res.*, 22:3241–3242 [1994]). pACTII was first digested with the enzyme BamHI, and the ends were blunted using T4 DNA polymerase. An SspI/XbaI fragment of plasmid pCR3MycTag2 (see above) was isolated using standard gel purification methods and blunt ended using T4 DNA polymerase. This fragment, which was about 2739 bp, contained 126 bp (42 amino acids) of vector sequence at the 5' end and the first 871 amino acids of mTRIP1. The fragment was inserted into the BamHI digested pACTII, and the resultant plasmid was referred to as pACTII/MTRIP1-S/X.

Plasmids pACTII/MTRIP1-S/X and pIII-mTR were introduced into yeast cells (strain L40-coat; SenGupta et al., supra) which had been cultured in standard yeast media (YEPD; Sherman et al., *Meth. Yeast Genet.*, Cold Spring Harbor Laboratory Press, Cold Spring Harbor, N.Y. [1983]). Introduction (also referred to as transformation) of the plasmids was accomplished using standard methods such as those described by Chen et al. (*Curr. Genet.*, 21:83–84 [1992]). Co-transformants (i.e., those yeast cells that contained both introduced plasmids) were selected by culturing the cells on yeast agar plates lacking leucine and uracil (SD-ura-leu; Sherman et al., supra) for two days at about 30° C. Eight separate, randomly selected colonies of cells that grew on these plates were repatched on fresh SD-ura-leu plates, and incubated as above. A small portion of each colony was plated on to yeast agar plates lacking uracil, leucine, histidine, and containing 5–20 mM 3-aminotriazole (Sigma, ST. Louis, Mo.), and the plates were incubated 3 days at about 30° C., after which time the number of colonies that grew (out of a total of eight) was assessed.

The results are shown in Table II below.

TABLE II

| RNA | PROTEIN | INTERACTION | | |
|---|---|---|---|---|
| | | 5 mM | 10 mM | 20 mM |
| mTR | mTRIP1 | 8/8 | 8/8 | 8/8 |
| mTR-1 | mTRIP1 | 8/8 | 8/8 | 8/8 |
| mTR-3 | mTRIP1 | 8/8 | 8/8 | 8/8 |
| mTR-27 | mTRIP1 | 8/8 | 8/8 | 8/8 |
| U2 | mTRIP1 | 0/8 | 0/8 | 0/8 |
| U4 | mTRIP1 | 0/8 | 0/8 | 0/8 |
| U6 | mTRIP1 | 0/8 | 0/8 | 0/8 |
| TLC1 | mTRIP1 | 0/8 | 0/8 | 0/8 |
| α-mTR | mTRIP1 | 0/8 | 0/8 | 0/8 |
| mTR-1 | IRP | 0/8 | 0/8 | 0/8 |
| IRE | IRP | 8/8 | 8/8 | 8/8 |
| IRE | mTRIP1 | 7/8 | 7/8 | 7/8 |
| MS2 | mTRIP1 | 7/8 | 6/8 | 5/8 |

In Table II, the column labeled "RNA" refers to the MS2 tagged RNA molecules that were tested. mTR is wild type mouse telomerase RNA; mTR-1 is a substitution mutant of mTR and contains a T instead of a C at position 142 (relative to the transcription start site; see Blasco et al. supra), a C instead of a G at position 202, and an A instead of a G at position 227; mTR-3 contains an A instead of a G at position 272 and is also an insertion mutant of mTR in which two nucleotides, A and G. were inserted after nucleotide 268 in the mTR transcript (Blasco et al., supra); mTR-27 is a substitution mutant of mTR that contains an A instead of a G at position 33; U2, U4, and U6 are snRNAs (Ares, Cell, 47:44–59 [1986]; Tollervey et al., Cell, 35:753–762 [1983]; Brow et al., Nature, 334:213–218 [1988]); TLC1 is the yeast telomerase RNA gene (Singer et al., Science, 266:404–409 [1994]); α-mTR is the mTR sequence cloned in the antisense direction relative to the MS2 hairpins; IRE is the rat iron regulatory element RNA (SenGupta et al., supra); and MS2 refers to the MS2 hairpins without additional RNA attached.

The column labeled "Protein" refers to proteins that were co-introduced along with the test RNA molecules to evaluate RNA-protein interaction in the three hybrid assay. "mTRIP1" is the amino terminal fragment of the mTRIP1 gene and consists of the amino terminal 871 amino acids of the protein; and IRP is the iron regulatory element binding protein (SenGupta et al., supra).

The column labeled "Interaction" refers to the concentration (5, 10, or 20 mM) of 3-aminotriazole on the yeast agar plates.

The number of colonies of out of a total of eight that showed detectable growth after 3 days is indicated for each RNA/protein pair. As can be seen, the mouse telomerase RNA, whether wild type or mutant, specifically interacted with mTRIP1. With the exception of IRE, the other RNA molecules, U2, U4, U6, TLC1, and α-mTR, did not interact with mTRIP1. MS2 alone interacted with mTRIP1 to some degree at low concentrations of 3-aminotriazole. Specificity of binding of mTR was further confirmed by demonstrating that IRP, which is known to interact with IRE (and was therefore used as a positive control), did not interact with mTR-1.

Deposit of TRIP1 cDNA

E. coli cells containing the plasmid pCR3 with the insert TRIP1MycTag3 (encoding mouse full length TRIP1 polypeptide) has been deposited with the ATCC (American Type Culture Collection, 108011 University Blvd., Manassas, Va., USA) on Nov. 8, 1996 as accession number 98250. In addition, four separate clones of E coli cells containing the plasmid pSPORT into which a portion of the human TRIP1 cDNA coding sequence were deposited with the ATCC on the same date. Clone 15 contains cDNA encoding amino acids 1046–2627 and has ATCC accession number 98254; clone 54 contains cDNA encoding amino acids 423–1467 and has ATCC accession number 98253; clone 63 contains cDNA encoding amino acids 1346–2488 and has ATCC accession number 98252; and clone 96 contains cDNA encoding amino acids 1–567 and has ATCC accession number 98251.

We claim:

1. An isolated nucleic acid molecule having the nucleotide sequence of SEQ ID NO:1.

2. An isolated nucleic acid molecule having the nucleotide sequence of SEQ ID NO:2.

3. An isolated nucleic acid molecule encoding the polypeptide having the amino acid sequence of SEQ ID NO:3.

4. An isolated nucleic acid molecule encoding the polypeptide having the amino acid sequence of SEQ ID NO:4.

5. An isolated nucleic acid molecule encoding amino acids 1–871 of the polypeptide having the amino acid sequence of SEQ ID NO:3.

6. A vector comprising the nucleic acid molecule of claim 1.

7. A vector comprising the nucleic acid molecule of claim 2.

8. A vector comprising the nucleic acid molecule of claim 3.

9. A vector comprising the nucleic acid molecule of claim 4.

10. A vector comprising the nucleic acid molecule of claim 5.

11. A host cell comprising the vector of claim 6.

12. A host cell comprising the vector of claim 7.

13. A host cell comprising the vector of claim 8.

14. A host cell comprising the vector of claim 9.

15. A host cell comprising the vector of claim 10.

16. A process for producing a TRIP1 polypeptide comprising the steps of:
   (a) expressing the polypeptide encoded by the nucleic acid molecule of claim 2, 3, 4, 5, or 6 in a suitable host cell; and
   (b) isolating the polypeptide.

17. The process of claim 16 wherein the polypeptide is SEQ ID NO:3.

18. The process of claim 16 wherein the polypeptide comprises amino acids 1–871 of SEQ ID NO:3.

19. A transformed or transfected host cell expressing TRIP 1 polypeptide encoded by the nucleic acid of claim 2, 3, 4, 5.

* * * * *

UNITED STATES PATENT AND TRADEMARK OFFICE
CERTIFICATE OF CORRECTION

PATENT NO. : 5,919,656
DATED : July 6, 1999
INVENTOR(S) : Harrington, et al.

It is certified that error appears in the above-identified patent and that said Letters Patent is hereby corrected as shown below:

Column 9, line 59: Change "Lajolla" to -- La Jolla --.

Column 20, line 7: Remove the first phrase "of the".

Column 21, line 27: Change "Not1" to -- NotI --.

Column 21, line 37: Change "Not1" to -- NotI --.

Column 21, line 43: Change "Not1" to -- NotI --.

Column 23, line 37: Change "Not1" to -- NotI --.

Column 23, line 45: Change "Not1" to -- NotI --.

Column 23, line 51: Change "Not1" to -- NotI --.

Signed and Sealed this

Sixth Day of February, 2001

*Attest:*

Q. TODD DICKINSON

*Attesting Officer*        Director of Patents and Trademarks